US008414556B2

(12) United States Patent
Garfield et al.

(10) Patent No.: US 8,414,556 B2
(45) Date of Patent: Apr. 9, 2013

(54) SYSTEMS AND METHODS FOR SAFE MEDICAMENT TRANSPORT

(75) Inventors: Jared Garfield, Deerfield, IL (US); John Slump, Sioux City, IA (US); Gregory Lyon, Mamaroneck, NY (US)

(73) Assignee: J & J Solutions, Inc., Coralville, IA (US)

( * ) Notice: Subject to any disclaimer, the term of this patent is extended or adjusted under 35 U.S.C. 154(b) by 0 days.

(21) Appl. No.: 13/613,475

(22) Filed: Sep. 13, 2012

(65) Prior Publication Data

US 2013/0000780 A1 Jan. 3, 2013

Related U.S. Application Data

(62) Division of application No. 12/991,924, filed as application No. PCT/US2009/043976 on May 14, 2009.

(60) Provisional application No. 61/053,022, filed on May 14, 2008, provisional application No. 61/120,058, filed on Dec. 5, 2008.

(51) Int. Cl.
*A61M 5/32* (2006.01)

(52) U.S. Cl. ........ 604/411; 604/407; 604/412; 604/413; 604/416; 141/2; 141/9

(58) Field of Classification Search .................. 604/192, 604/407, 411–416; 141/2, 9
See application file for complete search history.

(56) References Cited

U.S. PATENT DOCUMENTS

| | | | | |
|---|---|---|---|---|
| 3,706,305 A | * | 12/1972 | Berger et al. | 600/575 |
| 4,180,070 A | * | 12/1979 | Genese | 604/88 |
| 4,201,208 A | | 5/1980 | Cambio, Jr. | |

(Continued)

FOREIGN PATENT DOCUMENTS

| | | |
|---|---|---|
| EP | 0 521 264 | 5/1992 |
| EP | 0 667 126 | 8/1995 |

(Continued)

OTHER PUBLICATIONS

I Chou, C.K. (1995). "Radiofrequency Hyperthermia in Cancer Therapy," Biologic Effects of Nonionizing Electromagnetic Fields. Chapter 94, CRC Press, Inc. pp. 1424-1428.

Urologix, Inc.—Medical Professionals: Targis3 Technology (a date prior to the filing of the present application) http://www.urologix.com/medical/technology.html (3 total pages).

International Search Report corresponding to European Application No. EP 06 00 9435.6; completed Jul. 6, 2006 and mailed Jul. 13, 2006; 3 pages.

International Search Report corresponding to International Application No. PCT/US2009/043976, completed Jun. 26, 2009 and mailed Jul. 28, 2009; 3 pages.

*Primary Examiner* — Tatyana Zalukaeva
*Assistant Examiner* — Benjamin Klein
(74) *Attorney, Agent, or Firm* — Carter, DeLuca, Farrell & Schmidt, LLP

(57) ABSTRACT

A medicament transport system includes a syringe adapter assembly; and a vial adapter assembly including a base defining an opening having a seal member disposed therewithin, a stem extending from the base and defining a lumen therethrough and an opening through a wall thereof, a needle shuttle valve slidably disposed within the lumen of the stem and supporting a transfer needle and a vacuum needle; and a vacuum cup slidably supported on the stem, wherein a vacuum chamber is defined in the space between the base, the stem and the vacuum cup. The medicament transport system includes a condition where the transfer needle and the vacuum needles penetrate the seal member of the vial adapter assembly, and the vacuum cup is moved to draw a vacuum through the vacuum needle. An automation system is provided that utilizes a medicament transport system for forming a medicament solution from a liquid/non-liquid solution.

5 Claims, 46 Drawing Sheets

U.S. PATENT DOCUMENTS

| | | | |
|---|---|---|---|
| 4,673,404 | A | 6/1987 | Gustavsson |
| 4,752,292 | A | 6/1988 | Lopez et al. |
| 5,100,394 | A | 3/1992 | Dudar et al. |
| 5,135,489 | A | 8/1992 | Jepson et al. |
| 5,158,554 | A | 10/1992 | Jepson et al. |
| 5,167,648 | A | 12/1992 | Jepson et al. |
| 5,188,620 | A | 2/1993 | Jepson et al. |
| 5,211,638 | A | 5/1993 | Dudar et al. |
| 5,405,340 | A | 4/1995 | Fageol et al. |
| 5,437,650 | A | 8/1995 | Larkin et al. |
| 5,470,327 | A | 11/1995 | Helgren et al. |
| 5,507,733 | A | 4/1996 | Larkin et al. |
| 5,520,666 | A | 5/1996 | Choudhury et al. |
| 5,549,566 | A | 8/1996 | Elias et al. |
| 5,580,351 | A | 12/1996 | Helgren et al. |
| 5,658,260 | A | 8/1997 | Desecki et al. |
| 5,685,842 | A | 11/1997 | Drivas |
| 5,702,374 | A | 12/1997 | Johnson |
| 5,785,682 | A | 7/1998 | Grabenkort |
| 5,785,692 | A | 7/1998 | Attermeier et al. |
| 5,797,897 | A | 8/1998 | Jepson et al. |
| 5,807,345 | A | 9/1998 | Grabenkort |
| 5,810,768 | A | 9/1998 | Lopez |
| 5,871,500 | A | 2/1999 | Jepson et al. |
| 5,891,129 | A | 4/1999 | Daubert et al. |
| 5,899,888 | A | 5/1999 | Jepson et al. |
| 5,924,584 | A | 7/1999 | Hellstrom et al. |
| 5,954,104 | A | 9/1999 | Daubert et al. |
| 5,954,708 | A | 9/1999 | Lopez et al. |
| 5,957,898 | A | 9/1999 | Jepson et al. |
| 5,964,785 | A | 10/1999 | Desecki et al. |
| 6,063,068 | A | 5/2000 | Fowles et al. |
| 6,083,194 | A | 7/2000 | Lopez |
| 6,090,091 | A | 7/2000 | Fowles et al. |
| 6,139,534 | A | 10/2000 | Niedospial, Jr. et al. |
| 6,193,697 | B1 | 2/2001 | Jepson et al. |
| 6,213,996 | B1 | 4/2001 | Jepson et al. |
| 6,245,048 | B1 | 6/2001 | Fangrow, Jr. et al. |
| 6,261,266 | B1 | 7/2001 | Jepson et al. |
| 6,261,282 | B1 | 7/2001 | Jepson et al. |
| 6,302,289 | B1 | 10/2001 | Andersson et al. |
| 6,344,033 | B1 | 2/2002 | Jepson et al. |
| 6,387,074 | B1 | 5/2002 | Horppu et al. |
| 6,394,983 | B1 | 5/2002 | Mayoral et al. |
| 6,409,708 | B1 | 6/2002 | Wessman |
| 6,428,520 | B1 | 8/2002 | Lopez et al. |
| 6,447,498 | B1 | 9/2002 | Jepson et al. |
| 6,524,295 | B2 | 2/2003 | Daubert et al. |
| 6,569,125 | B2 | 5/2003 | Jepson et al. |
| 6,595,964 | B2 | 7/2003 | Finley et al. |
| 6,599,273 | B1 | 7/2003 | Lopez |
| 6,605,076 | B1 | 8/2003 | Jepson et al. |
| 6,635,043 | B2 | 10/2003 | Daubert et al. |
| 6,635,044 | B2 | 10/2003 | Lopez |
| 6,660,527 | B2 | 12/2003 | Stroup |
| 6,669,681 | B2 | 12/2003 | Dudar et al. |
| D488,867 | S | 4/2004 | Chau |
| 6,715,520 | B2 | 4/2004 | Andréasson et al. |
| 6,871,838 | B2 | 3/2005 | Raines et al. |
| 6,874,522 | B2 | 4/2005 | Anderson et al. |
| 6,875,205 | B2 | 4/2005 | Leinsing |
| 7,025,389 | B2 | 4/2006 | Cuschieri et al. |
| 7,040,598 | B2 | 5/2006 | Raybuck |
| 7,044,441 | B2 | 5/2006 | Doyle |
| 7,100,891 | B2 | 9/2006 | Doyle |
| 7,114,701 | B2 | 10/2006 | Peppel |
| 7,175,615 | B2 | 2/2007 | Hanly et al. |
| 7,244,249 | B2 | 7/2007 | Leinsing et al. |
| 7,306,198 | B2 | 12/2007 | Doyle |
| 7,306,584 | B2 | 12/2007 | Wessman et al. |
| 7,314,061 | B2 | 1/2008 | Peppel |
| 7,316,669 | B2 | 1/2008 | Ranalletta et al. |
| 7,358,505 | B2 | 4/2008 | Woodworth et al. |
| 7,396,051 | B2 | 7/2008 | Baldwin et al. |
| 7,425,209 | B2 | 9/2008 | Fowles et al. |
| 7,470,258 | B2 * | 12/2008 | Barker et al. ................. 604/192 |
| 7,497,848 | B2 | 3/2009 | Leinsing et al. |
| 7,497,849 | B2 | 3/2009 | Fangrow, Jr. |
| 7,503,908 | B2 | 3/2009 | Bartholomew |
| 7,510,545 | B2 | 3/2009 | Peppel |
| 7,563,253 | B2 | 7/2009 | Tanner et al. |
| 7,569,036 | B2 | 8/2009 | Domkowski et al. |
| 7,569,043 | B2 | 8/2009 | Fangrow |
| 7,591,449 | B2 | 9/2009 | Raines et al. |
| 7,615,035 | B2 | 11/2009 | Peppel |
| 7,645,271 | B2 | 1/2010 | Fangrow |
| 7,645,274 | B2 | 1/2010 | Whitley |
| 7,651,481 | B2 | 1/2010 | Raybuck |
| 7,670,326 | B2 | 3/2010 | Shemesh |
| 7,713,247 | B2 | 5/2010 | Lopez |
| 7,717,883 | B2 | 5/2010 | Lopez |
| 7,717,884 | B2 | 5/2010 | Lopez |
| 7,717,886 | B2 | 5/2010 | Lopez |
| 7,743,799 | B2 | 6/2010 | Mosler et al. |
| 7,744,581 | B2 | 6/2010 | Wallén et al. |
| 7,753,338 | B2 | 7/2010 | Desecki et al. |
| 7,758,560 | B2 | 7/2010 | Connell et al. |
| 7,762,524 | B2 | 7/2010 | Cawthon et al. |
| 7,763,013 | B2 | 7/2010 | Baldwin et al. |
| 7,763,199 | B2 | 7/2010 | Fangrow, Jr. |
| 7,766,304 | B2 | 8/2010 | Phillips |
| 7,766,897 | B2 | 8/2010 | Ramsey et al. |
| 8,043,864 | B2 | 10/2011 | Stroup |
| 8,119,419 | B2 | 2/2012 | Stroup |
| 8,251,346 | B2 | 8/2012 | Stroup |
| 8,286,671 | B1 * | 10/2012 | Strangis ............................ 141/9 |
| 2002/0115981 | A1 | 8/2002 | Wessman |
| 2002/0177819 | A1 | 11/2002 | Barker et al. |
| 2003/0070726 | A1 | 4/2003 | Andreasson et al. |
| 2003/0187420 | A1 | 10/2003 | Akerlund et al. |
| 2007/0079894 | A1 | 4/2007 | Kraus et al. |
| 2007/0088315 | A1 * | 4/2007 | Haindl .......................... 604/411 |
| 2008/0103455 | A1 | 5/2008 | Domkowski et al. |
| 2008/0103485 | A1 | 5/2008 | Kruger |
| 2008/0172024 | A1 | 7/2008 | Yow |
| 2008/0223484 | A1 | 9/2008 | Horppu |
| 2008/0249498 | A1 | 10/2008 | Fangrow |
| 2008/0264450 | A1 | 10/2008 | Baldwin et al. |
| 2008/0318456 | A1 | 12/2008 | Yow et al. |
| 2009/0216212 | A1 | 8/2009 | Fangrow, Jr. |
| 2009/0243281 | A1 | 10/2009 | Seifert et al. |
| 2009/0270832 | A1 | 10/2009 | Vancaillie et al. |
| 2010/0004602 | A1 | 1/2010 | Nord et al. |
| 2010/0004618 | A1 | 1/2010 | Rondeau et al. |
| 2010/0004619 | A1 | 1/2010 | Rondeau et al. |
| 2010/0004634 | A1 | 1/2010 | Whitley |
| 2010/0036330 | A1 | 2/2010 | Plishka et al. |
| 2010/0049160 | A1 | 2/2010 | Jepson et al. |
| 2010/0055668 | A1 | 3/2010 | Stroup |
| 2010/0106129 | A1 | 4/2010 | Goeckner et al. |
| 2010/0108681 | A1 | 5/2010 | Jepson et al. |
| 2010/0147402 | A1 | 6/2010 | Tornqvist |
| 2010/0152669 | A1 | 6/2010 | Rosenquist |
| 2010/0160889 | A1 | 6/2010 | Smith et al. |
| 2010/0217226 | A1 | 8/2010 | Shemesh |
| 2010/0218846 | A1 | 9/2010 | Kriheli |
| 2010/0241088 | A1 | 9/2010 | Ranalletta et al. |
| 2010/0249745 | A1 | 9/2010 | Ellstrom |
| 2011/0015580 | A1 | 1/2011 | Stroup |
| 2011/0266477 | A1 | 11/2011 | Stroup |
| 2012/0157914 | A1 | 6/2012 | Stroup |

FOREIGN PATENT DOCUMENTS

| | | |
|---|---|---|
| WO | WO 93/20767 | 10/1993 |
| WO | WO 93/20768 | 10/1993 |
| WO | WO 96/34571 | 11/1996 |
| WO | WO 97/48449 | 12/1997 |
| WO | WO 97/48450 | 12/1997 |
| WO | WO 97/48451 | 12/1997 |
| WO | WO 99/56642 | 11/1999 |

| | | | | |
|---|---|---|---|---|
| WO | WO 99/56643 | | | 11/1999 |
| WO | WO 99/56812 | | | 11/1999 |
| WO | WO 00/49957 | | | 8/2000 |
| WO | WO 00/57811 | | | 10/2000 |
| WO | WO 01/60235 | | | 8/2001 |
| WO | WO 02/078777 | | | 10/2002 |
| WO | WO 03/034932 | | | 5/2003 |
| WO | WO 03/039385 | | | 5/2003 |
| WO | WO 03/047043 | | | 6/2003 |
| WO | WO 03/088806 | | | 10/2003 |
| WO | WO 03/088858 | | | 10/2003 |
| WO | WO 2005/011049 | | | 2/2005 |
| WO | WO 2007/015233 | A | | 2/2007 |
| WO | WO 2007/101772 | | | 9/2007 |
| WO | WO 2007/101772 | A1 | | 9/2007 |
| WO | WO 2007101772 | A1 | * | 9/2007 |

* cited by examiner

SYSTEMS AND METHODS FOR SAFE MEDICAMENT TRANSPORT

CROSS-REFERENCE TO RELATED APPLICATIONS

The present application is a Divisional Application claiming the benefit of and priority to U.S. patent application Ser. No. 12/991,924, filed on Dec. 30, 2010, which is a U.S. National Stage Application filed under 35 U.S.C. 371 of International Application No. PCT/US09/43976, filed May 14, 2009, which claims the benefit of and priority to each of U.S. Provisional Application Ser. No. 61/053,022, filed on May 14, 2008, and U.S. Provisional Application Ser. No. 61/120,058, filed on Dec. 5, 2008, the entire content of each of which being incorporated herein by reference.

BACKGROUND

1. Technical Field

The present application relates to systems and methods for the safe transportation of medicaments and, more particularly, to systems and methods for the handling and transport of potentially hazardous medicaments, in particular, cytotoxic drugs and the like.

2. Background of Related Art

Hazardous medicines are frequently applied in the treatment of certain diseases, in particular, for example, in the treatment of cancer. Cytotoxic drugs were once intended to be used to kill cancer cells. However, the use of cytotoxic drugs, in the treatment of cancer cells, presents specific dangers to all cells, both in the patient and in health care providers. Although the exposure to a health care provider is normally very small for each cytotoxic drug dose administration, evidence suggests that chronic, low-dose exposure can produce significant health problems. Accordingly, a system that allows the dispensing of hazardous drugs while eliminating the exposure to providers would be of great benefit.

Drugs are typically supplied in glass or plastic vials that are capped with a gas impermeable liquid seal or stopper. In some instances, the vial contents are a solid powder, such that a liquid needs be injected for mixing. The injection of additional contents (e.g., liquid) into the vial produces an increased pressure which stresses the seal or stopper. Although the vial is intended to be sealed to liquid and gases, drug molecules in vapor phase can leak or pass around the sides of the stopper or through the stopper as the injection needle is withdrawn, thus presenting a hazard to the provider or clinician.

Accordingly, with the potential for aerosol leakage, a means with which to prevent the accidental vapor phase drug egress is required. The provision of a pressure gradient/differential across the seals will ensure that any gas will flow from high to low pressure. Establishing a negative relative pressure between the inside of the transfer volume and atmosphere will prohibit the egress of vapor phase drug.

SUMMARY

The present application relates to systems and methods for the handling and transport of potentially hazardous medicaments, in particular, cytotoxic drugs and the like.

According to an aspect of the present disclosure, a medicament transport system for a medicament contained in a vial is provided. The medicament transport system includes a syringe adapter assembly fluidly connectable to a first container, and a vial adapter assembly fluidly connectable to a second container and configured to slidably receive at least a portion of the syringe adapter sleeve of the syringe adapter assembly. The syringe adapter assembly includes a syringe adapter sleeve; a syringe adapter plunger including a first end slidably disposed within the syringe adapter sleeve and a second end extending from the syringe adapter sleeve; and a syringe adapter needle connected to the first end of the syringe adapter plunger and fluidly connectable to the first container through the syringe adapter plunger. The syringe adapter plunger has at least a first position wherein the syringe adapter needle is disposed within the syringe adapter sleeve and at least a second position wherein at least a portion of the syringe adapter needle extends from the syringe adapter sleeve. The vial adapter assembly includes a transfer adapter sleeve; a shuttle valve slidably disposed within the transfer adapter sleeve; and a transfer adapter needle connected to the shuttle valve and fluidly connectable to the second container through the shuttle valve. The shuttle valve has at least a first position wherein the transfer adapter needle is disposed within the transfer adapter sleeve and is not in fluid communication with the second container, and at least a second position wherein the transfer adapter needle extends from the transfer adapter sleeve and is in fluid communication with the second container.

The syringe adapter sleeve may be translatable relative to the transfer adapter sleeve by an amount sufficient for a distal end of the syringe adapter needle to extend through and out of the transfer adapter sleeve.

The second chamber may be configured to deliver a vacuum to transfer adapter sleeve. The first chamber may be configured to deliver a fluid at a rate, and the second container is configured to draw a vacuum at a rate greater than the rate of fluid delivery of the first chamber.

The syringe adapter needle and the transfer adapter needle may enter the vial when the syringe adapter plunger is at the second position and the shuttle valve is at the second position.

The first chamber may be configured to deliver a fluid to the vial at a rate, and the second container may be configured to draw a vacuum from the vial at a rate greater than the rate of fluid delivery of the first chamber.

The medicament transfer system may further include a biasing member disposed within the syringe adapter sleeve and may be configured to maintain the syringe adapter plunger at the first position.

The medicament transfer system may further include a biasing member disposed within the transfer adapter sleeve and being configured to maintain the shuttle valve at the first position.

A first container may be fluidly connectable to the syringe adapter plunger, and wherein a fluid passage may extend through the syringe adapter plunger and the syringe adapter needle. A second container may be fluidly connectable to the transfer adapter sleeve, and wherein a fluid passage may extend into the transfer adapter sleeve, through the shuttle valve and through the transfer adapter needle, when the shuttle valve is in the second position.

According to another aspect of the present disclosure, a medicament transport system for a medicament contained in a vial is provided. The medicament transport system includes a syringe adapter assembly fluidly connectable to a first container. The syringe adapter assembly includes a body portion defining a lumen therethrough; and a seal member connected to a distal end of the body portion and extending across the lumen thereof. The medicament transport system includes a vial adapter assembly connectable to a neck of the vial and configured to receive the body portion of the syringe adapter assembly. The vial adapter assembly includes a base having at least one retainer configured to engage the neck of the vial, the base defining an opening having a seal member disposed therewithin; a stem extending from the base, the stem defining a lumen therethrough and being in operative communication with the opening of the base, the stem defining an opening through a wall thereof; a needle shuttle valve slidably disposed within the lumen of the stem, the needle shuttle valve forming a fluid tight seal with the stem, the needle shuttle valve supporting a transfer needle such that the transfer needle extends from a first and a second end thereof and supporting a vacuum needle such that the vacuum needle extends from the first end of the needle shuttle valve; and a vacuum cup slidably supported on the stem, the vacuum cup being in fluid tight contact with the stem and with the base, wherein a vacuum chamber is defined in the space between the base, the stem and the vacuum cup. The vacuum chamber is in fluid communication with the lumen of the stem through the opening, formed in the wall of the stem.

The medicament transport system includes a first condition in which the needle shuttle valve is in a retracted position such that the transfer needle and the vacuum needle do not extend through the seal member of the base of the vial adapter, and the vacuum cup is in an advanced position such that the volume of the vacuum chamber is at a minimum.

The medicament transport system includes a second condition in which the body portion of the syringe adapter assembly is advanced through the lumen of the stem such that the second end of the transfer needle penetrates through the seal member of the body portion and the needle shuttle valve is advanced through the lumen of the stem to penetrate the first end of the transfer needle and as tip of the vacuum needle through the seal member of the vial adapter assembly, and wherein the vacuum needle is brought into fluid communication with the opening formed in the wall of the stem.

The medicament transport system includes a third condition in which the vacuum cup is moved to a proximal position thereby enlarging the vacuum chamber and drawing a vacuum through the vacuum needle.

The needle shuttle valve may define an outer annular race, and wherein the vacuum needle may be in fluid communication with the outer annular race of the needle shuttle valve.

The outer annular race of the needle shuttle valve may be in fluid registration with the opening formed in the wall of the stem when the medicament transport system is in the second condition.

The base of the vial adapter assembly may define an outer annular race having a seal member disposed therewithin, and wherein the seal member may be disposed within the outer annular race of the base member forms a fluid tight seal with the vacuum cup.

The vacuum cup may include a base wall defining a central opening configured to receive the stem of the vial adapter assembly, wherein the central opening may define an inner annular race supporting a sealing member therein, wherein the sealing member supported in the inner annular race of the vacuum cup may form a fluid tight seal with the stem.

The vial adapter may include a seal member slidably disposed within the lumen of the stem; and a biasing member interposed between the seal member slidably disposed within the stem and the needle shuttle valve.

In use, when the medicament transport system is in the second condition, a fluid may be injectable into the vial through the syringe adapter assembly, through the transfer needle that has penetrated into the vial and through the syringe adapter assembly.

In use, as a fluid is injected into the vial, the vacuum cup may be moved to the retracted position to thereby draw a vacuum from the vial through the vacuum needle that has penetrated into the vial when the medicament transport system is in the second condition.

According to yet another aspect of the present disclosure, a method of forming a liquid solution from a vial containing a non-liquid material is provided. The method includes the steps of providing a medicament transport system comprising a syringe adapter assembly fluidly connectable to a first container, and a vial adapter assembly connectable to a neck of the vial and configured to receive the body portion of the syringe adapter assembly. The syringe adapter assembly includes a body portion defining a lumen therethrough; and a seal member connected to a distal end of the body portion and extending across the lumen thereof. The vial adapter assembly includes a base having at least one retainer configured to engage the neck of the vial, the base defining an opening having a seal member disposed therewithin; a stem extending from the base, the stem defining a lumen therethrough and being in operative communication with the opening of the base, the stem defining an opening through a wall thereof; a needle shuttle valve slidably disposed within the lumen of the stem, the needle shuttle valve forming a fluid tight seal with the stem, the needle shuttle valve supporting a transfer needle such that the transfer needle extends from a first and a second end thereof and supporting a vacuum needle such that the vacuum needle extends from the first end of the needle shuttle valve; and a vacuum cup slidably supported on the stem, the vacuum cup being in fluid tight contact with the stem and with the base, wherein a vacuum chamber is defined in the space between the base, the stem and the vacuum cup, the vacuum chamber being in fluid communication with the lumen of the stem through the opening formed in the wall of the stem.

The method further includes the steps of connecting the vial containing the non-liquid material to the base of the vial adapter assembly; fluidly connecting a first container having a fluid the body portion of the syringe adapter sleeve; and actuating the syringe adapter sleeve to translate the body portion of the syringe adapter assembly into the stem of the vial adapter sleeve. In use, the needle shuttle valve is caused to be translated relative to the stem of the vial adapter assembly such that a distal end of each of the transfer needle and the vacuum needle are inserted into the vial; the first container is brought into fluid communication with the vial through the transfer needle; and a vacuum is drawn from the vial through the vacuum needle by a movement of the vacuum cup from the advanced position to the proximal position to thereby enlarge the vacuum chamber.

According to still another aspect of the present disclosure, an automation system for forming a medicament solution from a vial containing one of a liquid and a non-liquid material is provided and includes a cabinet housing a carousel configured to hold a plurality of vials, at least one magazine of syringes, a loading arm movable within the cabinet for transporting syringes to vials loaded in the carousel, and a plurality of medicament transport systems for fluidly interconnecting the syringes to the vials. Each medicament transport system includes a syringe adapter assembly fluidly connectable to a first container, and a vial adapter assembly connectable to a neck of the vial and configured to receive the body portion of the syringe adapter assembly. The syringe adapter assembly includes a body portion defining a lumen therethrough; and a seal member connected to a distal end of the body portion and extending across the lumen thereof. The vial adapter assembly includes a base having at least one retainer configured to engage the neck of the vial, the base defining an opening having a seal member disposed therewithin; a stem extending from the base, the stem defining a lumen therethrough and being in operative communication with the opening of the base, the stem defining an opening through a wall thereof; a needle shuttle valve slidably disposed within the lumen of the stem, the needle shuttle valve forming a fluid tight seal with the stem, the needle shuttle valve supporting a transfer needle such that the transfer needle extends from a first and a second end thereof and supporting a vacuum needle such that the vacuum needle extends from the first end of the needle shuttle valve; and a vacuum cup slidably supported on the stem, the vacuum cup being in fluid tight contact with the stem and with the base, wherein a vacuum chamber is defined in the space between the base, the stem and the vacuum cup, the vacuum chamber being in fluid communication with the lumen of the stem through the opening formed in the wall of the stem.

The carousel may include at least one tray configured to support at least one vial, wherein the tray is pivotably connected on the carousel. Each tray may extend in a horizontal direction. The loading arm may be configured to remove a syringe from the magazine, connect a syringe adapter assembly to the syringe, and transport the syringe to a vial having a vial adapter assembly connected thereto. The loading arm may be configured to connect the syringe adapter assembly that is connected to the syringe to the vial adapter assembly that is connected to the vial.

According to yet another aspect of the present disclosure, a process of operating an automation system for effectuating transport of a medicament is provided. The process including the steps of loading a preselected vial containing a quantity of a medicament into an automation system; attaching a vial adapter assembly to the loaded vial; loading syringes into the automation system; loading a plurality of syringe adapters into the automation system; and performing a medicament extraction process. The medicament extraction process includes the steps of selecting an appropriate syringe; connecting a syringe adapter assembly to the selected syringe; moving the syringe into engagement with the loaded vial, wherein a seal of the syringe adapter assembly makes connection with a seal of the vial adapter assembly; advancing the syringe toward the vial until a stopper of the loaded vial is engaged by the seal of the vial adapter assembly; withdrawing a plunger of the syringe relative to a barrel of the syringe to begin withdrawing a fluid from the loaded vial; advancing the plunger relative to the barrel of the syringe to inject fluid back into the loaded vial; and withdrawing the plunger relative to the barrel of the syringe to withdraw the fluid from the loaded vial to complete a transfer of a medicament from the loaded vial to the syringe. The process of operating an automation system further comprising the step of disengaging the syringe from the vial adapter assembly.

The process may further include the steps of connecting the syringe containing the medicament to a container, and injecting the medicament into the container. The process may further include the step of reconstituting a lyopholized medicament contained in the loaded vial. The reconstituting step may include the steps of injecting a dilutent into the vial containing the lyopholized medicament; and agitating the vial containing the lyopholized medicament to dissolve the lyopholized medicament.

The invention will be explained in greater detail below in descriptions of preferred embodiments and referring to the attached figures.

BRIEF DESCRIPTION OF THE DRAWINGS

In the following, the preferred embodiments of invention will be described in detail with reference to the following attached figures.

DETAILED DESCRIPTION

Figure 1:
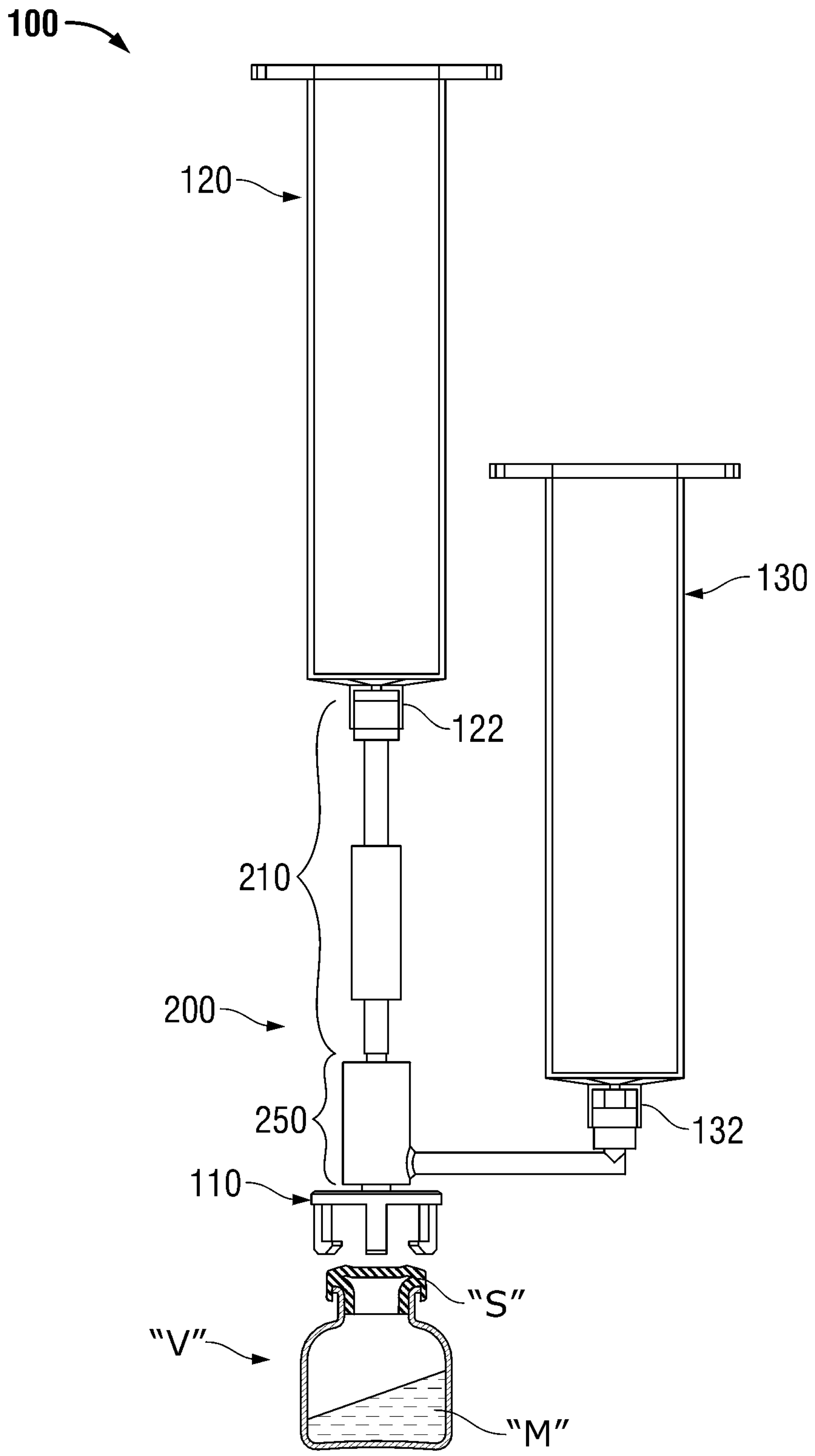
FIG. 1 is a side, elevational view of a medicament transport system in accordance with an embodiment of the present disclosure.

Referring now to the drawings and, more particularly to FIGS. 1-9, wherein like numbers identify like elements, a medicament transport system, according to an embodiment of the present disclosure, is generally designated as 100. Medicament transport system 100 is configured for selective use with a vial "V" containing a hazardous material "M", such as, for example, a cytotoxin. The hazardous material may be in a freeze dried or powdered form suitable to be readily dissolved by a diluent (e.g., saline) to form an injectable liquid solution containing the hazardous material. As used herein, the term "fluid" is understood to include both gases (e.g., air or the like) and liquids (e.g., saline, water, etc.).

Vial "V" may be fabricated from plastic or glass and may include an exteriorly headed neck defining an open end. Vial "V" typically includes an elastomeric stopper "S" configured for a pressure sealed insertion and closure of the open end of vial "V".

Figure 2:
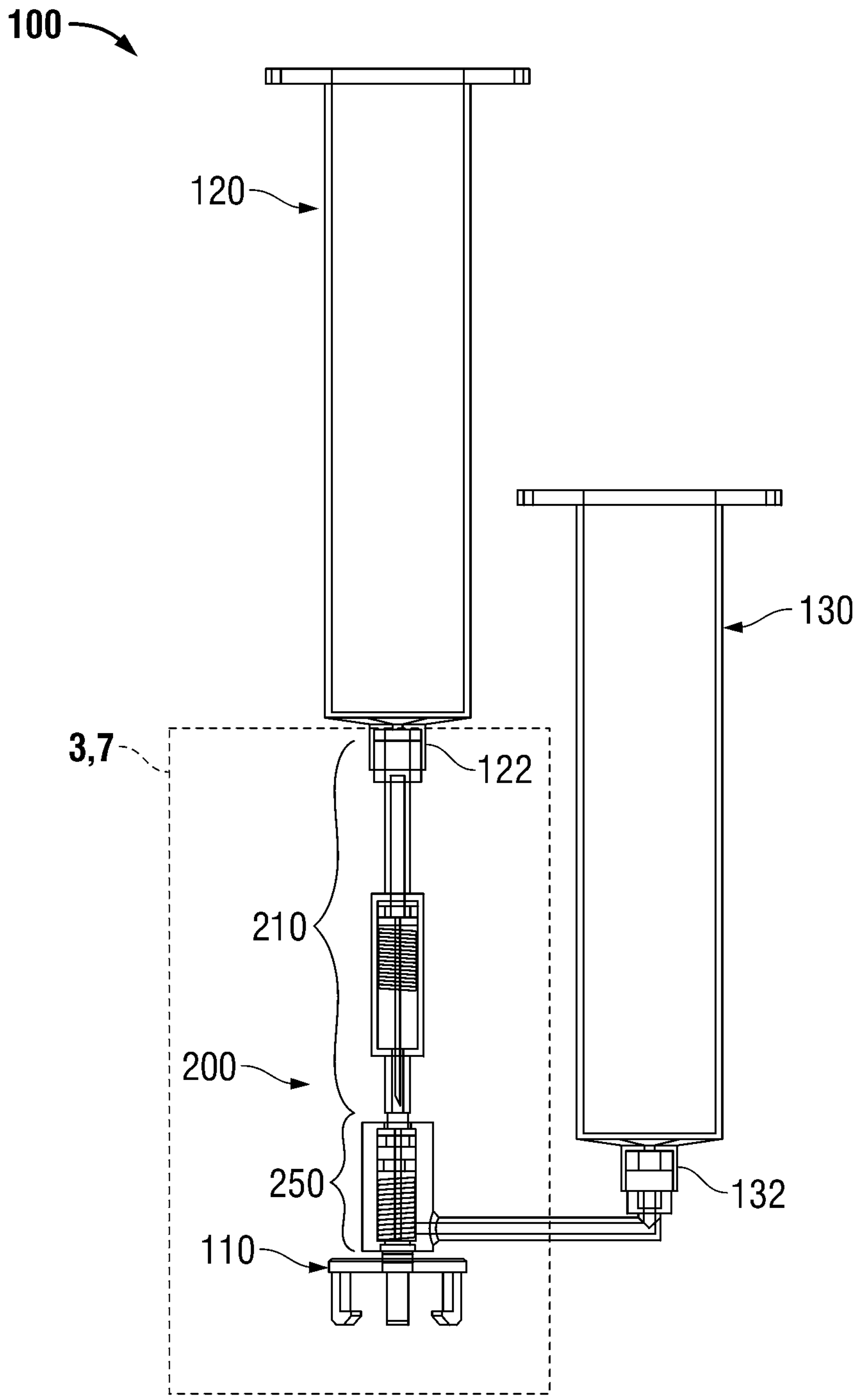
FIG. 2 is a longitudinal, cross-sectional view of the medicament transport system of FIG. 1, shown in a first condition.

As seen in FIGS. 1 and 2, medicament transport system 100 includes a control system 200, a vial connector 110 configured for fixed or selective connection to control system 200, first vessel 120 in the form of a syringe configured for selective fluid connection to a syringe adapter assembly of control system 200, and a second vessel 130 in the form of a syringe configured for selective fluid connection to a transfer adapter assembly of control system 200.

Figure 3:
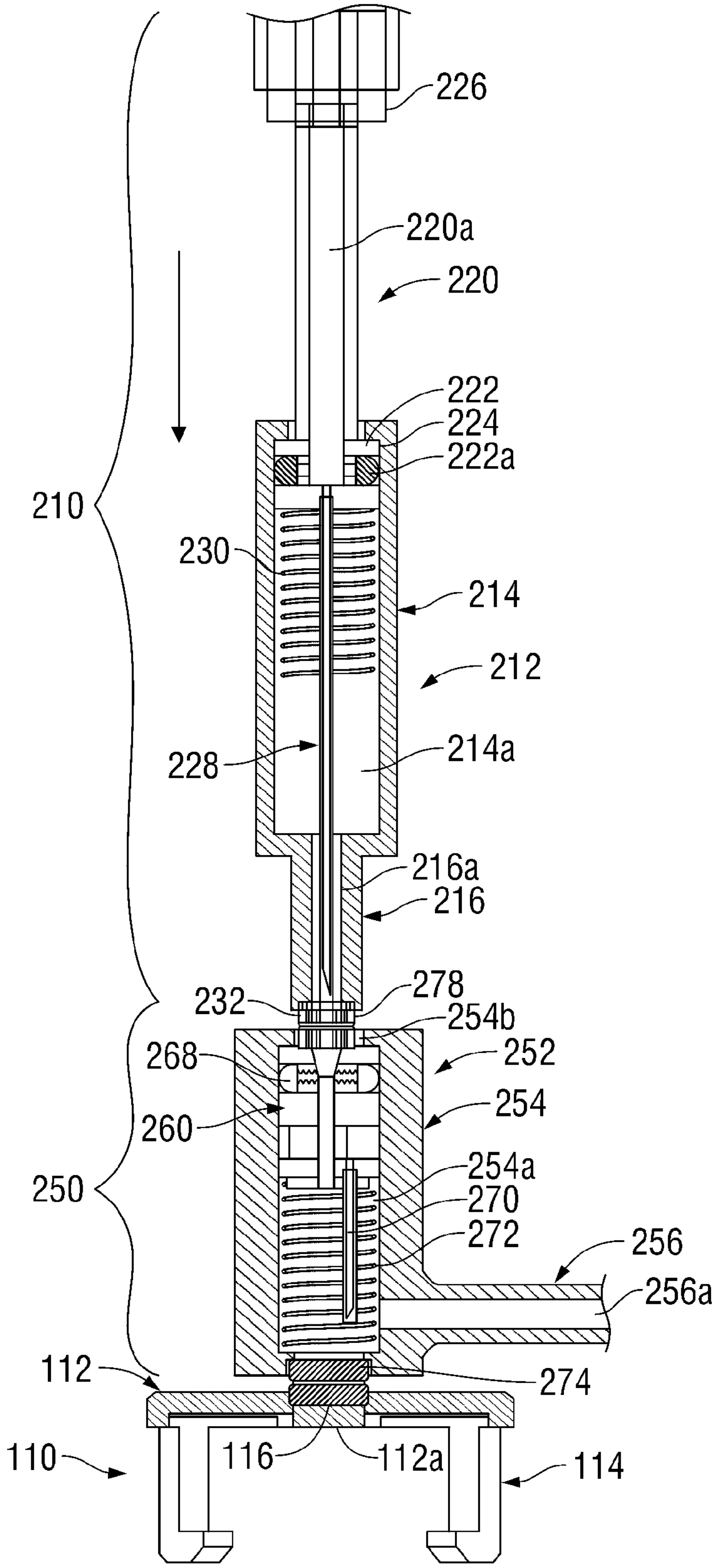
FIG. 3 is an enlarged view of the indicated area of detail of FIG. 2.
Figure 4:
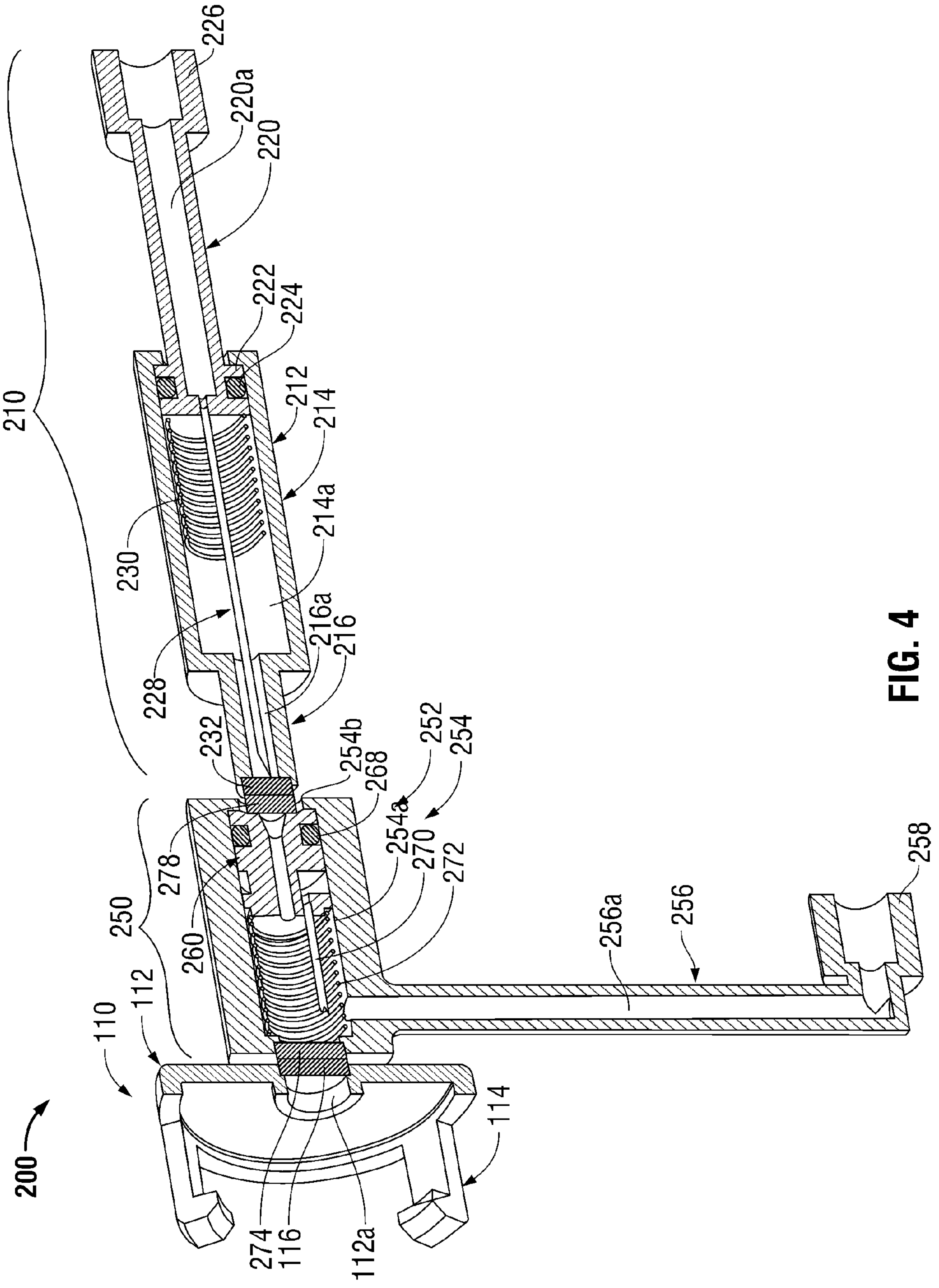
FIG. 4 is a cross-sectional, perspective view of a valve system of the medicament transport system of FIGS. 1-4.
Figure 5:
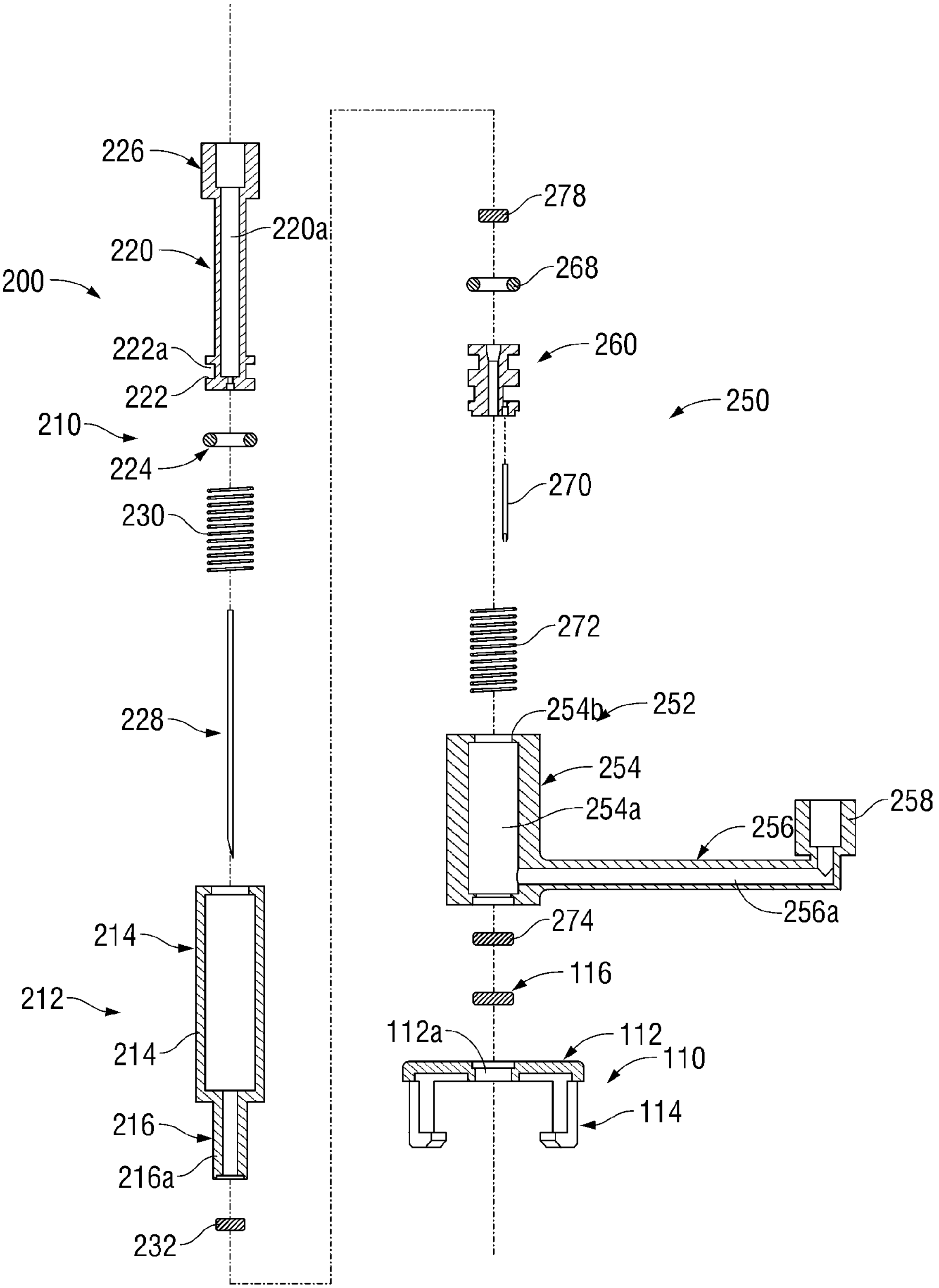
FIG. 5 is a side, elevational view, with parts separated, of the valve system of FIGS. 1-4.
Figure 6:
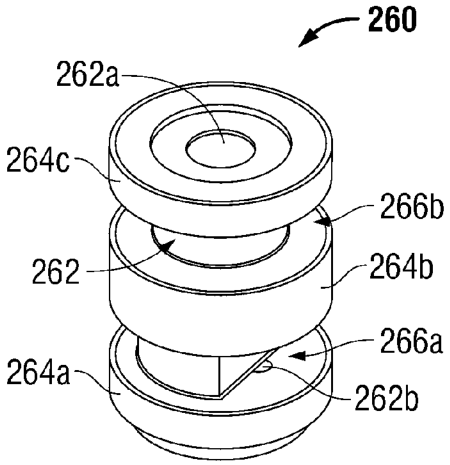
FIG. 6 is a top, perspective view of a shuttle valve of the valve system of FIGS. 4 and 5.
Figure 7:
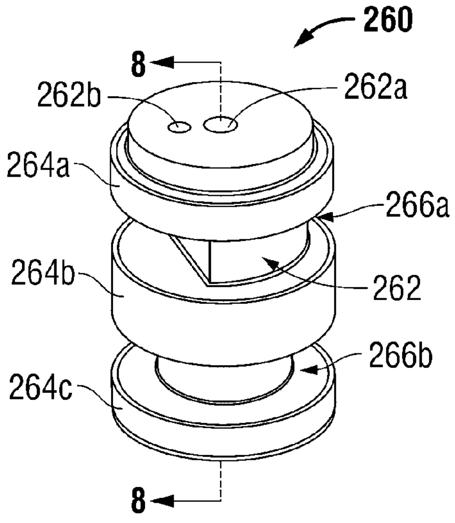
FIG. 7 is a bottom, perspective view of the shuttle valve of FIG. 6.
Figure 8:
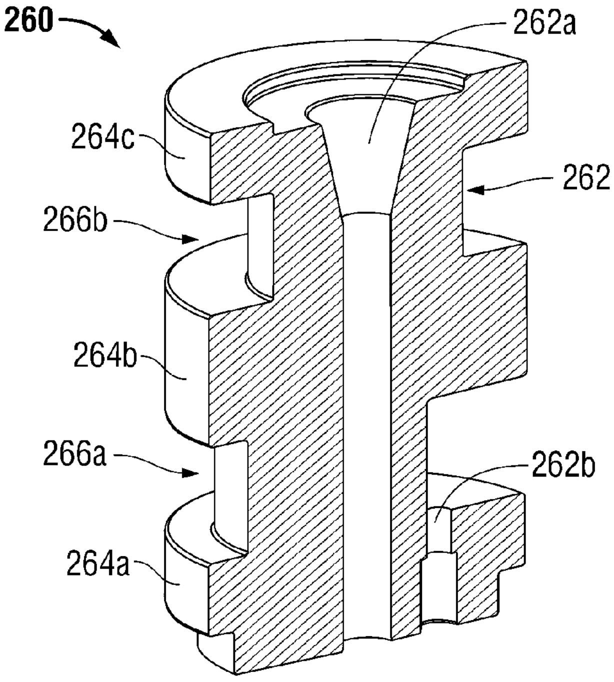
FIG. 8 is a cross-sectional view of the shuttle valve of FIGS. 6 and 7, as taken through 8-8 of FIG. 7.

As best seen in FIGS. 3-5, vial connector 110 includes a circular base 112 defining a central aperture 112*a* and having at least a pair of retainers, in the form of claws 114 extending from a side edge of base 112 and being configured to selectively engage the beaded neck of vial "V". Vial adapter 110 includes a seal member 116 disposed or seated within central aperture 112*a*. Seal member 116 may be in the form of an elastomeric gasket, washer, plug or stopper.

Referring now to FIGS. 1-9, a detailed discussion of the construction and operation of medicament transport system 100 is provided. As seen in FIGS. 1-9, control system 200 of medicament transport system 100 includes a syringe adapter assembly 210 configured for connection to a fitting 122 of first syringe 120, a vial adapter assembly 250 configured for connection to syringe adapter assembly 210, to a fitting 132 of second syringe 130, and to central aperture 112*a* of vial connector 110.

Syringe adapter assembly 210 includes a tubular syringe adapter sleeve 212 having a body portion 214 defining a cavity 214*a* of a first diameter, and a nose portion 216 defining a cavity 216*a* of a second diameter.

Syringe adapter assembly 210 includes a syringe adapter plunger 220 having a first end slidably disposed within cavity 214*a* of body portion 214 of adapter sleeve 212. The first end of adapter plunger 220 supports a head member 222 thereon having a diameter equal to or less than first diameter of cavity 214*a* of body portion 214 of adapter sleeve 212. Head member 222 defines an annular race 222*a* and supports a seal member 224 therein. Seal member 224 is selected and dimensioned to create a fluid tight seal with the wall of cavity 214*a* of body portion 214. Seal member 224 may be in the form of an O-ring, gasket or other elastomeric member.

Plunger 220 includes a second end extending out of cavity 214*a* of body portion 214 of adapter sleeve 212 and supporting a connector member 226 thereon. Connector member 226 is configured and adapted to selectively engage fitting 122 of first syringe 120. Connector member 226 of plunger 220 and fitting 122 of first syringe 120 may be in the form of a Luer-type connection.

Plunger 220 defines a lumen 220*a* therethrough. Plunger 220 is configured to support a syringe adapter needle 228 on head member 222 so as to establish a fluid communication between first syringe 120 and syringe adapter needle 228. Syringe adapter assembly 210 further includes a biasing member 230 disposed within cavity 214*a* of body portion 214 of adapter sleeve 212 at a location distal of head member 222. Biasing member 230 may be in the form of a compression spring or the like. Syringe adapter assembly 210 further includes a seal member 232 disposed within cavity 216*a* of nose portion 216 of adapter sleeve 212. Seal member 232 is selected and dimensioned to create a fluid tight seal with the wall of cavity 216*a* of nose portion 216 and to create a fluid tight seal with syringe adapter needle 228. Seal member 232 may be in the form of elastomeric gasket, washer, plug or stopper.

Figure 9:
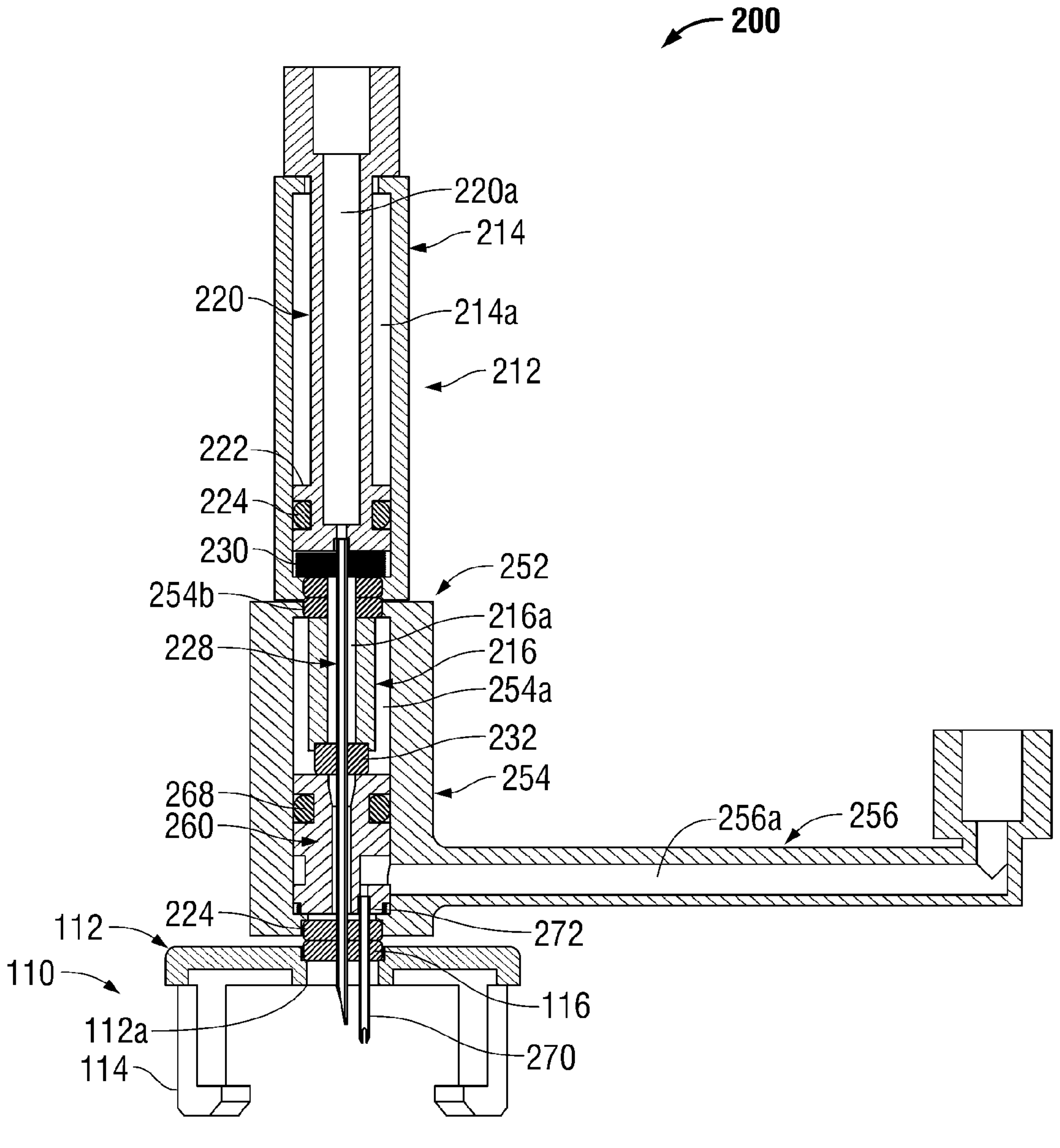
FIG. 9 is an enlarged view of the indicated area of detail of FIG. 2, illustrating the medicament transport system in a second condition.

Cavity 214*a* of body portion 214 and cavity 216*a* of nose portion 216 of adapter sleeve 212 have a combined length that is substantially equal to a length of syringe adapter needle 228 when plunger 220 is at a fully retracted or proximal-most position relative to adapter sleeve 212. Thus, syringe adapter assembly 210 has a first configuration, as seen in FIGS. 1-4, where plunger 220 is at the fully retracted position, relative to adapter sleeve 212, wherein syringe adapter needle 212 is fully contained or sheathed within cavity 214*a* of body portion 214 and cavity 216*a* of nose portion 216, and biasing member 230 is unbiased. As seen in FIG. 9, syringe adapter assembly 210 has at least a second configuration where plunger 220 is fully advanced to a distal-most position, relative to adapter sleeve 212, wherein syringe adapter needle 212 is extended from within cavity 214*a* of body portion 214 and cavity 216*a* of nose portion 216, and biasing member 230 is compressed or biased.

With continued reference to FIGS. 1-9, vial adapter assembly 250 includes a tubular transfer adapter sleeve 252 having a body portion 254 defining a cavity 254*a*, and an arm portion 256 extending from body portion 254 and defining a lumen 256*a* therethrough. Vial adapter assembly 250 includes a connector member 258 supported on a free end of arm portion 256. Connector member 258 is configured and adapted to selectively engage fitting 132 of second syringe 130. Connector member 258 of vial adapter assembly 250 and fitting 132 of second syringe 130 may be in the form of a Luer-type connection.

Body portion 254 of transfer adapter sleeve 252 defines a proximal opening 254*b* configured and dimensioned to slidably receive nose portion 216 of syringe adapter assembly 210. Vial adapter assembly 250 further includes a seal member 278 disposed within proximal opening 254*b* of transfer adapter sleeve 252. Seal member 278 is selected and dimensioned to create a fluid tight seal with the outer wall of nose portion 216 as nose portion 216 is advanced into cavity 254*a* of body portion 254. Seal member 278 may be in the form of an elastomeric gasket, washer, plug or stopper.

Vial adapter assembly 250 includes a shuttle valve 260 slidably disposed within cavity 254*a* of body portion 254. As seen in FIGS. 2-9, and more particularly FIGS. 6-8, shuttle valve 260 includes a central body portion 262 defining a central lumen 262*a* therethrough. Shuttle valve 260 includes at least three spaced apart annular flanges 264*a*-264*c* defining a pair of annular races 266*a*, 266*b* therebetween. Shuttle valve 260 defines an offset lumen 262*b* formed through distal-most annular flange 264*a* to be in fluid communication with distal annular race 266*a* of shuttle valve 260. Proximal annular race 266*b* supports a seal member 268 therein. Seal member 268 is selected and dimensioned to create a fluid tight seal with the wall of cavity 254*a* of body portion 254. Seal member 268 may be in the form of an O-ring, gasket or other elastomeric member.

Shuttle valve 260 is configured to support a transfer adapter needle 270 in offset lumen 262*b* so as to be in fluid communication with distal annular race 266*a*. Transfer adapter assembly 250 further includes a biasing member 272 disposed within cavity 254*a* of body portion 254 at a location distal of shuttle valve 260. Biasing member 272 may be in the form of a compression spring or the like.

Vial adapter assembly 250 further includes a distal seal member 274 disposed at a distal end of cavity 254*a* of body portion 254, and a proximal seal member 276 disposed at a proximal end of cavity 254*a* of body portion 254. Seal members 274, 276 are selected and dimensioned to create a fluid tight seal with body portion 254 and to create a fluid tight seal with syringe adapter needle 228 and/or transfer adapter needle 270. Seal members 274, 276 may be in the form of elastomeric gaskets, washers, plugs or stoppers.

Cavity 254*a* of body portion 254 has a length that is substantially equal to a length of shuttle valve 260 and transfer adapter needle 270 when shuttle valve 260 is at a fully retracted or proximal-most position relative to body portion 254. Thus, vial adapter assembly 250 has a first configuration, as seen in FIGS. 2-4, where shuttle valve 260 is at the fully retracted position, relative to body portion 254, wherein transfer adapter needle 270 is fully contained or sheathed within cavity 254*a* of body portion 254 and biasing member 272 is unbiased. As seen in FIG. 9, vial adapter assembly 250 has at least a second configuration where shuttle valve 260 is fully advanced to a distal-most position, relative to body portion 254, wherein transfer adapter needle 270 is extended from within cavity 254*a* of body portion 254, biasing member 272 is compressed or biased, and distal annular race 266*a* of shuttle valve 260 is in fluid communication with lumen 256*a* of arm portion 256.

Referring now to FIGS. 1-4 and 9, a method of using and operating medicament transport system 100 is shown and described below. At an initial stage, vial "A," containing a quantity of freeze dried or powdered material "M," is connected to vial connector 110, and control system 200 is connected to vial connector 100. Control system 200 is connected to vial connector 110 in the manner described above, with vial adapter assembly 250 connected to vial connector 110, with syringe adapter assembly 210 connected to vial adapter assembly 250, and with a pair of syringes 120, 130 connected to syringe adapter assembly 210 and vial adapter assembly 250, respectively. Syringe 120 contains a quantity of a diluent (e.g., saline, water, distilled water, etc.) when connected to syringe adapter assembly 210. Meanwhile, syringe 130 is empty when connected to vial adapter assembly 250.

With reference to FIGS. 3, 4 and 9, with control system 200 connected to vial adapter 100, and in particular with fitting 122 connected to connector member 226 of syringe adapter assembly 210, syringe 120 is advanced relative to adapter sleeve 212 such that syringe adapter plunger 220 is advanced distally into adapter sleeve 212. As adapter plunger 220 is advanced distally, syringe adapter needle 228 is also advanced distally and is driven through seal member 232 of syringe adapter assembly 210 and through seal member 278 of vial adapter assembly 250. Additionally, a distal end of syringe adapter needle 228 is advanced through central lumen 262*a* of shuttle valve 260. When adapter plunger 220 is fully advanced distally, biasing member 230 is compressed within cavity 214*a* of body portion 214 of adapter sleeve 212.

Concomitantly with or subsequent to the distal advancement of adapter plunger 220 relative to adapter sleeve 212, adapter sleeve 212 is advanced distally relative to body portion 254 of vial adapter assembly 250. As adapter sleeve 212 is advanced distally relative to body portion 254 of vial adapter assembly 250, nose portion 216 of adapter sleeve 212 is advanced into cavity 254*a* of body portion 254. As nose portion 216 of adapter sleeve 212 is advanced into cavity 254*a* of body portion 254, nose portion 216 acts on shuttle valve 260 to advance shuttle valve 260 through cavity 254*a* of body portion 254. The distal advancement of nose portion 216 of adapter sleeve 212 and shuttle valve 260 causes or results in distal end of syringe adapter needle 228 and the distal end of transfer adapter needle 270 to be advanced through distal seal member 274 of vial adapter assembly 250, through seal member 116 of vial connector 110, and through stopper "S" of vial "V."

When nose portion 216 of adapter sleeve 212 is fully advanced through cavity 254*a* of body portion 254, shuttle valve 260 is moved to a fully advanced position and biasing member 272 has been compressed. When shuttle valve 260 is at the fully advanced position, distal annular race 266*a* of shuttle valve 260 is in fluid communication with lumen 256*a* of arm portion 256 of vial adapter assembly 250.

As seen in FIG. 9, with the distal end of syringe adapter needle 228 and the distal end of transfer adapter needle 270 advanced into vial "V," through distal seal member 274 of vial adapter assembly 250, through seal member 116 of vial adapter 110, and through stopper "S" of vial "V," a plunger (not shown) of syringe 120 is actuated to deliver diluent into vial "V" and form an injectable liquid solution containing the hazardous material. The diluent is delivered through syringe adapter needle 228 into vial "V."

As the diluent is injected into vial "V," and vapors or gases created are forced out of or displaced out of vial "V" through transfer adapter needle 270, through distal annular race 266*a* of shuttle valve 260, and out through lumen 256*a* of arm portion 256 of vial adapter assembly 250 into syringe 130. It is contemplated that a pressure differential or vacuum may be created by syringe 130, by withdrawing a plunger thereof (not shown) prior to or concomitantly with the advancement of the plunger of syringe 120. Such a vacuum will thus draw any vapors or gases into syringe 130 and prohibit the egress of vial contents to ambient.

Following the injection of the diluent and the formation of the injectable liquid solution, syringe 120 is withdrawn relative to vial adapter assembly 250 such that plunger 220 is withdrawn relative to body portion 214 of syringe adapter assembly 210. As plunger 220 is withdrawn, syringe adapter needle 228 is withdrawn into nose portion 216. Alternatively, any distal forces used to advance plunger 220 relative to body portion 214 may be removed, thereby allowing biasing member 230 to expand and thus automatically withdraw plunger 220 relative to body portion 214.

With plunger 220 withdrawn relative to body portion 214, syringe adapter assembly 210 is disconnected from vial adapter assembly 250. During disconnection of syringe adapter assembly 210, nose portion 216 of syringe adapter assembly 210 is withdrawn from vial adapter assembly 250. As syringe adapter assembly 210 is withdrawn from vial adapter assembly 250, biasing member 272 is permitted to expand and thus withdraw shuttle valve 260 and syringe transfer needle 270 back into syringe adapter assembly 210.

While the above described medicament transport system 100 has been described hereinabove as a manually operated system, it is contemplated, and within the scope of the present disclosure, that medicament transport system 100 may be incorporated into an automated medicament preparation system, such as, for example, in an automated system substantially similar to the system disclosed and described in U.S. Pat. No. 6,915,823 to Osborne et al., the entire content of which is incorporated herein by reference.

In addition to the method of creating the pressure differential described above, various other systems and methods of creating a pressure differential between syringe 120 and syringe 130 are contemplated and disclosed hereinbelow.

Figure 10:
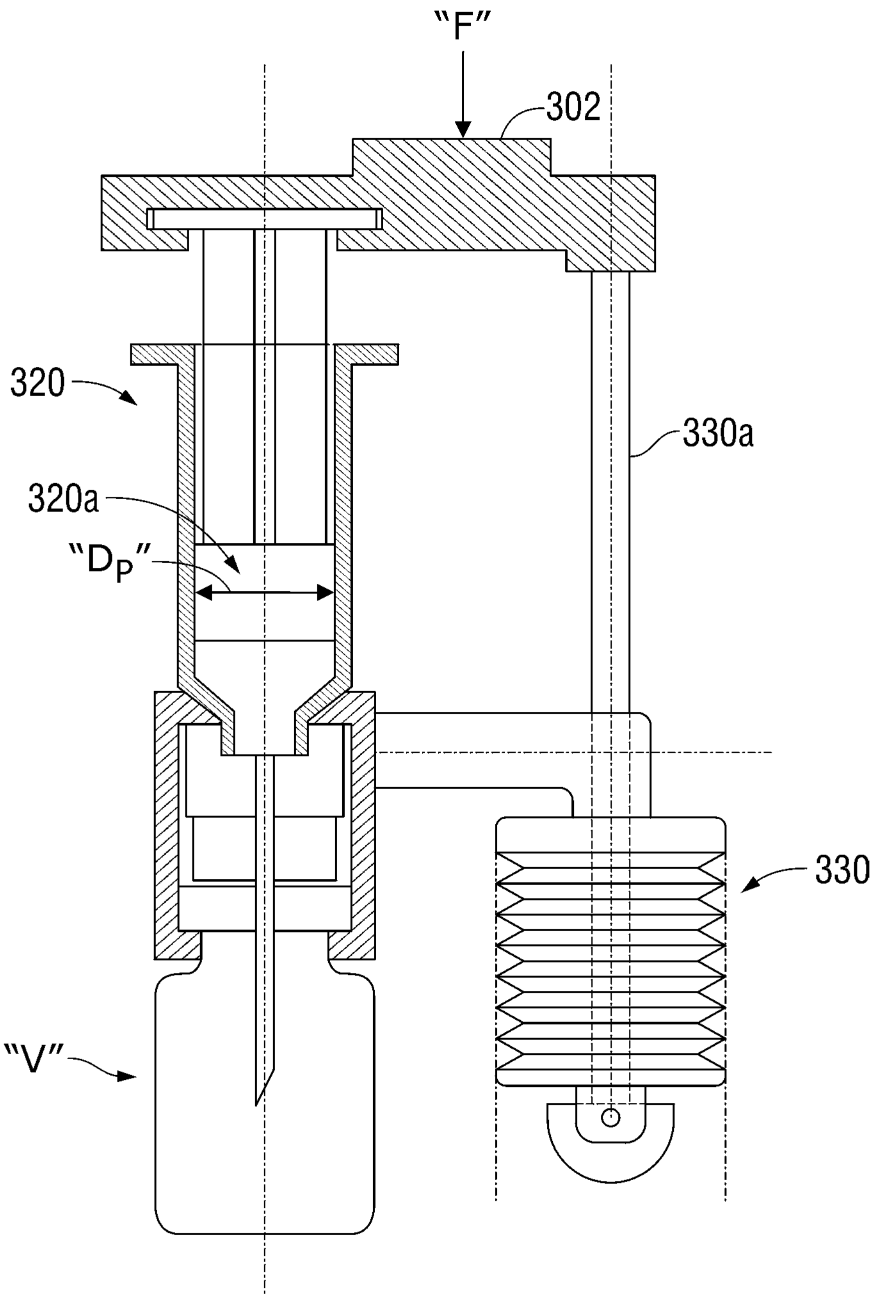
FIG. 10 is a schematic illustration of a medicament transport system according to another embodiment of the present disclosure.

Turning now to FIG. 10, a medicament transport system according to another embodiment of the present disclosure is generally designated as 300. As seen in FIG. 10, medicament transport system 300 includes a linkage, in the form of a cross-member, 302 interconnecting a syringe 320 and an expansion chamber 330. Cross-member 302 interconnects a plunger 320*a* of syringe 320 with a plunger 330*a* of expansion chamber 330. In this embodiment, translation of plunger 320*a* of syringe 320 is substantially equal to a translation of a surface of expansion chamber 330. The relative volumetric change between syringe 320 and expansion chamber 330 is determined using the following equation:

$$V - V_1 = \frac{x\pi(D_e^2 - D_p^2)}{4}$$

Where:

V=instantaneous control volume;

$V_1$=initial volume;

x=axial translation of plunger;

$D_e$=effective diameter of expansion chamber; and $D_p$=diameter of plunger.

Figure 11:
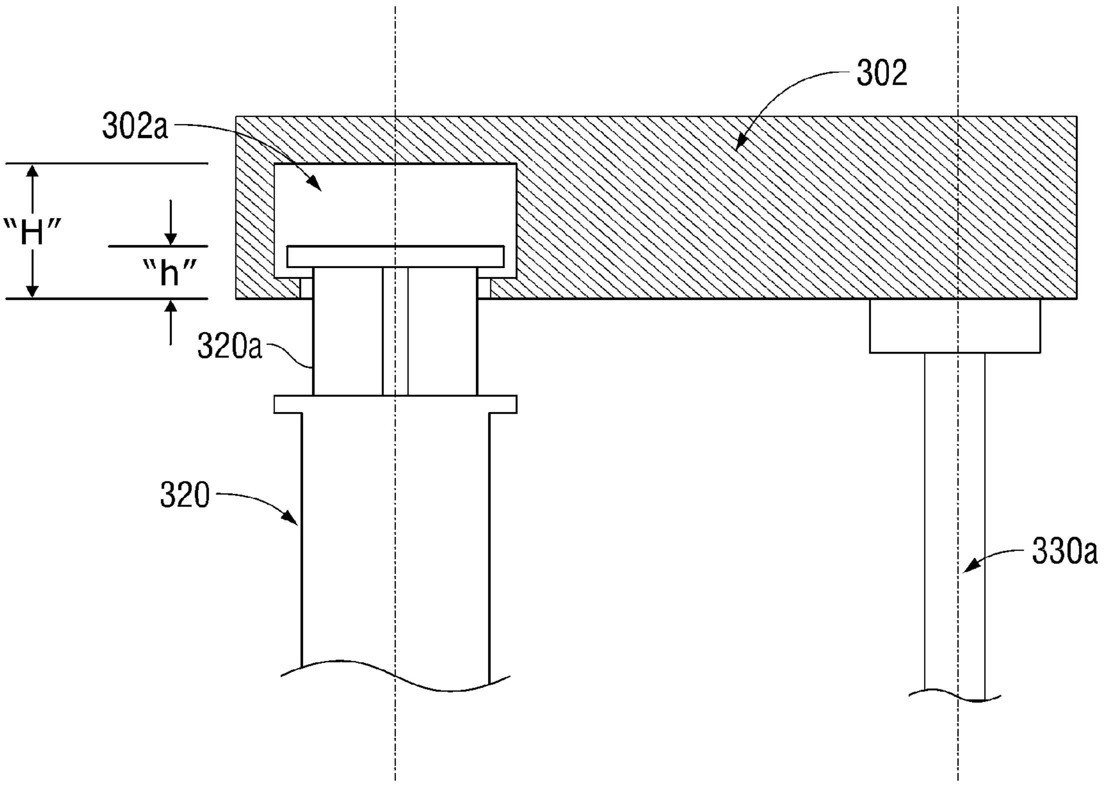
FIG. 11 is a schematic illustration of a medicament transport system according to a further embodiment of the present disclosure.

In the event that the diameters of the effective expansion chamber and the plunger are equal, then the net volume change is zero (0). When the diameter of the effective expansion chamber is greater than the diameter of the plunger, then there will be a constant increase of control volume over a given stroke. Accordingly, as seen in FIG. 11, a system and method of maintaining an initial vacuum is illustrated and includes a pocket or chamber 302*a* formed in cross-member 302 defining a height "H" and being configured to engage the plunger 320*a* of syringe 320. In this embodiment, the volumetric change is determined using the following equation:

$$V - V_1 = \frac{h\pi D_e^2}{4} + \frac{x\pi(D_e^2 - D_p^2)}{4}$$

Where:

h=height of initial offset of the plunger.

A pressure in the medicament transport system can be determined if an amount of non-compressible fluid is known as a fraction of the total volume. Assuming ideal gases, a pressure is determined using the following equation:

$$\frac{P_2}{P_1} = \frac{V_1(1-f)}{V_1(1-f) + \frac{h\pi D_e^2}{4} + \frac{x\pi(D_e^2 - D_p^2)}{4}}$$

Where:

$P_2$=instantaneous pressure at depression "x";

$P_1$=initial pressure (atmospheric pressure); and f=fraction of incompressible initial volume.

Figure 12:
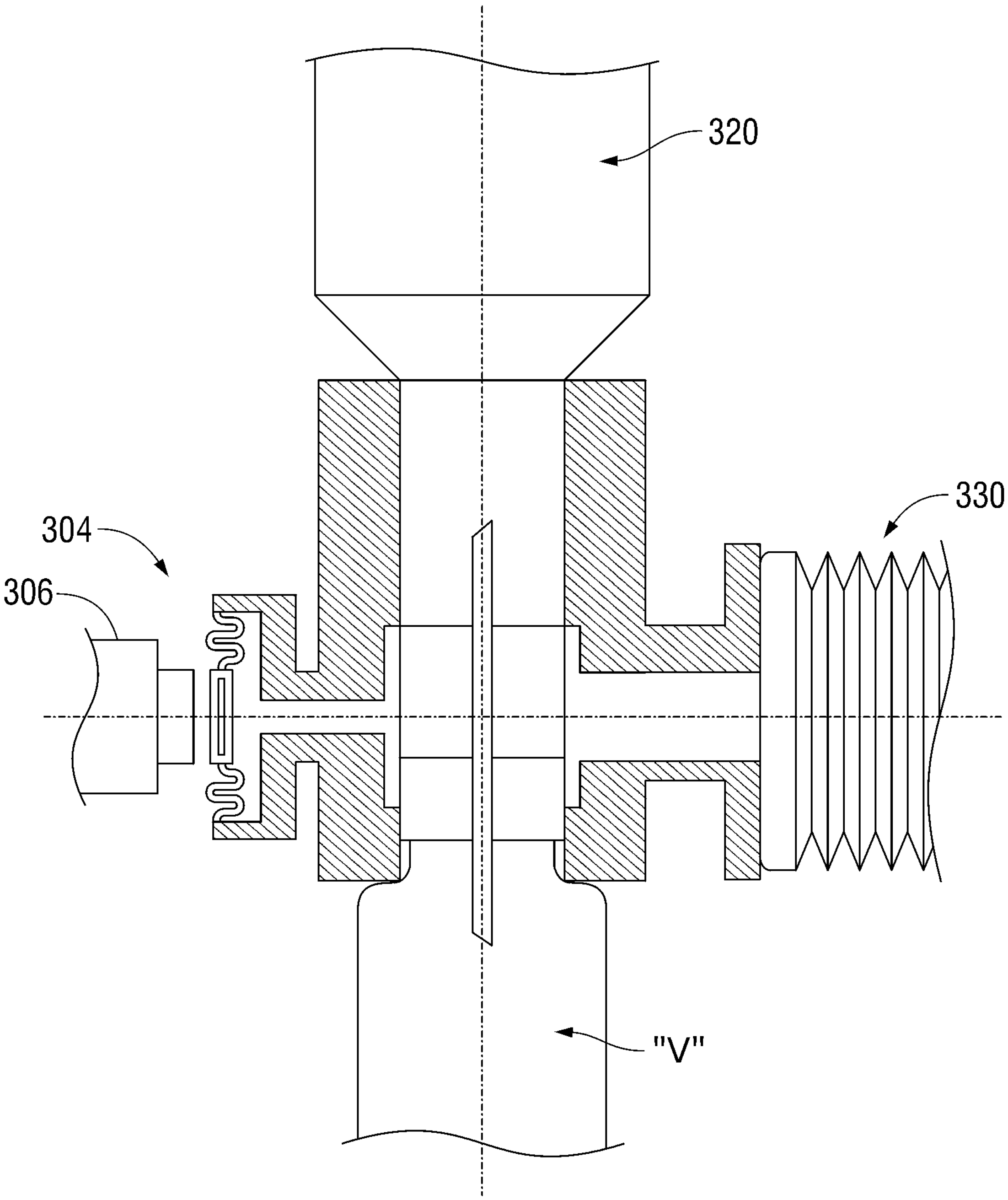
FIG. 12 is a schematic illustration of a medicament transport system according to yet another embodiment of the present disclosure.

It is contemplated that the medicament transport system will incorporate a degree of automation such that direct sensing of the pressure within the control volume may be utilized to add further control to the desired pressure differential. Accordingly, as seen in FIG. 12, a mechanically sensitive diaphragm 304 is configured and located for operative cooperation and interaction with a load cell 306. It is contemplated that a voltage from load cell 306 may be used to control a rate of volumetric change of expansion chamber 330.

In the embodiment of FIG. 12, the plunger of syringe 320 can operate independently of expansion chamber 330, wherein the signal produced by load cell 306 is used to servo drive expansion chamber 330. Load cell 306 may be coupled to diaphragm 304 in a simple way, such as, for example, by a vacuum, mechanically or magnetically. Such an arrangement will enable the system to sense when a failure has occurred, for example, during a filling procedure, if the pressure goes positive, the system can abort the instant fill, shut down the filling machine or mechanism, or otherwise take preventative or curative measures.

System 300 can also "preload" a vacuum into expansion chamber 330. For example, once system 300 is coupled, a small displacement of expansion chamber 300 can induce a vacuum into the chamber, and this new value can be set as the new basis for the filling operation. It is further contemplated that both the expansion chamber 330 and load cell 306 may be integrated.

Figure 13:
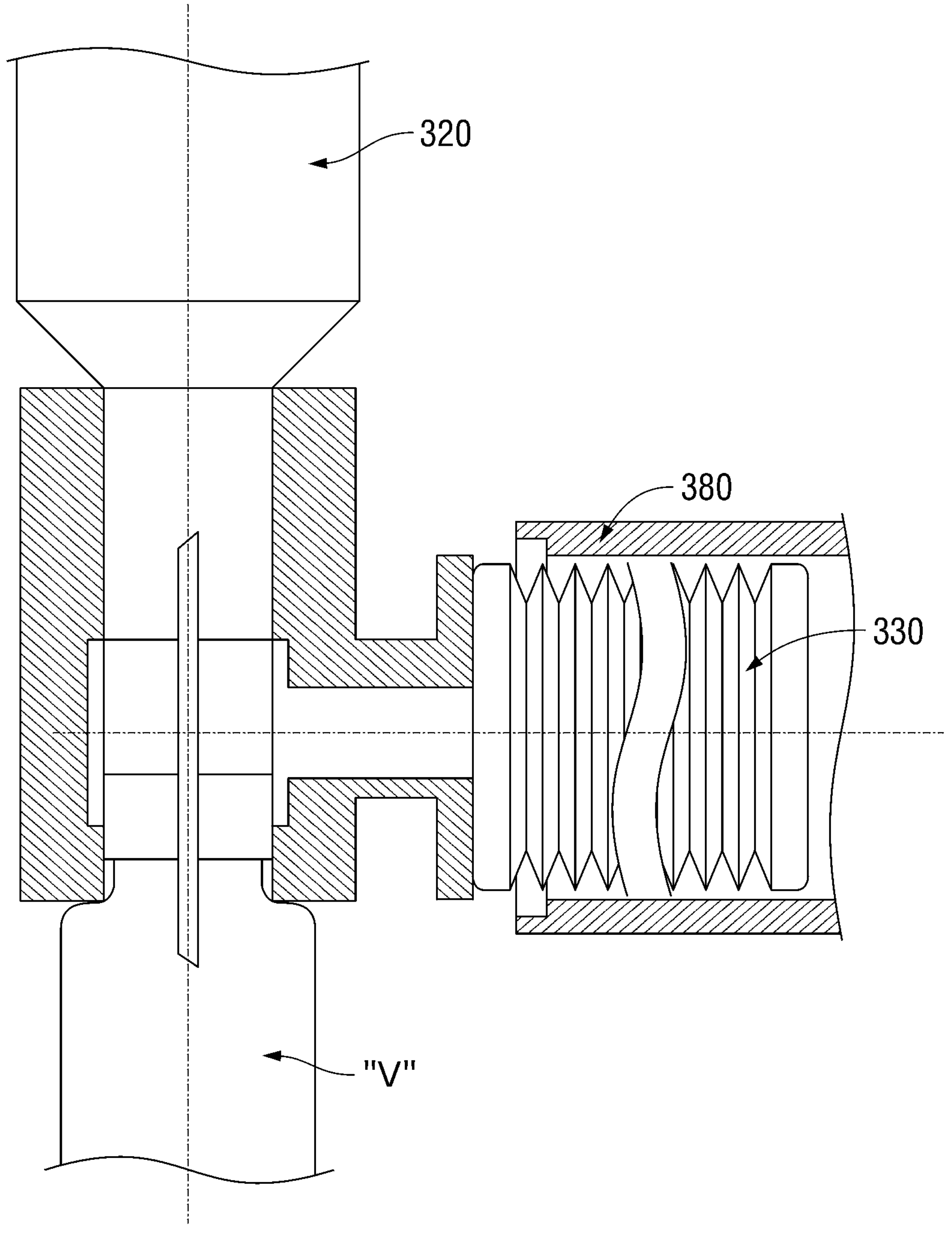
FIG. 13 is a schematic illustration of a medicament transport system according to still another embodiment of the present disclosure.
Figure 14:
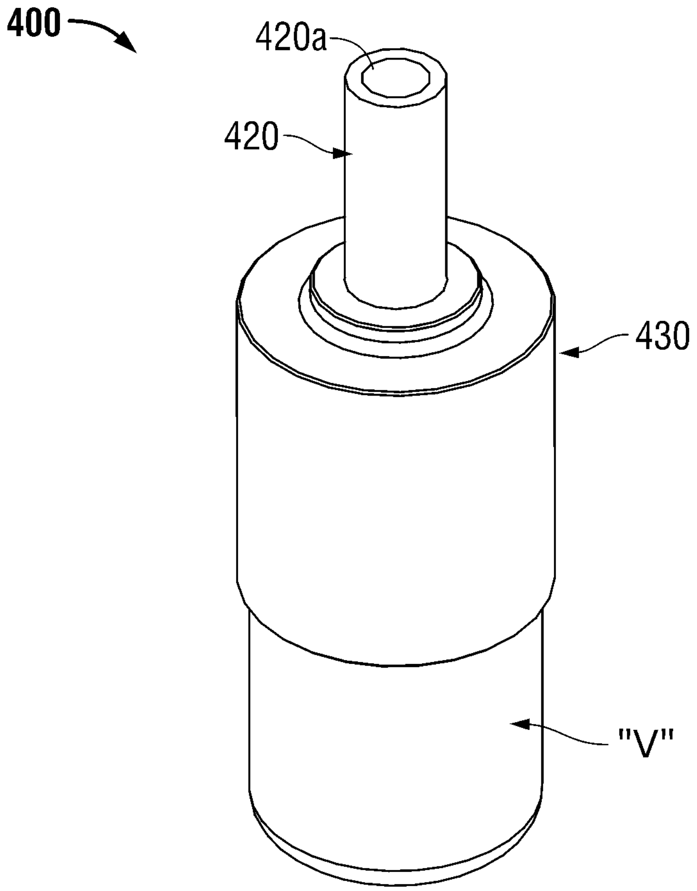
FIG. 14 is a perspective view of a medicament transport system according to yet another embodiment of the present disclosure.
Figure 15:
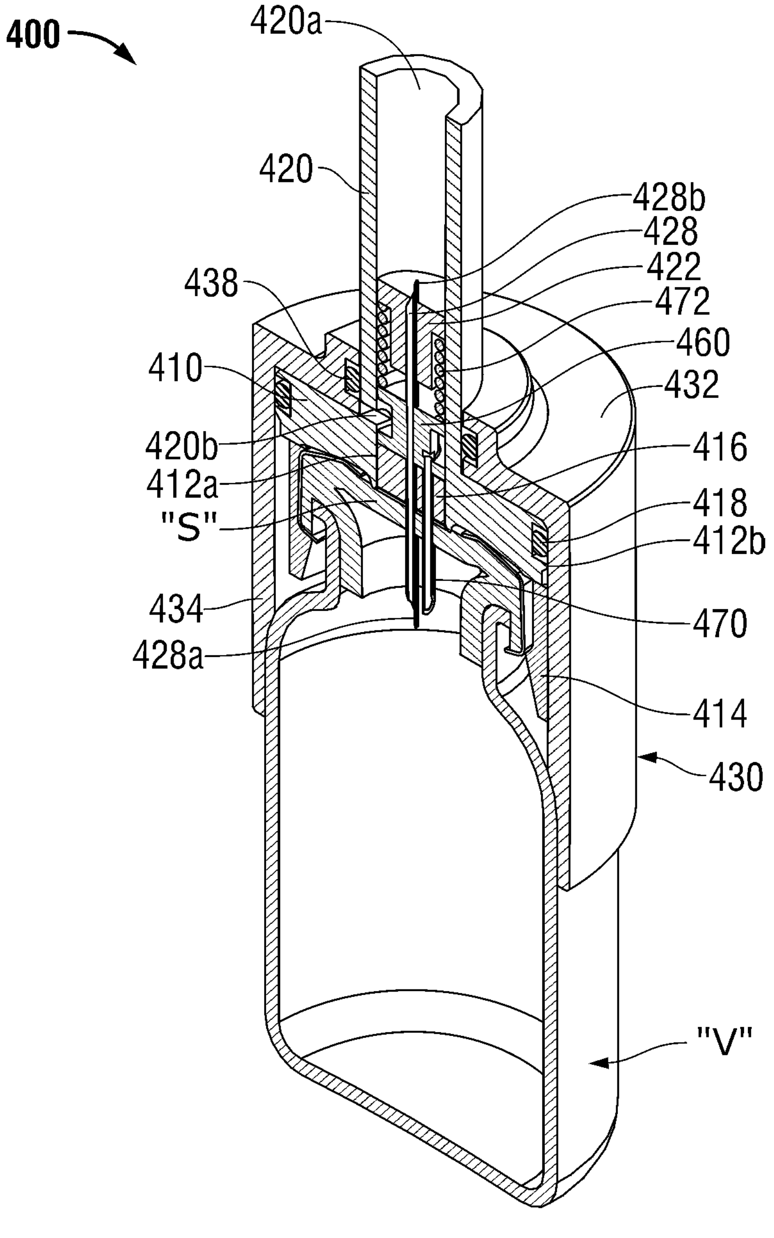
FIG. 15 is a longitudinal, cross-sectional, perspective view of the medicament transport system of FIG. 14.
Figure 16:
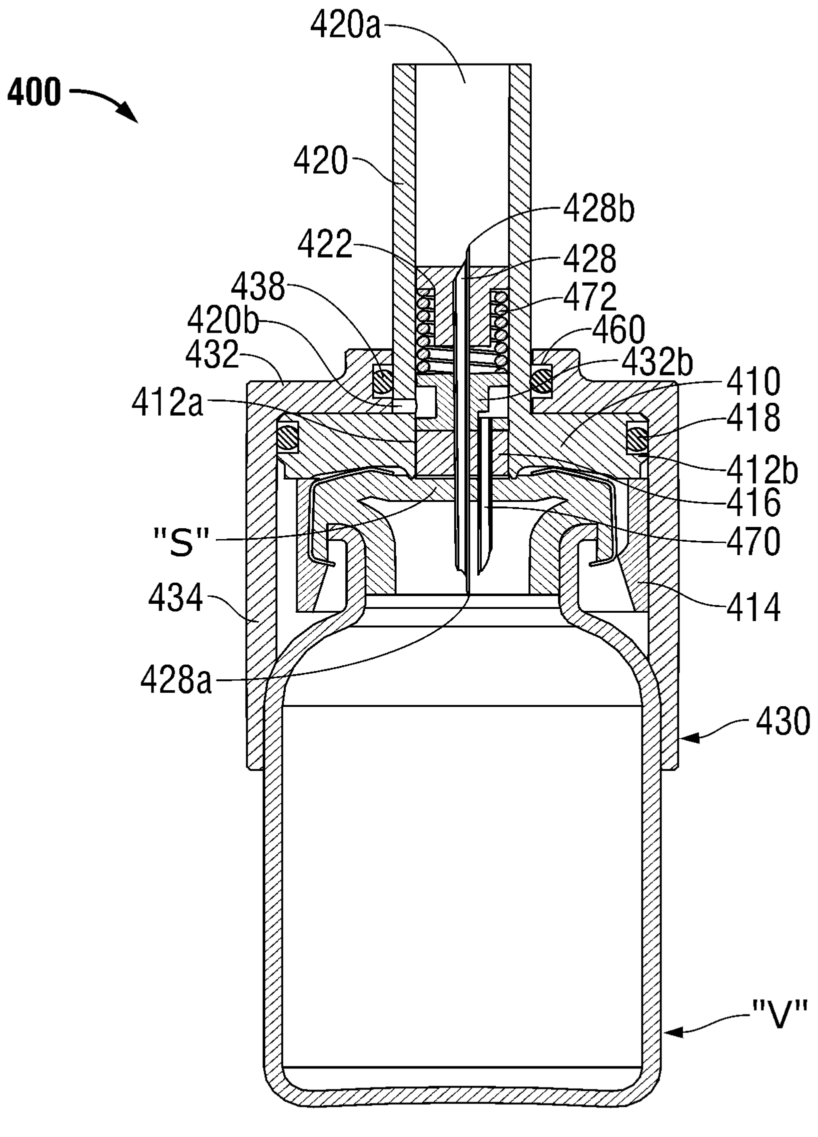
FIG. 16 is a longitudinal, cross-sectional, elevation view of the medicament transport system of FIGS. 14 and 15.
Figure 17:
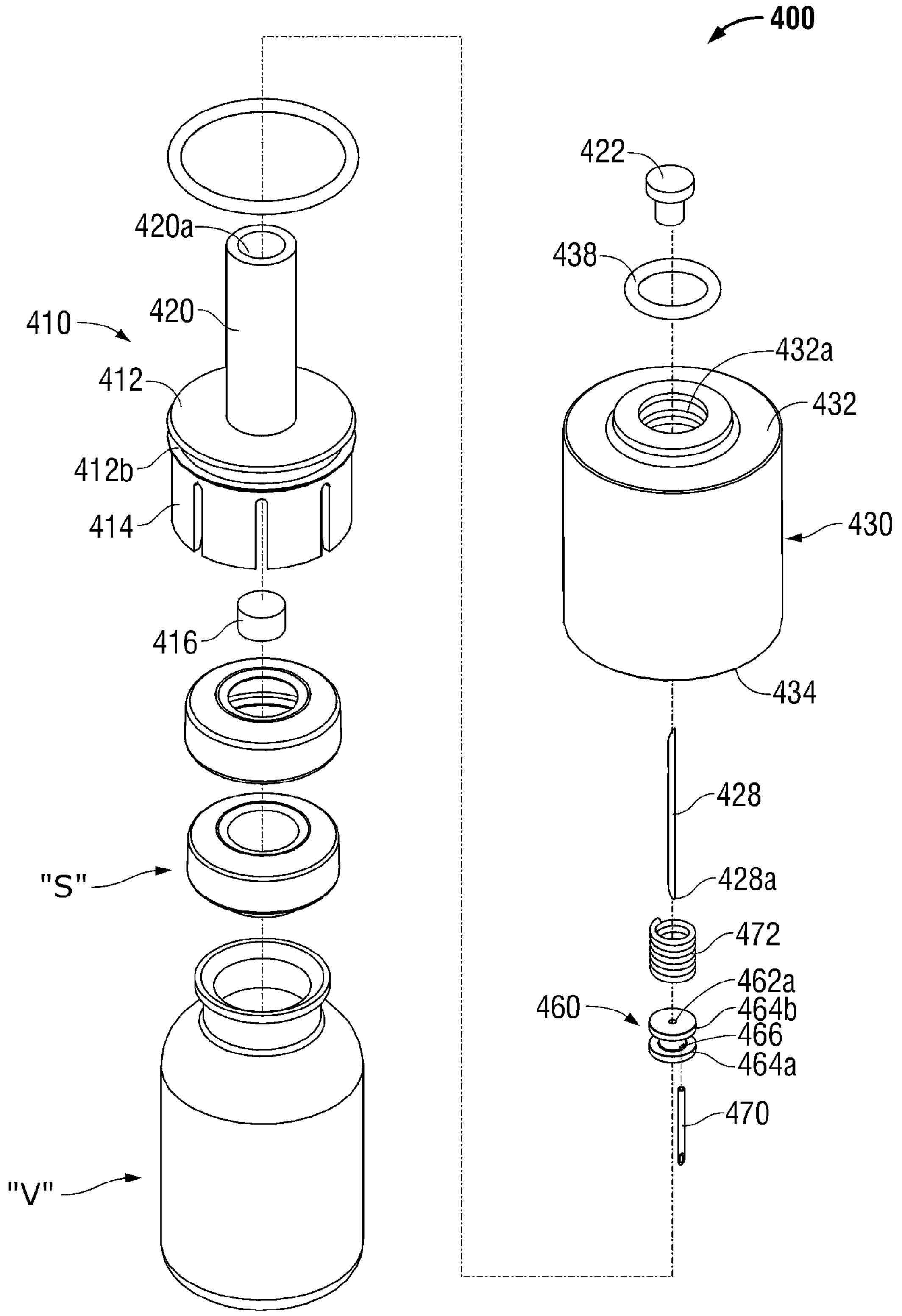
FIG. 17 is a perspective view, with parts separated, of the medicament transport system of FIGS. 14-16.
Figure 18:
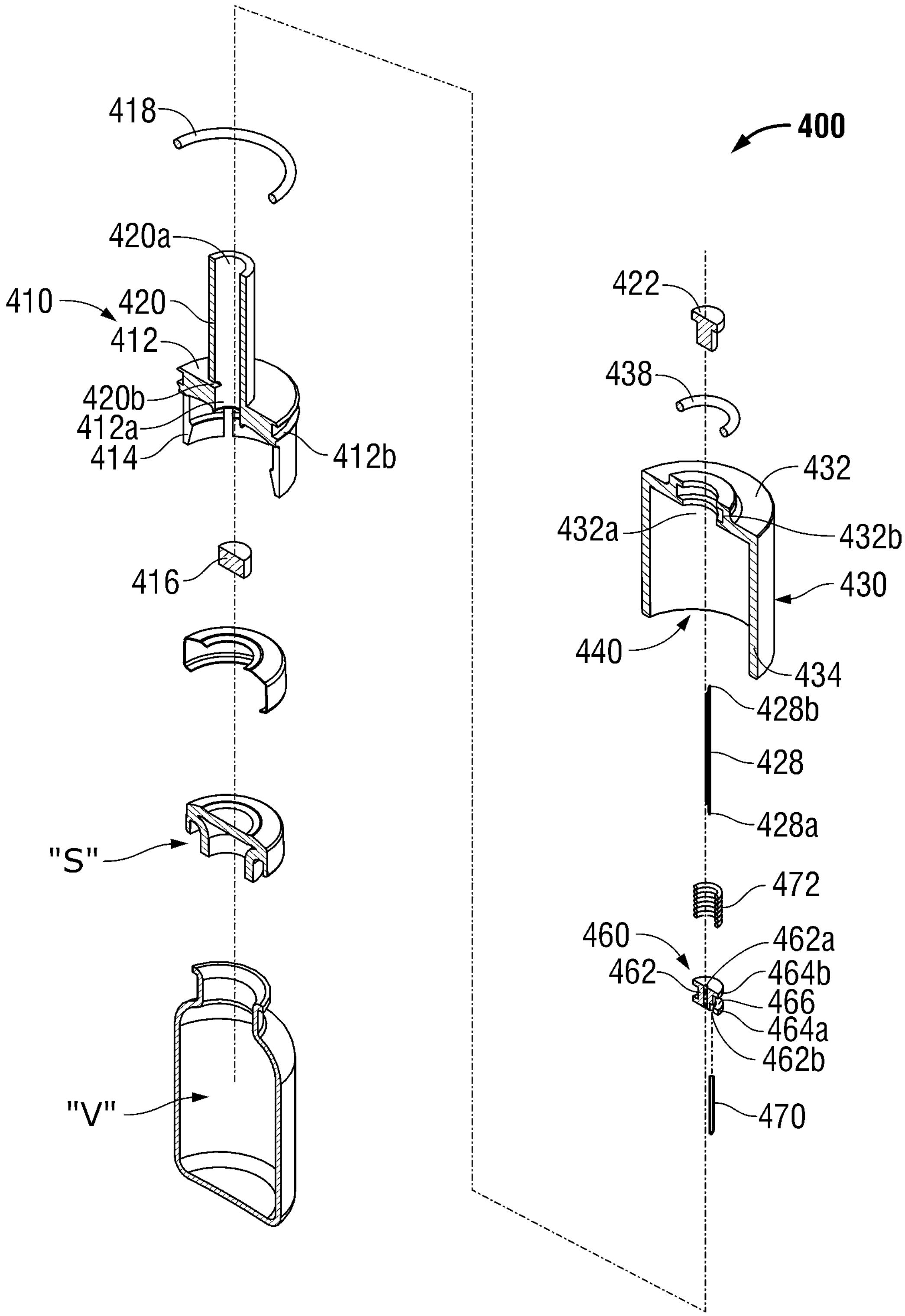
FIG. 18 is a longitudinal, cross-sectional, perspective view, with parts separated, of the medicament transport system of FIGS. 14-17.
Figure 19:
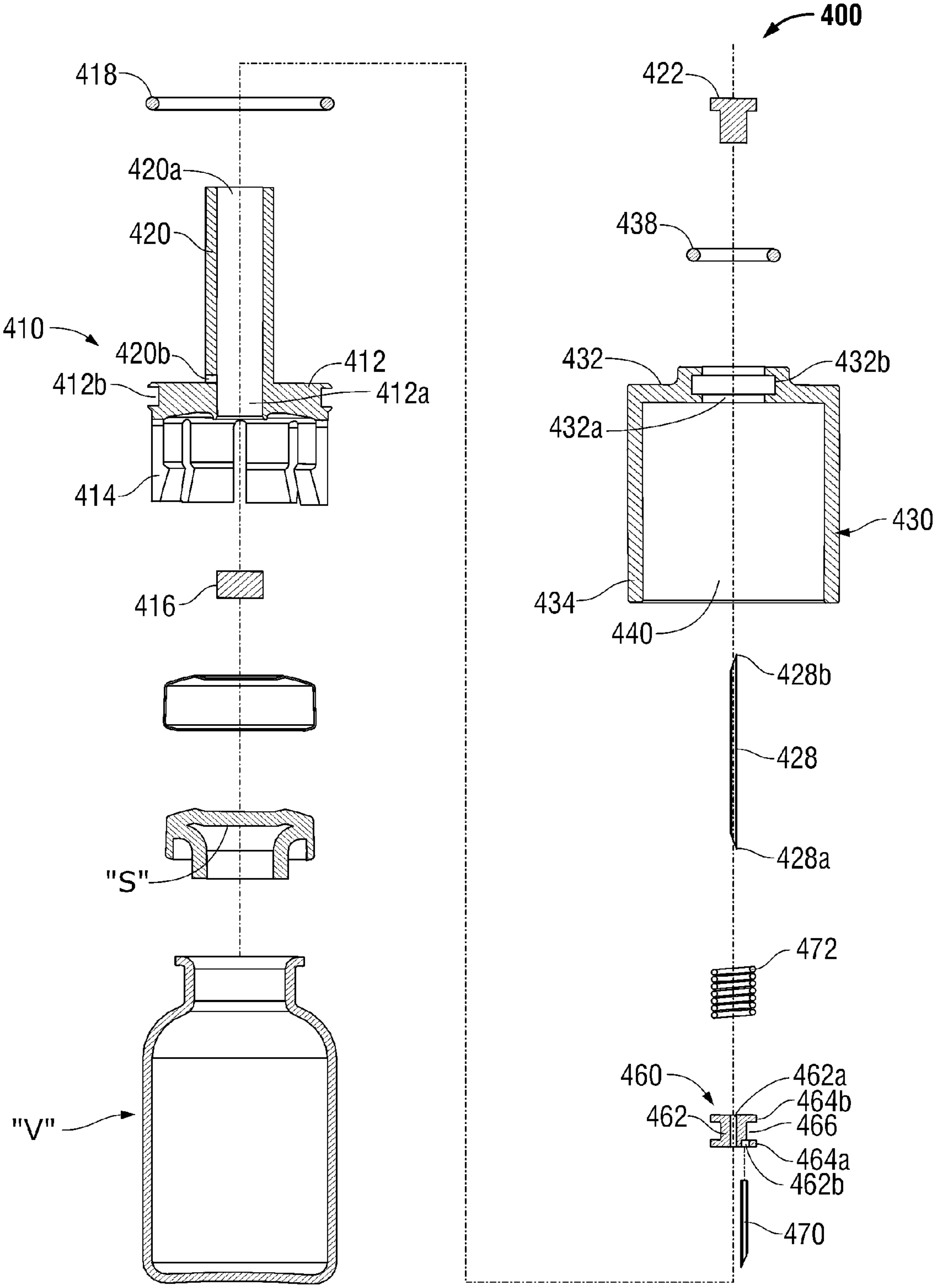
FIG. 19 is a longitudinal, cross-sectional, elevation view, with parts separated, of the medicament transport system of FIGS. 14-18.

In another embodiment, as seen in FIG. 13, in system 300, the requisite expansion of expansion chamber 330 is accomplished through the application an external vacuum thereto. As seen in FIG. 13, an external vacuum chamber 308 is provided around expansion chamber 330. In use, the contents of vacuum chamber 308 would be evacuated to cause the volumetric change to expansion chamber 330.

The embodiment of FIG. 13 will also permit the independent operation of the plunger of syringe 320 as the vacuum is applied to vacuum chamber 308 may be set to a constant value. Operation of such a system may entail introducing vacuum chamber 308 to a flange of expansion chamber 330 in a sealing-type arrangement, applying a preset vacuum to vacuum chamber 308, and displacing the plunger of syringe 320 while simultaneously maintaining the vacuum in vacuum chamber 308.

Turning now to FIGS. 14-25, a medicament transport systems according to yet another embodiment of the present disclosure, is generally designated as 400. As seen in FIGS. 14-19, medicament transport system 400 includes a vial adapter assembly 410 having a circular base 412 defining a central aperture 412*a* and having a plurality of retainers, in the form of claws 414, extending from a side edge of base 412 and being configured to selectively engage a beaded neck of a vial "V." Vial adapter assembly 410 includes a seal member 416 disposed or seated within central aperture 412*a*. Seal member 416 may be in the form of an elastomeric gasket, washer, plug or stopper.

Circular base 412 of vial adapter assembly 410 is provided with an outer annular race 412*b* for supporting a seal member 418, in the form of an O-ring, gasket or other elastomeric member, therein.

Vial adapter assembly 410 includes a stem 420 supported on and projecting from circular base 412, on a side opposite to retainers 414. Stem 420 defined a lumen 420*a* therethrough that is in fluid communication with central aperture 412*a* of central base 412. Stem 420 is provided with an aperture 420*b* formed through a wall thereof and in fluid communication with lumen 420*a*. As seen in FIGS. 15, 16, 18 and 19, aperture 420*b* is formed in close proximity to circular base 412.

Vial adapter assembly 410 further includes a needle shuttle valve 460 slidably disposed within lumen 420*a* of stem 420. Needle shuttle valve 460 is sized and constructed of a material that creates a seal between needle shuttle valve 460 and an inner wall of stem 420. Needle shuttle valve 460 includes a central body portion 462 defining a central lumen 462*a* therethrough. Needle shuttle valve 460 includes at least two spaced apart annular flanges 464*a*, 464*b* defining an annular race or groove 466 therebetween. Needle shuttle valve 460 defines an offset lumen 462*b* formed through distal-most annular flange 464*a* to be in fluid communication with annular race 466.

Needle shuttle valve 460 is configured to support a twin-tipped transfer needle 428 in central lumen 462*a* such that a first tip 428*a* of transfer needle 428 extends in a distal direction in stem 420, and a second tip 428*b* of transfer needle 428 extends in a proximal direction. Needle shuttle valve 460 further includes a vacuum needle 470 supported in offset lumen 462*b* so as to be in fluid communication with annular race 466*a*.

Vial adapter assembly 410 further includes a biasing member 472 disposed within lumen 420*a* of stem 420 at a location proximal or behind needle shuttle valve 460. Biasing member 472 may be in the form of a compression spring or the like.

Vial adapter assembly 410 further includes a seal member 422 slidably disposed in lumen 420*a* of stem 420. Seal member 422 is disposed proximal of or behind biasing member 472. Seal member 422 forms a fluid tight seal with an inner wall of stein 420.

Figure 20:
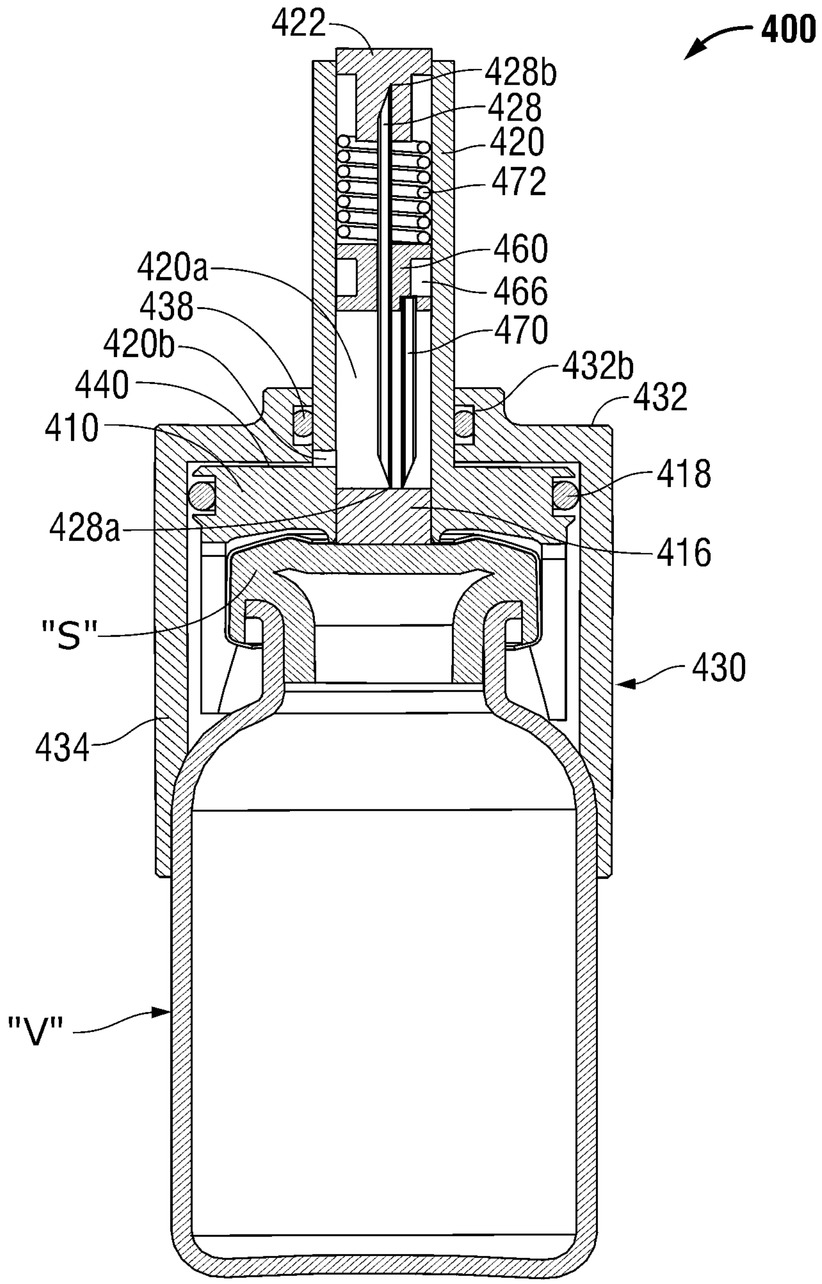
FIG. 20 is a longitudinal, cross-sectional, elevation view of the medicament transport system of FIGS. 14-19, shown in a first condition.
Figure 21:
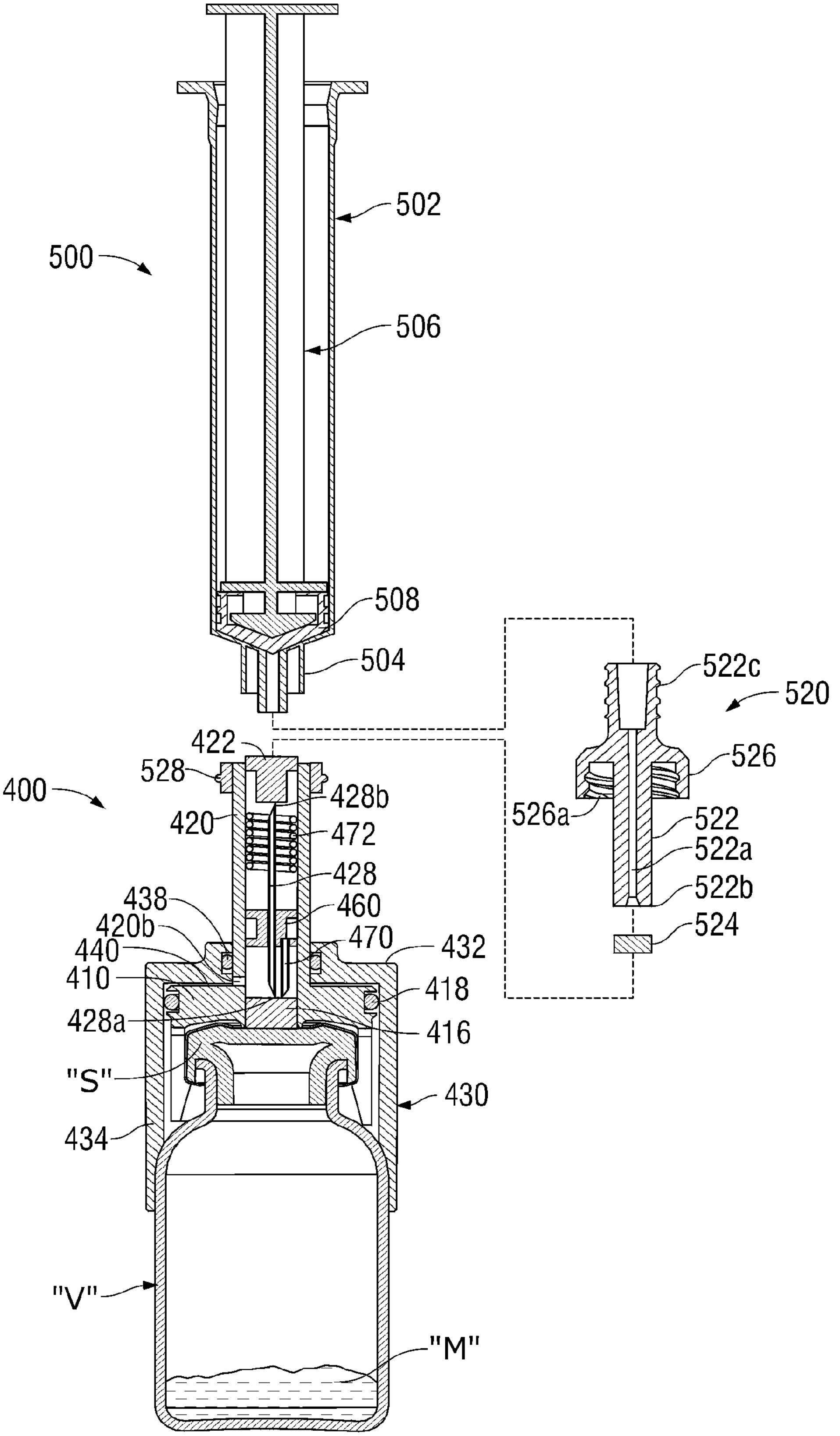
FIG. 21 is a longitudinal, cross-sectional, elevation view of the medicament transport system of FIGS. 14-20, shown in the first condition, illustrating a syringe and a syringe adapter for use therewith.

As seen in FIGS. 20 and 21, and to be described in greater detail below, vial adapter assembly 410 includes a first or unactuated condition wherein seal member 422, and needle shuttle valve 460 (including transfer needle 428 and vacuum needle 470) are located at a relatively proximal-most position within lumen 420*a* of stem 420. As so positioned, the distal tips of transfer needle 428 and vacuum needle 470 do not penetrate sealing member 416 of vial adapter 410. Also, as so positioned, biasing member 472 is may be maintained in an unbiased or uncompressed condition, or preferably in a slightly compressed or mid compressed state.

Figure 22:
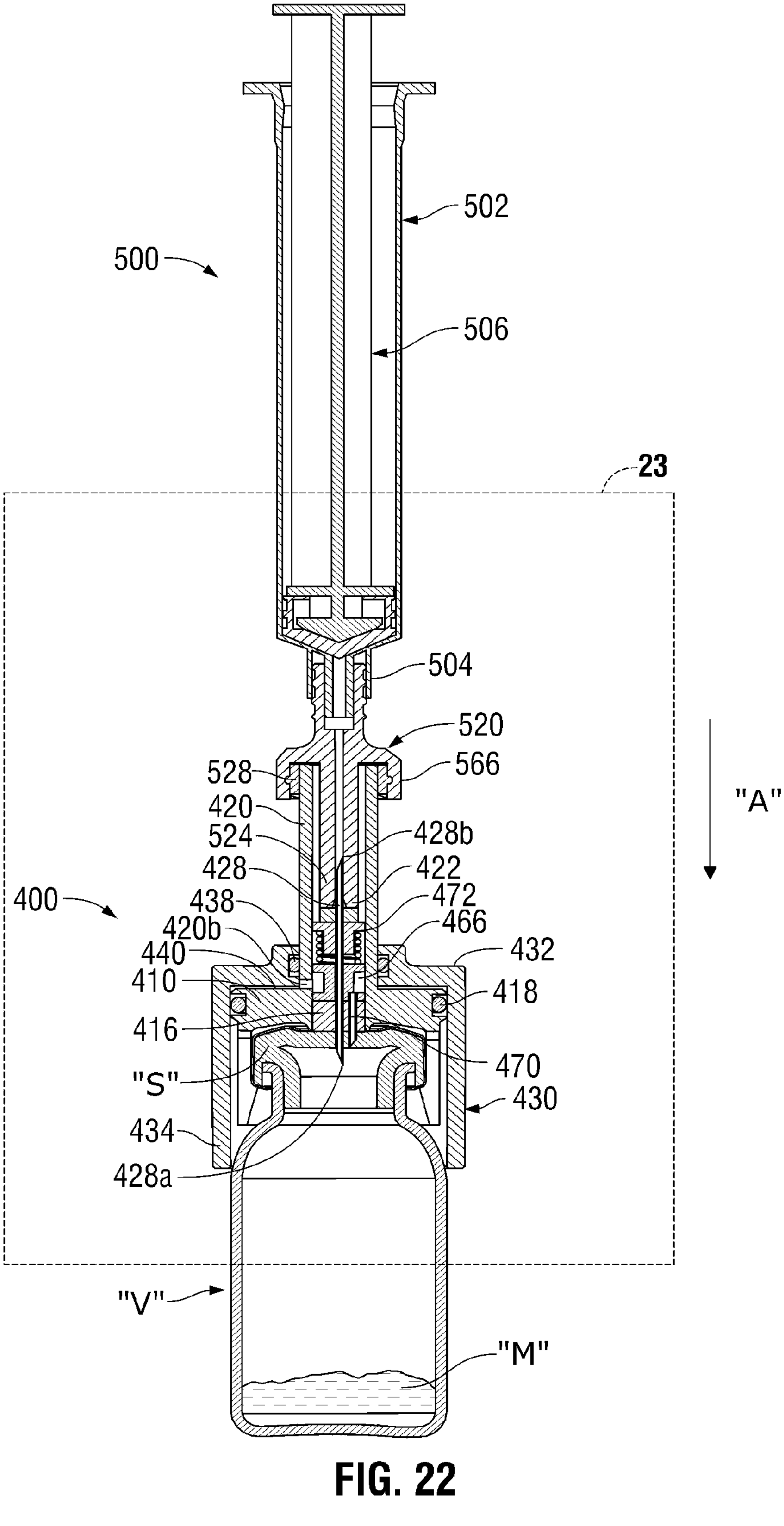
FIG. 22 is a longitudinal, cross-sectional, elevation view of the medicament transport system of FIGS. 14-21, shown in a second condition, and illustrating the syringe and syringe adapter operatively connected therewith.
Figure 23:
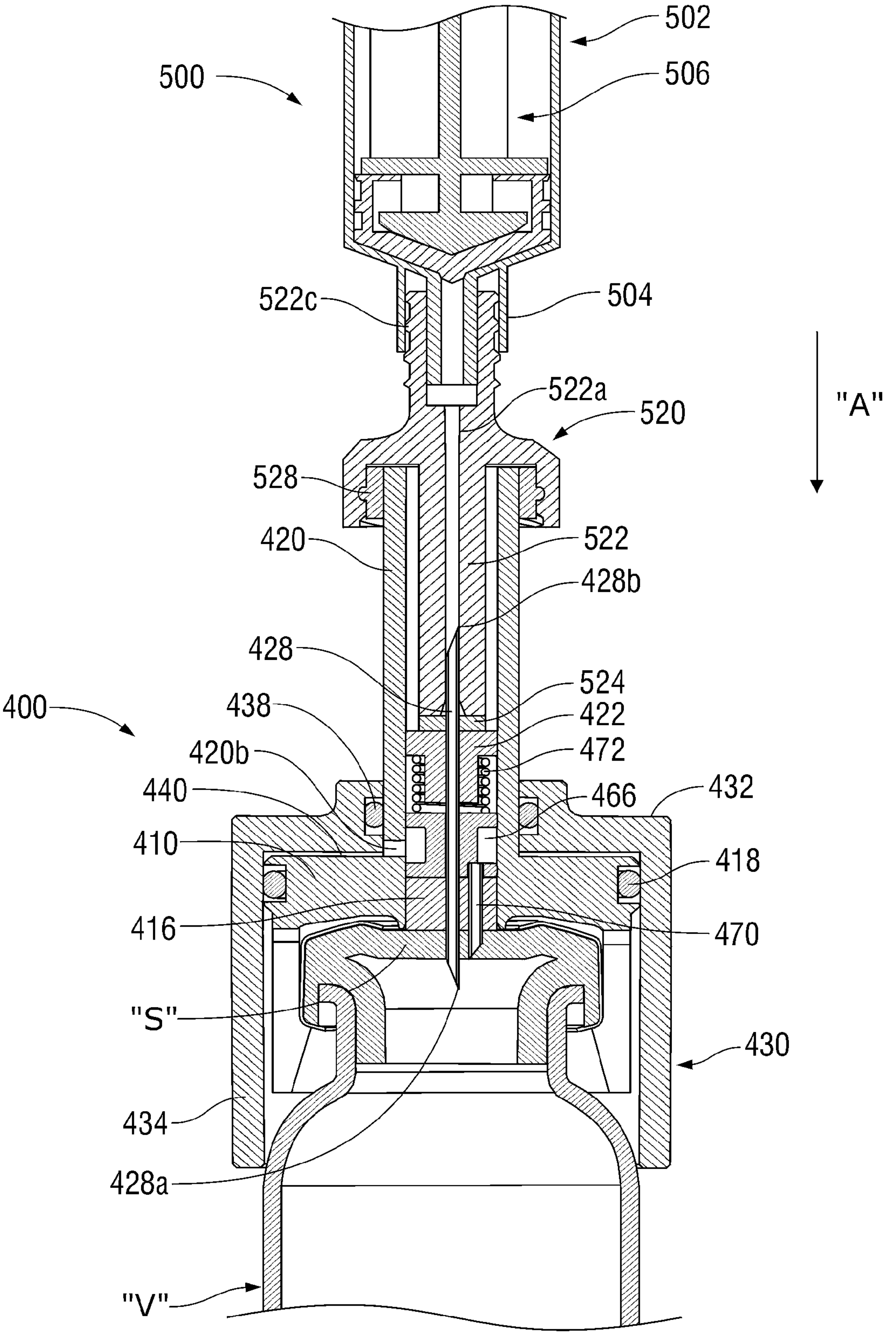
FIG. 23 is an enlarged view of the indicated area of detail of FIG. 22.

As seen in FIGS. 22 and 23, and to be described in greater detail below, vial adapter assembly 410 includes at least a second or actuated condition wherein seal member 422, and needle shuttle valve 460 (including transfer needle 428 and vacuum needle 470) are located at a relatively distal-most position within lumen 420*a* of stem 420. As so positioned, the distal tips of transfer needle 428 and vacuum needle 470 are penetrated through sealing member 416 of vial adapter assembly 410 and into vial "V." Also, as so positioned, biasing member 472 is in biased or compressed condition. Additionally, as so positioned, annular race 466*a* of needle shuttle valve 460 is brought into fluid communication with aperture 420*b* formed in the wall of stem 420, and thus vacuum needle 470 is brought into fluid communication with aperture 420*b* of stem 420.

With continued reference to FIGS. 14-19, medicament transport system 400 further includes a vacuum cup 430 slidably disposed on and about stem 420 of vial adapter assembly 410. Vacuum cup 430 includes a base wall 432 defining a central aperture 432*a* configured and dimensioned to slidably receive stem 420 therethrough. Central aperture 432*a* defines an inner annular race 432*b* extending therearound and being configured to support a seal member 438, in the form of an O-ring, gasket or other elastomeric member, therein. Vacuum cup 430 further includes an annular wall 434 extending from base wall 432, in a direction opposite to stem 420. Base wall 432 and annular wall 434 are dimensioned such that a fluid tight seal is formed or established with seal member 418 of vial adapter assembly 410.

As so arranged, as best seen in FIGS. 20-25, a vacuum chamber 440 is defined between vial adapter assembly 410 and vacuum cup 430. Vacuum chamber 440 is in fluid communication with aperture 420*b* formed in the wail of stem 420.

As seen in FIGS. 20-23, and to be described in greater detail below, vacuum cup 430 includes a first position wherein vacuum cup 430 is located at a relatively distal-most position relative to stem 420. As so positioned, vacuum chamber 440 is maintained at a relatively small volume.

Figure 24:
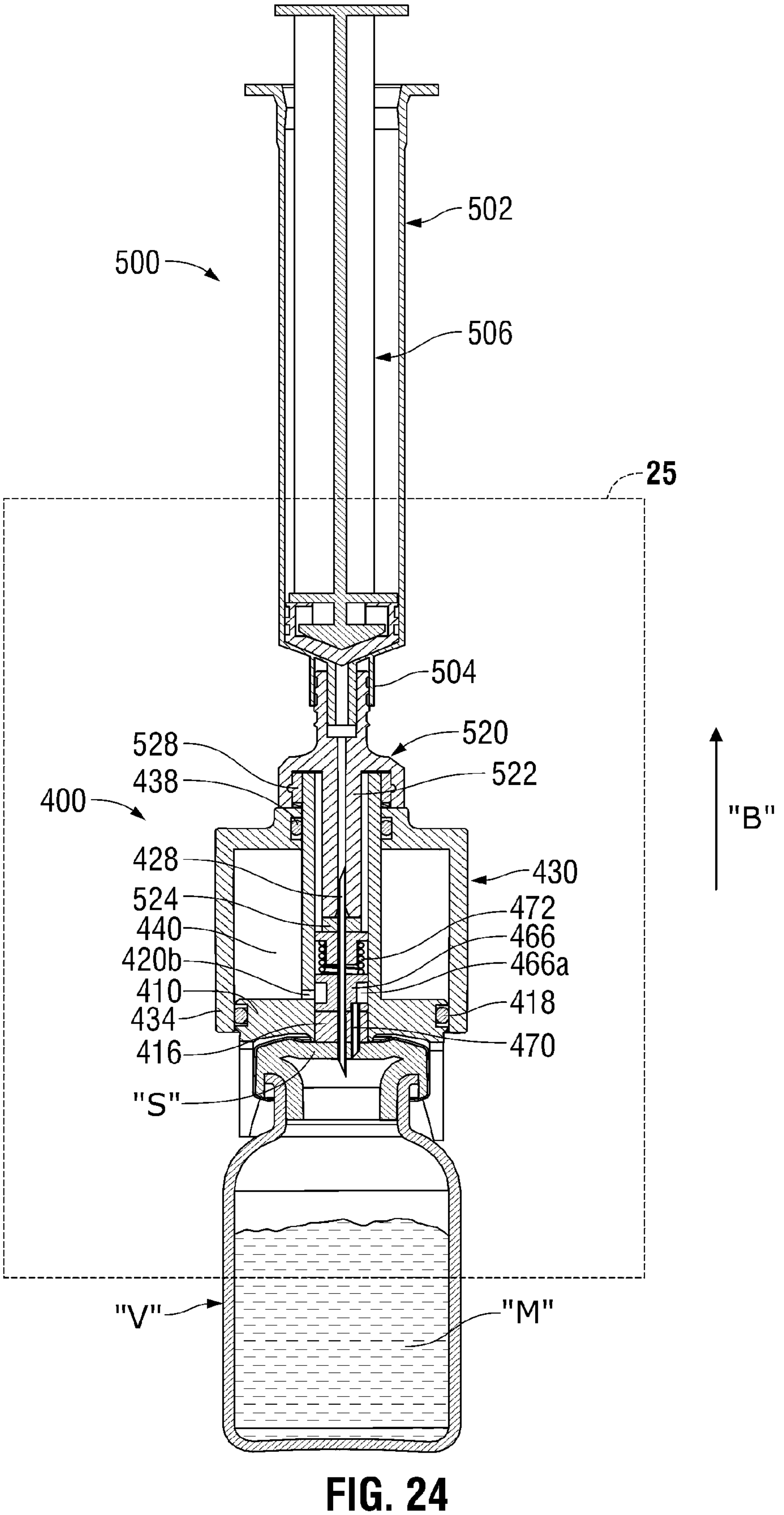
FIG. 24 is a longitudinal, cross-sectional, elevation view of the medicament transport system of FIGS. 14-23, shown in a third condition, while the syringe and syringe adapter are connected thereto.
Figure 25:
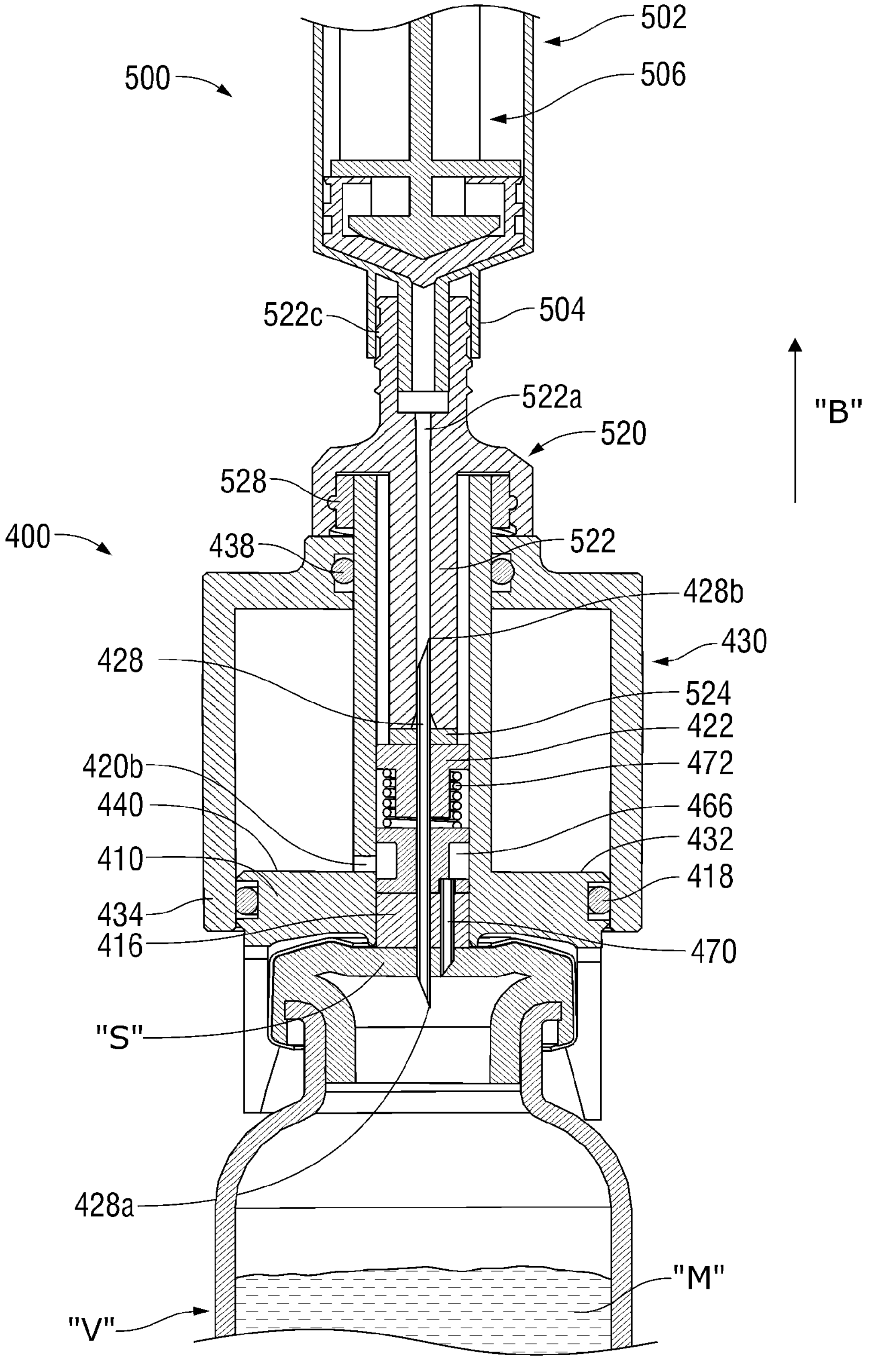
FIG. 25 is an enlarged view of the indicated area of detail of FIG. 24.

During manipulation of vial adapter assembly 410 to the second condition, as seen in FIGS. 24 and 25, and to be described in greater detail below, vacuum cup 430 is moved axially in a proximal direction along stem 420, to at least a second condition, thereby expanding or enlarging vacuum chamber 440. As vacuum chamber 440 is enlarged a vacuum or negative pressure in drawn through aperture 420*b* of stem 420, through annular race 466, through vacuum needle 470 and from vial "V."

Turning now to FIGS. 20-25, a method of using medicament transfer assembly 400, to constitute, prepare or otherwise gain access to a medicament "M," using a syringe 500 and a syringe adapter assembly 520 of medicament transport system 400, is shown and described. Initially, with reference to FIG. 21, syringe 500 includes a syringe barrel 502 having a nose 504 in fluid communication with a chamber of syringe barrel 502. Syringe 500 further includes a plunger 506 having a plunger stopper 508 supported on a distal end thereof, wherein the plunger 506 is slidably disposed within the chamber of syringe barrel 502.

As seen in FIG. 21, syringe adapter assembly 520 of medicament transport system 400 includes a body portion 522 defining a lumen 522*a* therethrough. Syringe adapter assembly 520 includes a seal member 524 supported on a first end 522*b* of body portion 522 to occlude lumen 522*a*. Syringe adapter assembly 520 includes a luer-type fitting or other engaging member formed at a second end 522*c* of body portion 522 and which is configured and dimensioned to selectively connect with nose 504 of syringe barrel 502.

Syringe adapter assembly 520 further includes an annular flange 526 extending from body portion 522 and having internal threads 526*a* configured to engage a threaded collar 528 supported on or at an end of stem 420 of vial adapter assembly 410. Collar 528 may act as an end stop for vacuum cup 430.

As seen in FIGS. 21 and 22, with syringe adapter assembly 520 connected to nose 504 of syringe barrel 502, and with vial adapter assembly 410 in the first or unactuated condition and connected to a vial "V" (as described above), syringe adapter assembly 520 is connected to vial adapter assembly 410. In particular, the distal end 522*b* of body portion 522 of syringe adapter assembly 520 is inserted and advanced into the lumen of stem 420 of vial adapter assembly 410.

As body portion 522 of syringe adapter assembly 520 is advanced into the lumen of stem 420 (as indicated by arrow "A" in FIGS. 22 and 23), vial adapter assembly 410 is manipulated from the first or unactuated condition to the second or actuated condition. In particular, body portion 522 of syringe adapter assembly 520 presses against and urges seal member 422 in a distal direction, which urges biasing member 472 in a distal direction, which urges needle shuttle valve 460 in a distal direction until needle shuttle valve 460 bottoms-out or engages sealing member 416 and biasing member 472 is compressed or biased. As body portion 522 of syringe adapter assembly 520 is advanced through stem 420, proximal tip 428*b* of transfer needle 428 is penetrated through seal member 422 of vial adapter assembly 410 and through seal member 524 of syringe adapter assembly 520. Also, as body portion 522 of syringe adapter assembly 520 is advanced through stem 420, distal tip 428*a* of transfer needle 428 is penetrated through seal member 416 of vial adapter assembly 410 and through stopper "S" of vial "V." Likewise, a distal tip of vacuum needle 470 is also caused to be penetrated through seal member 416 of vial adapter assembly 410 and through stopper "S" of vial "V."

With body portion 522 of syringe adapter assembly 520 fully advanced into stem 420 of vial adapter assembly 410, annular flange 526 of syringe adapter assembly 520 is coupled to threaded collar 528 of stem 420 to thereby maintain the relative position of syringe adapter assembly 520 with vial adapter assembly 410. Also, with body portion 522 of syringe adapter assembly 520 fully advanced into stem 420 of vial adapter assembly 410, annular race 466*a* of needle shuttle valve 460 is brought into fluid communication with aperture 420*b* formed in the wail of stem 420, and thus vacuum needle 470 is brought into fluid communication with aperture 420*b* of stem 420.

With syringe 500 fluidly connected to vial "V," plunger 506 of syringe 500 is advanced relative to syringe barrel 502 to deliver or inject a fluid/diluent into vial "V." In particular, the fluid/diluent travels through nose 504 of syringe 500, through transfer needle 428 and into vial "V." The fluid/diluent is used to combine with the material "M" in vial "V" and form an injectable liquid solution of said material. "M."

With reference to FIGS. 24 and 25, during injection of the fluid/diluent into vial "V," a pressure differential or vacuum is transmitted to vial "V" by vacuum cup 430. In particular, as the fluid/diluent is injected, at a rate, vacuum cup 430 is moved from the first condition to the second condition, as described above. As vacuum cup 430 is moved from the first condition to the second condition (as indicated by arrow "B"), vacuum chamber 440 is enlarged thereby communicating a vacuum into vial "V" via the aperture 420*b* formed in stem 420, via annular race 466*a* of needle shuttle valve 460, and via vacuum needle 470 extending into vial "V." The rate at which vacuum cup 430 is moved from the first condition to the second condition should be selected so as to be greater than the rate of delivery of the fluid/diluent. In use, while vacuum cup 430 is held in one hand of a user, and plunger 506 of syringe 500 is depressed or advanced relative to syringe barrel 502, the fluid/diluent is injected to vial "V" simultaneously with the drawing of a vacuum from vial "V" in one motion. In this manner, any gases or vapor that may be formed during the creating of the injectable liquid solution are drawn into vacuum chamber 440 of vial adapter assembly 410.

Following creation of the injectable liquid solution, syringe 500, vial adapter assembly 410 and vial "V" are inverted, the plunger 506 is withdrawn relative to syringe barrel 502 to withdraw a quantity of liquid solution. Then, the user disconnects syringe adapter assembly 520 from vial adapter 410. In so doing, body portion 522 of syringe adapter assembly 520 is withdrawn from within stem 420, biasing member 472 is permitted to uncompress and thus move seal member 428 in a proximal direction and passed tip 428*b* of transfer needle 428.

It is contemplated that a biasing member (not shown) may be interposed between needle shuttle 466 and seal member 416, to thereby urge needle shuttle 466 in a proximal direction during/following withdrawn or disconnection of syringe adapter assembly 520 from vial adapter assembly 410, whereby annular race 466*a* of needle shuttle 466 is moved out of fluid communication with aperture 420*b* of stem 420. In this manner, any gases or vapors drawn into vacuum chamber 440 remain contained within vacuum chamber 440 until such time that said gases or vapors can be properly disposed of.

While it is contemplated that the use of vial adapter assembly 410 and syringe adapter assembly 520 are to be by hand it is envisioned and within the scope of the present disclosure that vial adapter assembly 410 and syringe adapter assembly 520 may be incorporated in whole or in part into any automated-type systems.

Turning now to FIGS. 26-37, an automated system for filling syringes with doses of medication, incorporating a medicament transport system of the present disclosure, is generally designated as automated system 700. Automated system 700 includes a housing or cabinet 702 defining a chamber 704. Cabinet 702 supports a door 706 which is selectively operable and closable to allow or restrict entry into chamber 704.

Automated system 700 includes a carousel 708 of trays 710 rotatably supported in cabinet 702. Each tray 710 is configured to support a plurality of vials "V" thereon in an inverted orientation. While each tray 710 is shown supporting six (6) vials "V", it is contemplated that each tray 710 may support any number of vials thereon. Trays 710 are further configured to permit access to the stoppers of vials "V." While four (4) trays 710 are shown, it is contemplated that any number of trays may be provided. Carousel 708 is oriented such that trays 710 extend in a relatively horizontal direction with carousel 708 rotating about a horizontal axis.

Trays 710 may be locked into position to enable access to the vials "V" supported thereon. Also, trays 710 may be provided with an agitating mechanism to allow trays 710 to be oscillated or otherwise moved to shake/agitate the contents of the vials "V" supported thereon.

Automated system 700 further includes at least one cartridge or magazine 712 of syringes 500. Each magazine 712 is configured to selectively release a single syringe 500 at a time and then advance the remaining syringes 500 to a loading position. As seen in FIGS. 27-31, each magazine 712 is configured to releasably store or retain a plurality of syringe adapter assemblies 520 (substantially as described above).

Automated system 700 further includes a robotic or automated loading arm 714 movably disposed within cabinet 702. Loading arm 714 translates on a pair of rails 716, 718 thereby permitting loading arm 714 to move in two-planes. Loading arm 714 includes a jaw member 720 having a pair of jaws 720*a*, 720*b* configured to translate relative to one another. Each jaw 720*a*, 720*b* includes a pair of respective fingers 722*a*, 722*b* configured and adapted to releasably engage syringes 500. Fingers 722*a*, 722*b* may be actuated, thereby allowing fingers to be opened and closed as needed to grab and/or release syringes 500. Likewise, jaws 720*a*, 720*b* may be actuated, thereby allowing relative opening and closing thereof to advance/retract the plunger of the syringe 500 relative to the syringe barrel.

With reference to FIGS. 26-37 and FIGS. 38A-38H, a process of operating automated system 700, in accordance with the principles of the present disclosure, is provided. As seen in FIG. 38A, at step 800 the process is initiated. At Step 802 an order is read by system 700, and at Step 804 an order is printed. At Step 806, it is determined if the order requires a medicament to be reconstituted or if the order is to be used in an IV bag.

Figure 38A:
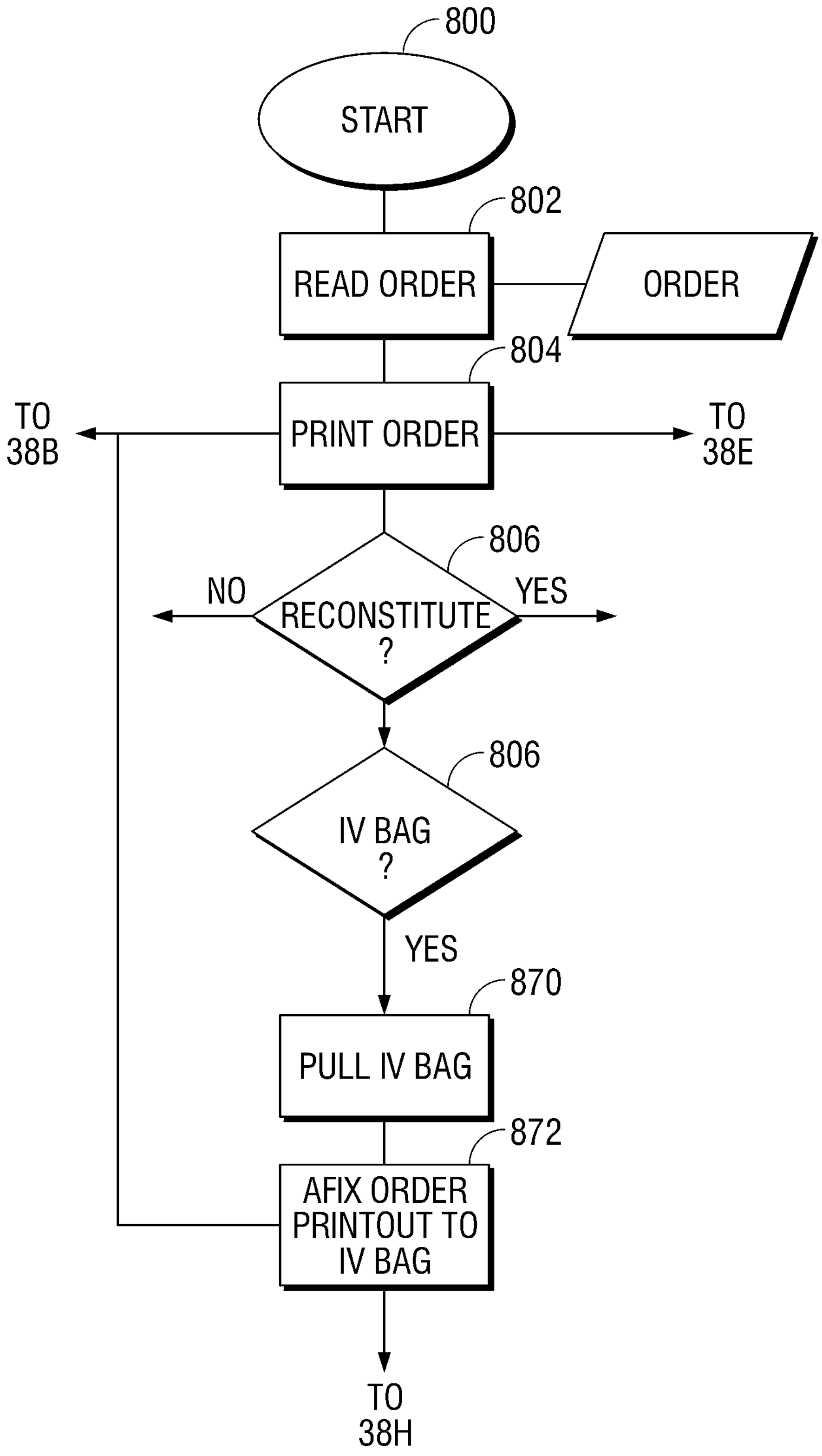
FIGS. 38A-38H is a process flow diagram illustrating a method of use of the automated system of FIGS. 26-37 together with a medicament transport system of the present disclosure.
Figure 38B:
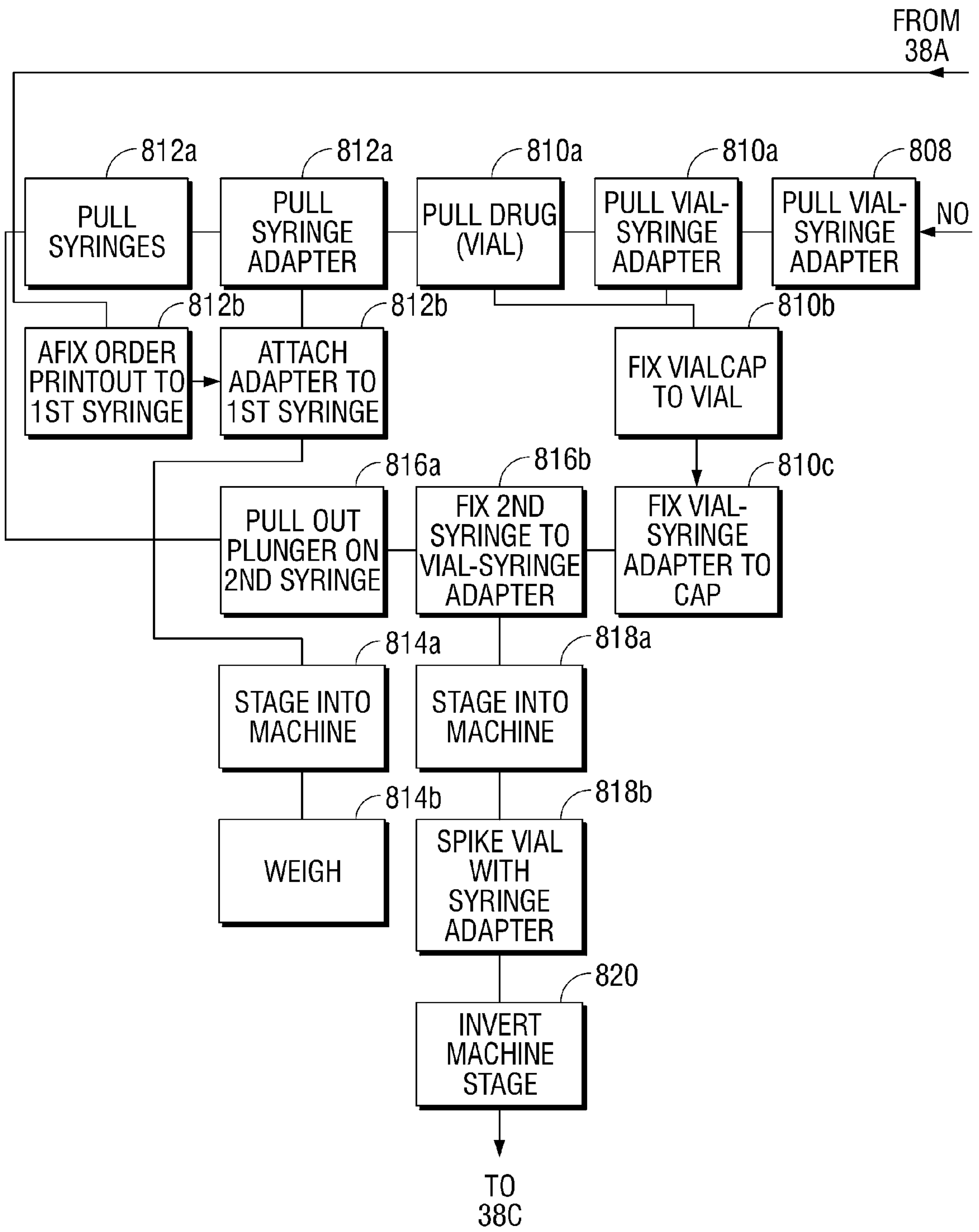

If the order does not require reconstitution, then, as seen in FIG. 38B, at Step 808 a vial-syringe adapter is pulled. At Step 810*a*, a vial containing the medicament is pulled and a vial cap assembly is pulled. At Step 810*b*, the vial cap assembly is affixed to the vial. At Step 810*c*, the vial-syringe adapter in connected to the vial cap assembly At Step 812*a*, a first and a second syringe are pulled and a first syringe adapter is pulled. At Step 812*b*, the order printed at Step 804 is affixed to the first syringe, and the first syringe adapter is attached to the first syringe. At Step 814*a*, the first syringe is staged in the machine (as seen in FIGS. 26-32), and at Step 814*b*, the first syringe is weighed. At Step 816*a*, a plunger of the second syringe is pulled out, and at Step 816*b*, the second syringe is connected to vial-syringe adapter that was pulled at Step 808. At Step 818*a*, the second syringe is staged in the machine, and at Step 818*b*, the vial is spiked by the vial-syringe adapter. At Step 820, the first syringe, the second syringe and the vial are inverted.

Figure 38C:
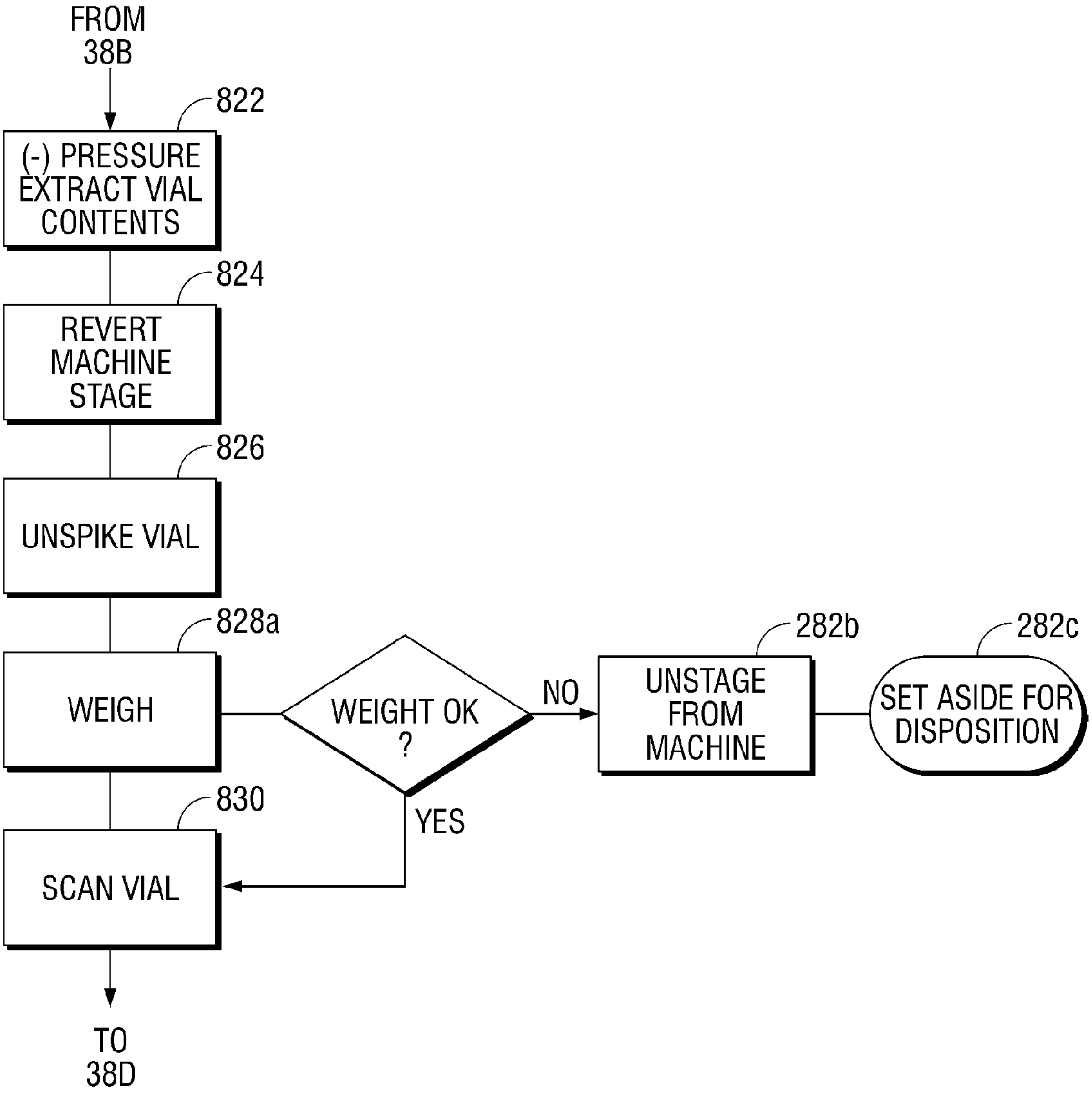

As seen in FIG. 38C, at Step 822 a negative pressure or vacuum is applied to the vial to extract contents from the vial (e.g., medicament). At Step 824, the first syringe, the second syringe and the vial are reverted. At Step 826, the vial is unspiked. At Step 828*a*, the vial is weighed. If the weight of the vial is not correct or not equal to an expected weight, at Step 828*b*, the vial is unstaged from the machine, and at Step 828*c*, the vial is set aside for disposition. If the weight of the vial is correct or is equal to an expected weight, than at Step 830, the vial is scanned.

Figure 38D:
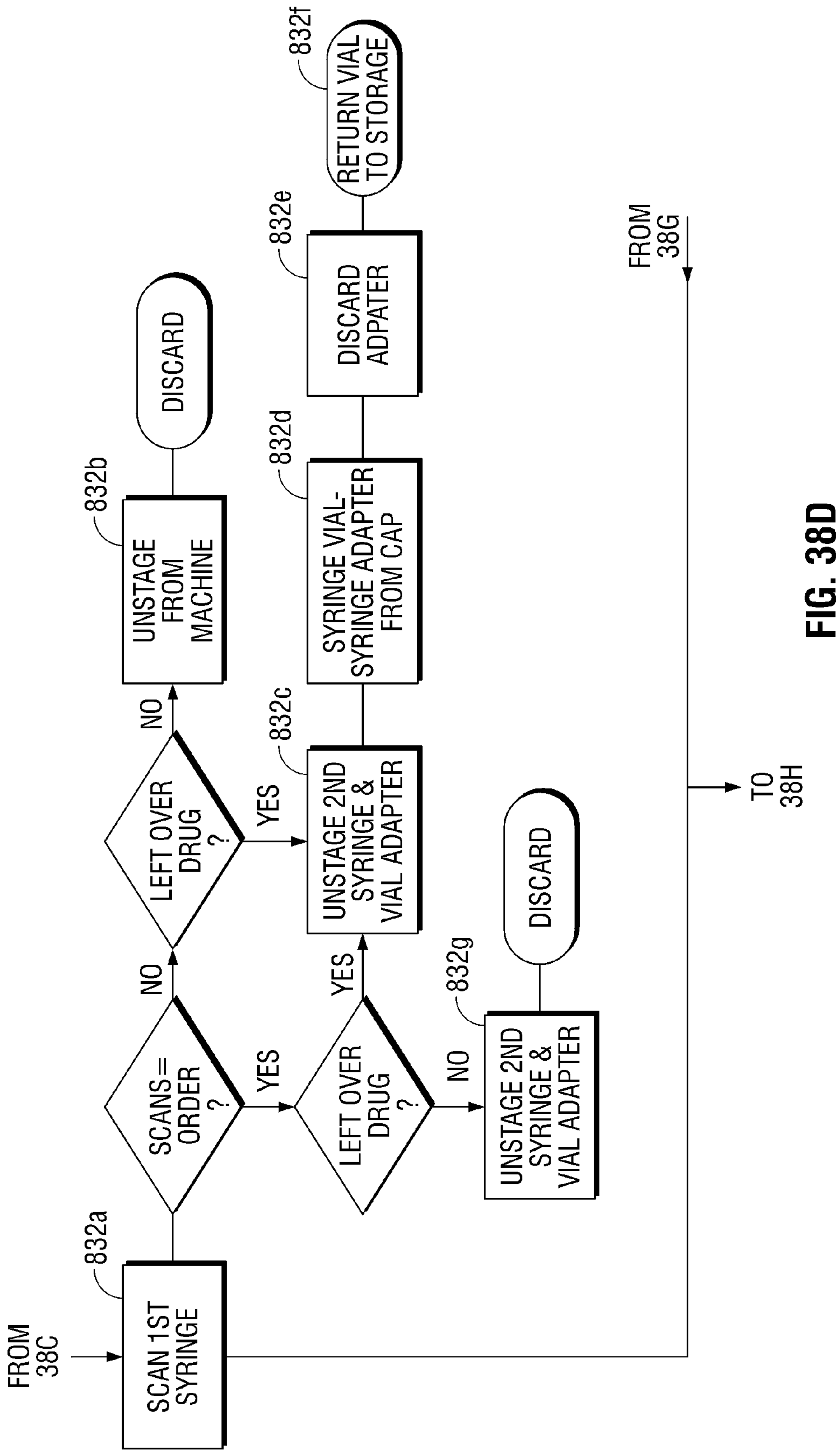

As seen in FIG. 38D, at Step 832*a*, the first syringe is scanned. If the information from the scan does not equal the information of the order and if there is no remaining drug, then at Step 832*b* the first syringe is unstaged from the machine and discarded. If the information from the scan does not equal the information of the order and if there is drug remaining, then at Step 832*c* the second syringe and the vial-syringe adapter are unstaged from the machine. Then, at Step 832*d* the vial-syringe adapter is separated from the cap, at Step 832*e* the vial-syringe adapter is discarded and, at Step 832*f* the vial is returned to storage. If the information from the scan does equal the information of the order and if there is drug remaining, then Steps 832*c*-832*f* are once again performed. If the information from the scan does equal the information of the order and if there is no drug remaining, then at Step 832*g* the second syringe and the vial-syringe adapter are unstaged and discarded.

Figure 37:
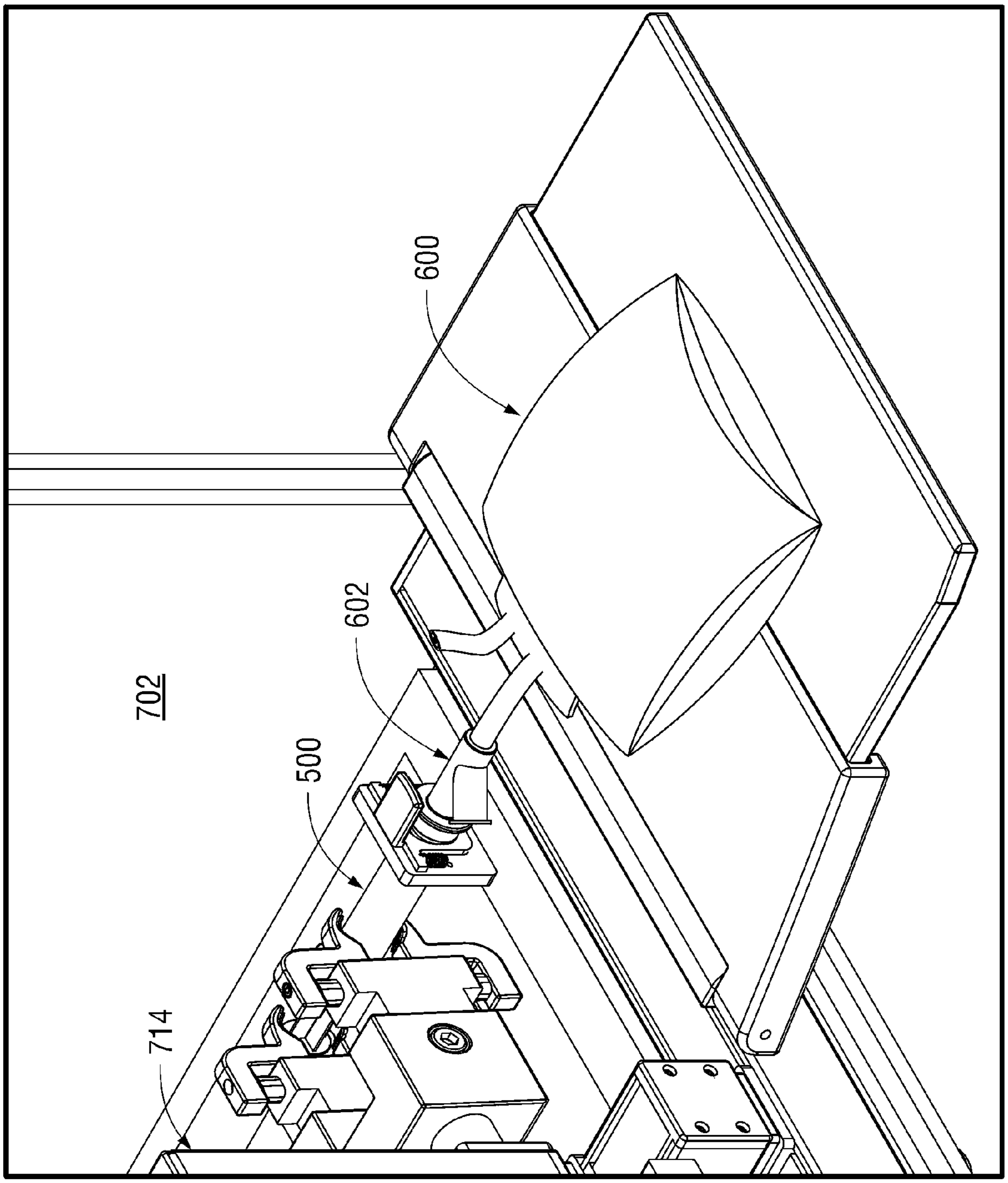
FIG. 37 is an enlarged view of the automated system on FIG. 26, shown with the loading arm having moved the filled syringe into connection with an IV bag.
Figure 38E:
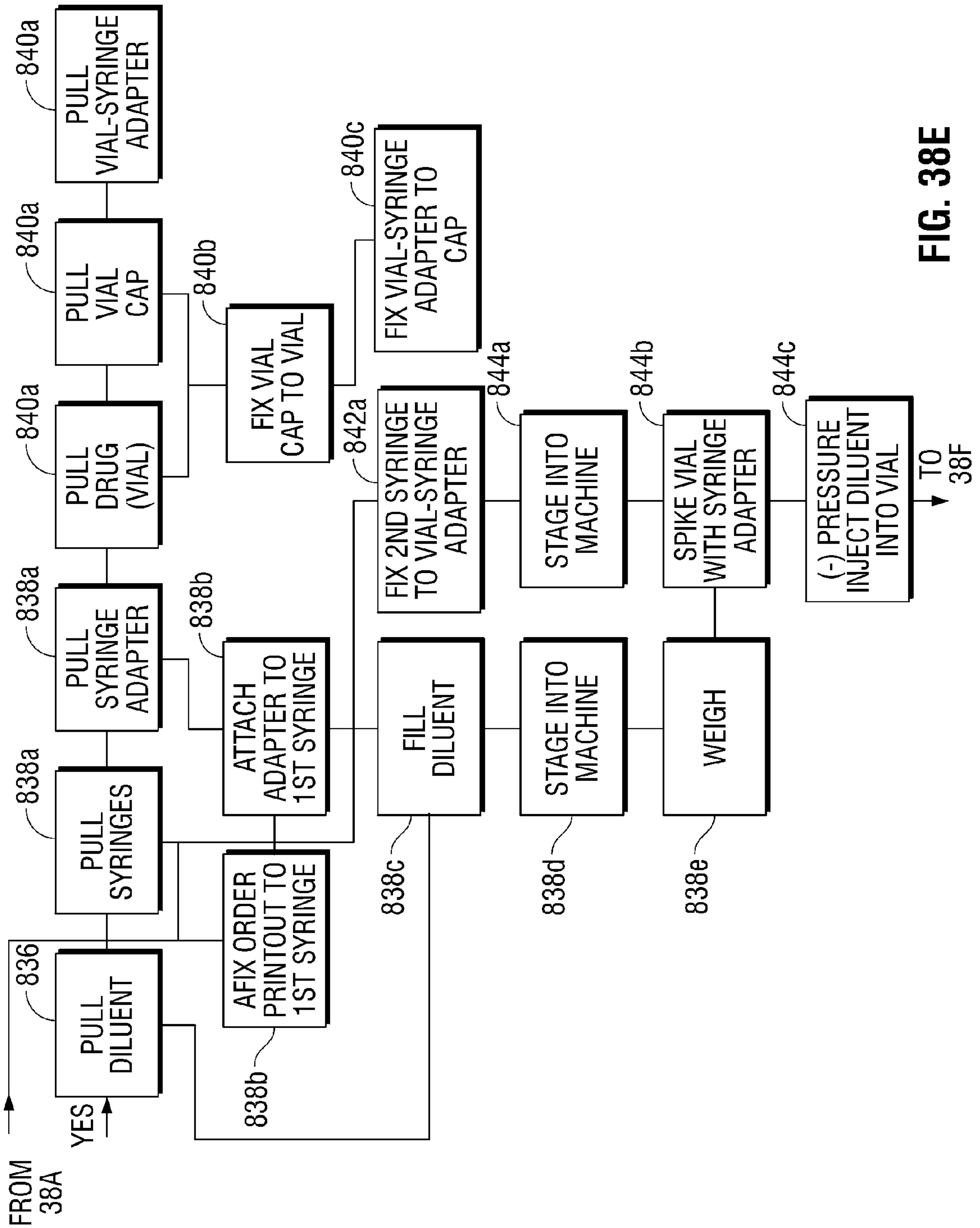
Figure 38F:
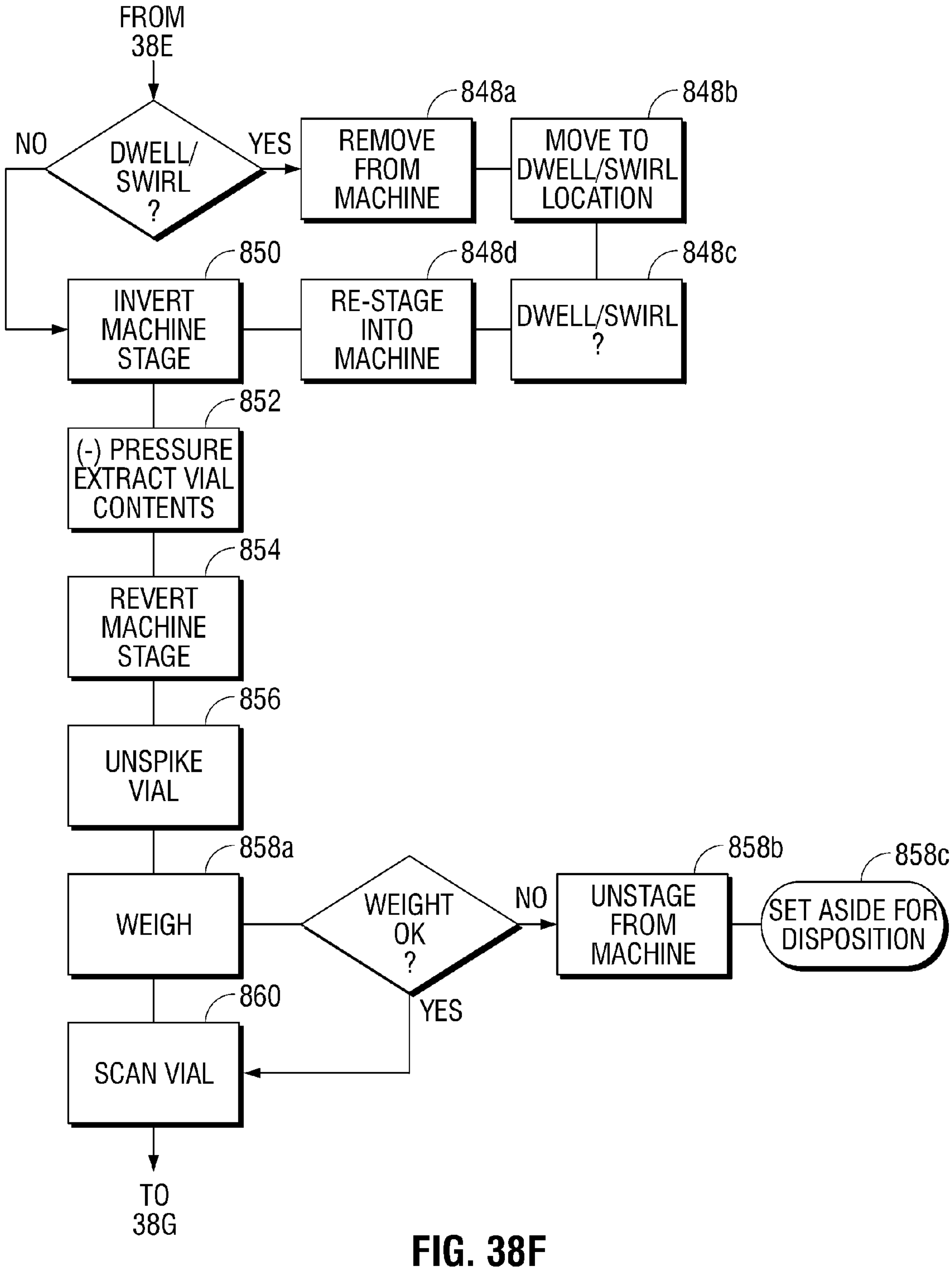
Figure 38G:
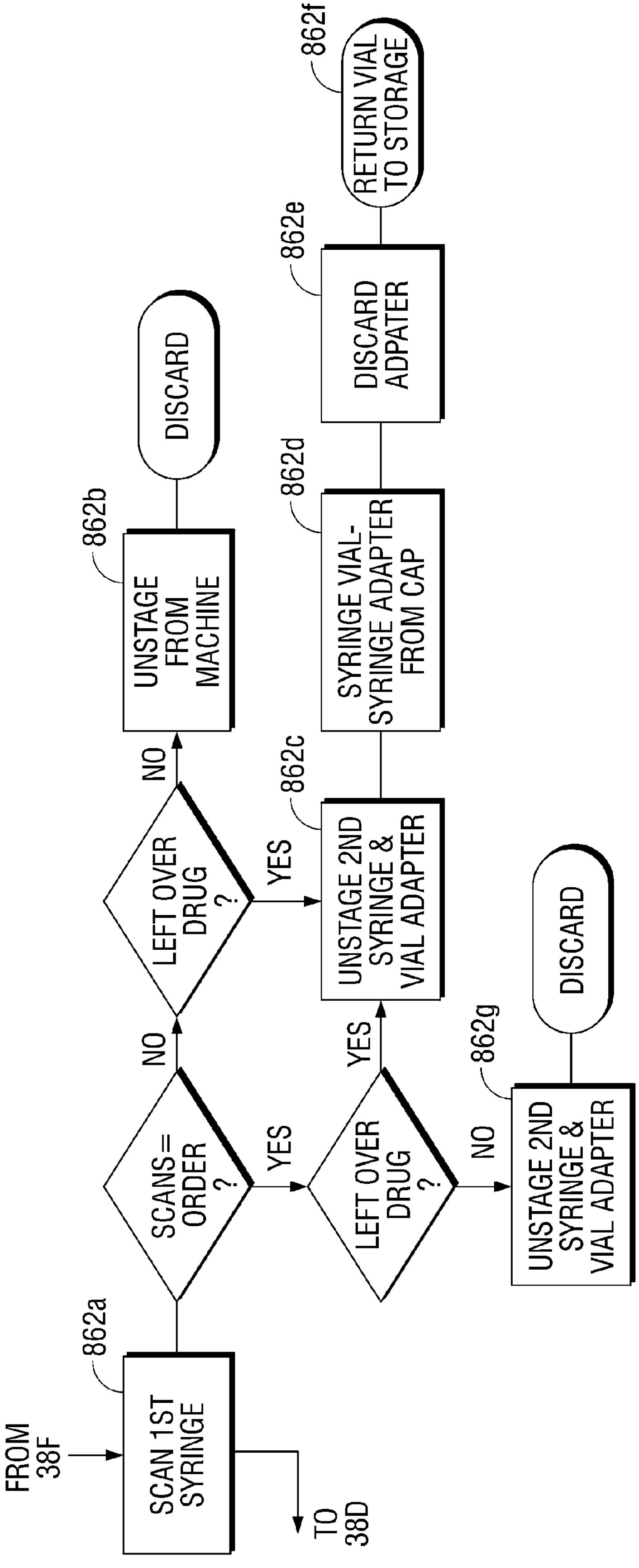
Figure 38H:
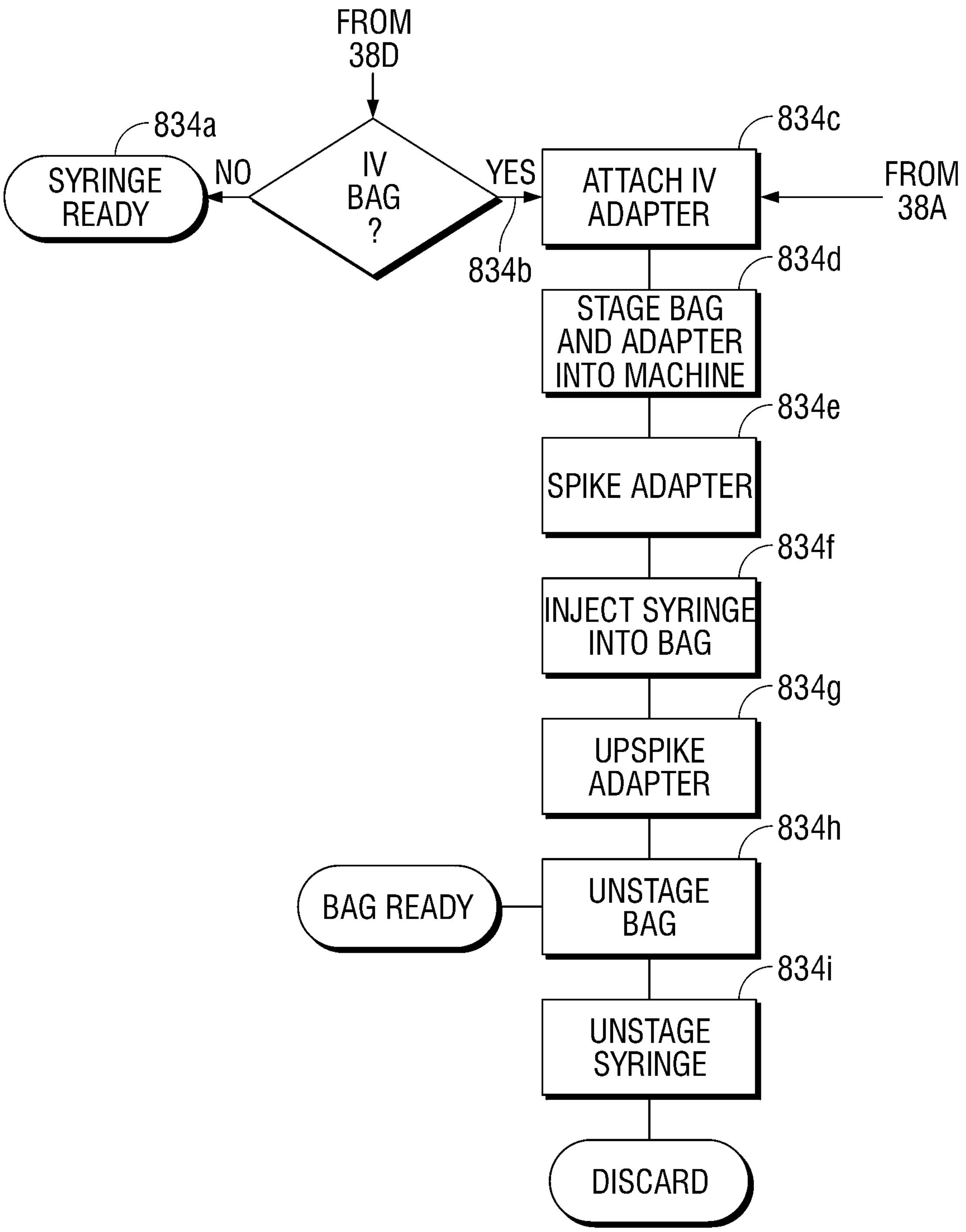

Simultaneously with the performance of some or all of Steps 832*b*-832*g*, as seen in FIG. 38H, following the scanning of the first syringe at Step 832*a*, then at Step 834*a*, if the first syringe is not to be used in an IV bag 600 (see FIG. 37), then the first syringe is ready. Alternatively, at Step 834*b*, if the first syringe is to be used in an IV bag 600, then an IV bag adapter 602 is attached to the first syringe at Step 834*c*. Then, at Step 834*d* the IV bag 600 and the IV bag adapter 602 are staged in the machine, at Step 834*e* the IV bag adapter is spiked, at Step 834*f* the contents of the first syringe are injected into the IV bag 600, and at Step 834*g*, IV bag 600 is unspiked. Then at Step 834*h*, the IV bag 600 is unstage as the bag 600 is ready, and at Step 834*i*, the first syringe is unstaged and discarded.

Referring back to FIG. 38A and with reference to FIG. 38E, if the order does require reconstitution, then, at Step 836 a diluent is pulled. Then, at Step 838*a* a first and a second syringe are pulled and a first syringe adapter is pulled. At Step 838*b* the order printed at Step 804 is affixed to the first syringe, and the first syringe adapter is attached to the first syringe. At Step 838*c* the first syringe is filled with the diluent, at Step 838*d* the first syringe is staged in the machine, and at Step 838*e* the first syringe is weighed.

Substantially simultaneously therewith, at Step 840*a* a vial containing the medicament, a vial cap and a vial syringe adapter is pulled. At Step 840*h* the vial cap is connected to the medicament vial and, at Step 840*b* the vial-syringe adapter is connected to the vial cap. At Step 840*c* the vial-syringe adapter is connected to the vial cap. At Step 842*a* the second syringe is connected to the vial-syringe adapter, and at Step 842*b* the second syringe is connected to vial-syringe adapter that was pulled at Step 838*a*. At Step 844*a* the second syringe is staged in the machine, and at Step 844*b* the medicament vial is spiked by the vial-syringe adapter. At Step 846 a negative pressure or vacuum is applied to the medicament vial while the diluent is injected into the medicament vial.

As seen in FIG. 38F, if there needs to be a dwell time or a swirling of the vial, at Step 848*a* the vial is removed from the machine, at Step 848*b* the vial is taken to a dwell/swirl location, at Step 848*c* the vial is then allowed to dwell or is swirled as needed, and at Step 848*d* the vial is then re-staged in the machine.

With continued reference to FIG. 38F, following dwelling/swirling of the vial at steps 848*a*-848*c*, or if no dwelling/swirling is required, at Step 850 the first syringe, the second syringe and the vial are inverted. At Step 852 a negative pressure or vacuum is applied to the vial to extract contents from the vial (e.g., the reconstituted medicament). At Step 854 the first syringe, the second syringe and the vial are reverted. At Step 856 the vial is unspiked. At Step 858*a* the vial is weighed. If the weight of the vial is not correct or not equal to an expected weight, at Step 858*b* the vial is unstaged from the machine, and at Step 858*c* the vial is set aside for disposition. If the weight of the vial is correct or is equal to an expected weight, then at Step 860, the vial is scanned.

As seen in FIG. 38G, at Step 862*a* the first syringe is scanned. If the information from the scan does not equal the information of the order and if there is no remaining drug, then at Step 862*b* the first syringe is unstaged from the machine and discarded. If the information from the scan does not equal the information of the order and if there is drug remaining, then at Step 862*c* the second syringe and the vial-syringe adapter are unstaged from the machine. Then, at Step 862*d* the vial-syringe adapter is separated from the cap, at Step 862*e* the vial-syringe adapter is discarded and, at Step 862*f* the vial is returned to storage. If the information from the scan does equal the information of the order and if there is drug remaining, then Steps 862*c*-862*f* are once again performed. If the information from the scan does equal the information of the order and if there is no drug remaining, then at Step 862*g* the second syringe and the vial-syringe adapter are unstaged and discarded.

Following the scanning of the first syringe at Step 862*a*, and simultaneously with the performance of some or all of Steps 862*b*-862*g*, as seen in FIG. 38H, following the scanning of the first syringe at Step 862*a*, then Steps 834*a*-834*h* may be performed, as described above.

Alternatively, referring back to FIG. 38A, if the order is to require the use of an IV bag, then at Step 870, an IV bag is pulled, and at step 872 the order is affixed to the IV bag. Following the fixation of the order to the IV bag, then Steps 834*a*-834*h* may be performed, as described above.

Figure 39A:
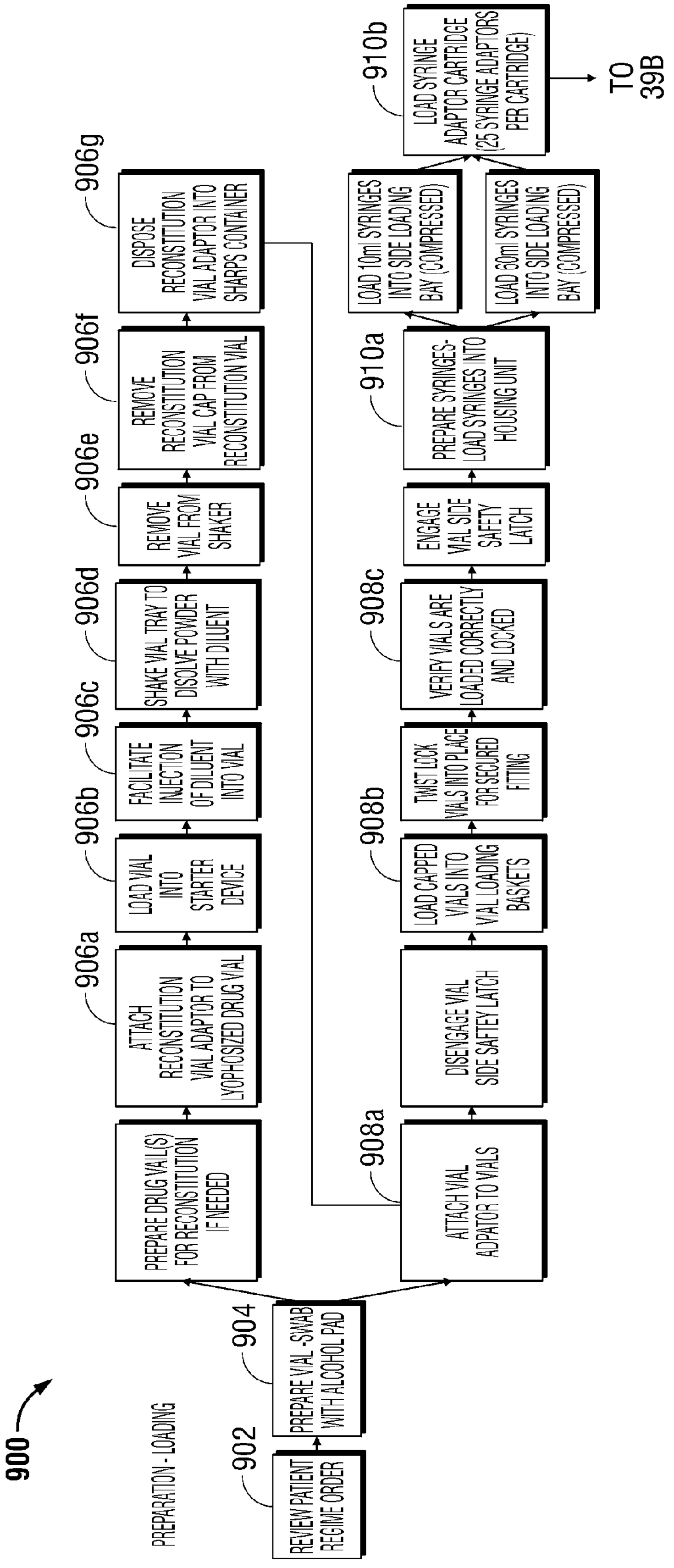
FIGS. 39A-39C is a process flow diagram illustrating a further method of use of the automated system of FIGS. 26-37 together with a medicament transport system of the present disclosure.

With reference to FIGS. 26-37 and FIGS. 39A-39C, a further process of operating automated system 700, in accordance with the principles of the present disclosure, is provided. As seen in FIG. 39A, at step 900 the process is initiated by preparing and loading system 700. At Step 902 the patient regime order is reviewed, and at Step 904 the appropriate vial is swabbed with an alcohol pad or the like.

If the medicament in the vial requires reconstitution, then at Step 906*a* a reconstitution vial adapter assembly is attached to the lyopholized medicament vial. At Step 906*b* the lyopholized medicament vial is loaded into a shaker device, at Step 906*c* a diluent is injected into the lyopholized medicament vial, and at Step 906*d* the shaker device is activated to dissolve the powdered medicament with the diluent. At Step 906*e* the vial is removed from the shaker, at Step 906*f* the reconstitution vial adapter assembly is removed, and at Step 906*g* the reconstitution vial adapter assembly is discarded.

Figure 26:
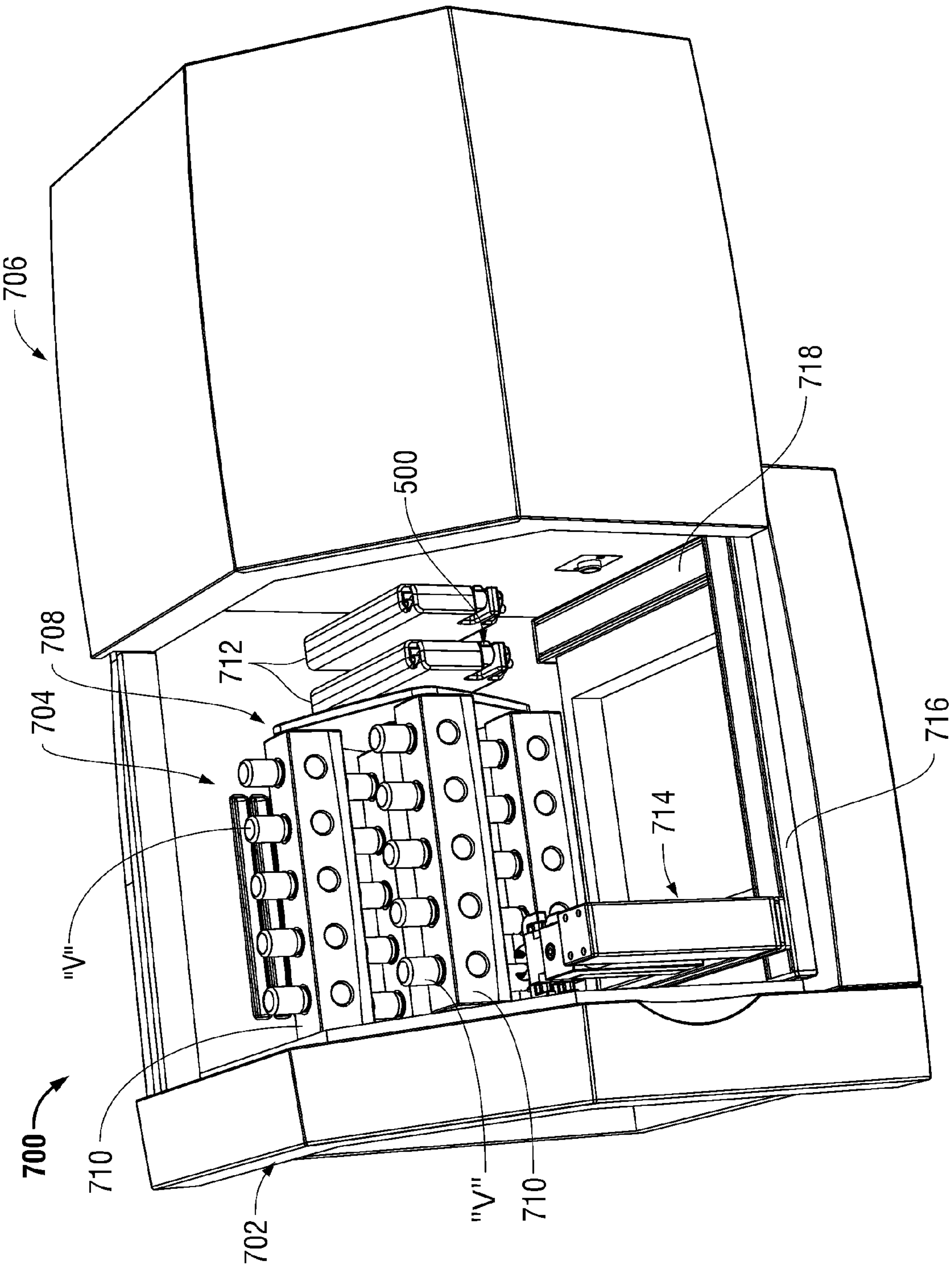
FIG. 26 is a perspective view of an automated system incorporating a medicament transport system of the present disclosure therein, shown with a door thereof in an open position.
Figure 27:
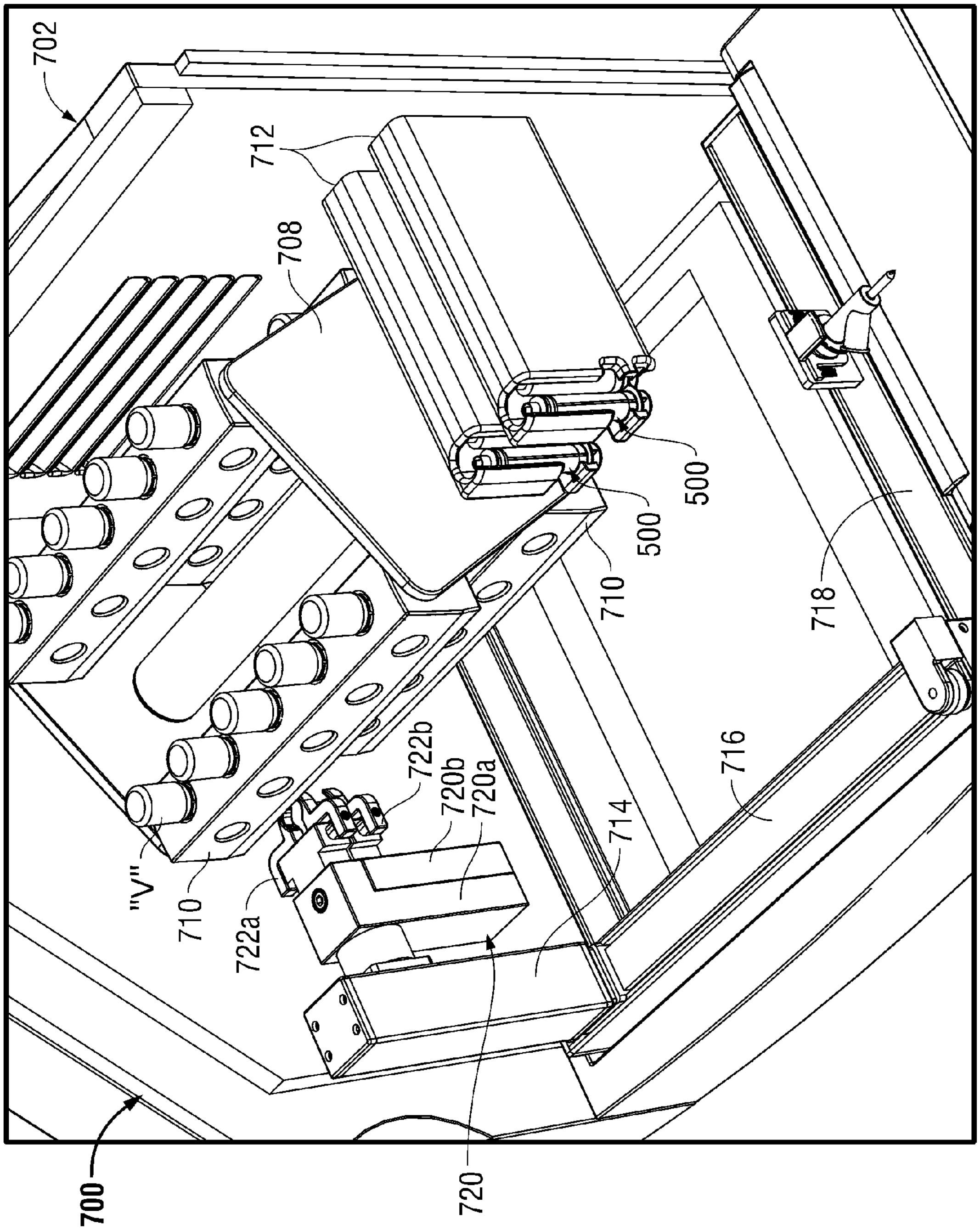
FIG. 27 is an enlarged detail view of the automated system of FIG. 26, shown with a loading arm thereof in a home position.
Figure 28:
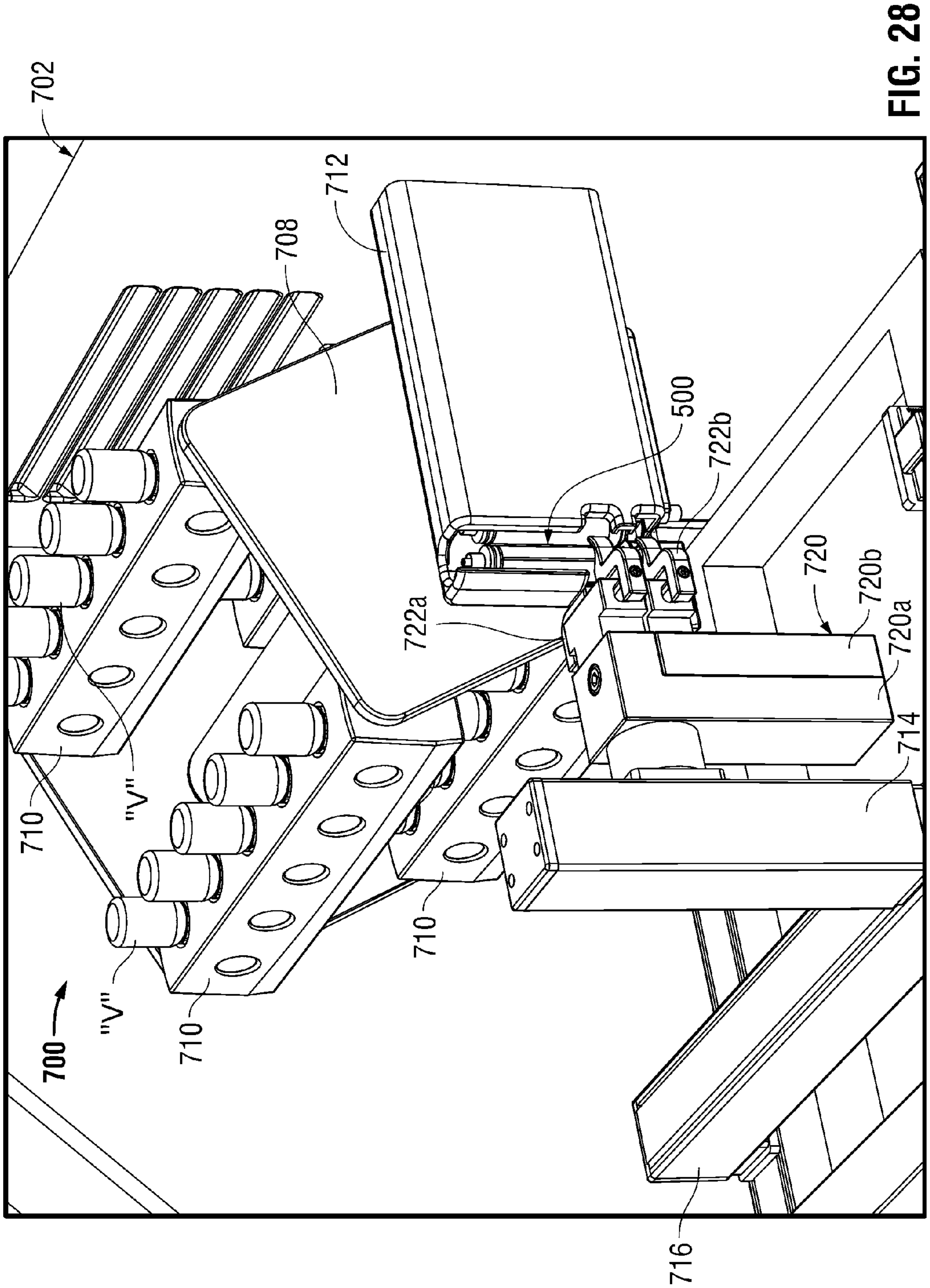
FIG. 28 is an enlarged detail view of the automated system of FIG. 26, shown with the loading arm thereof in a loading position with a syringe magazine.
Figure 29:
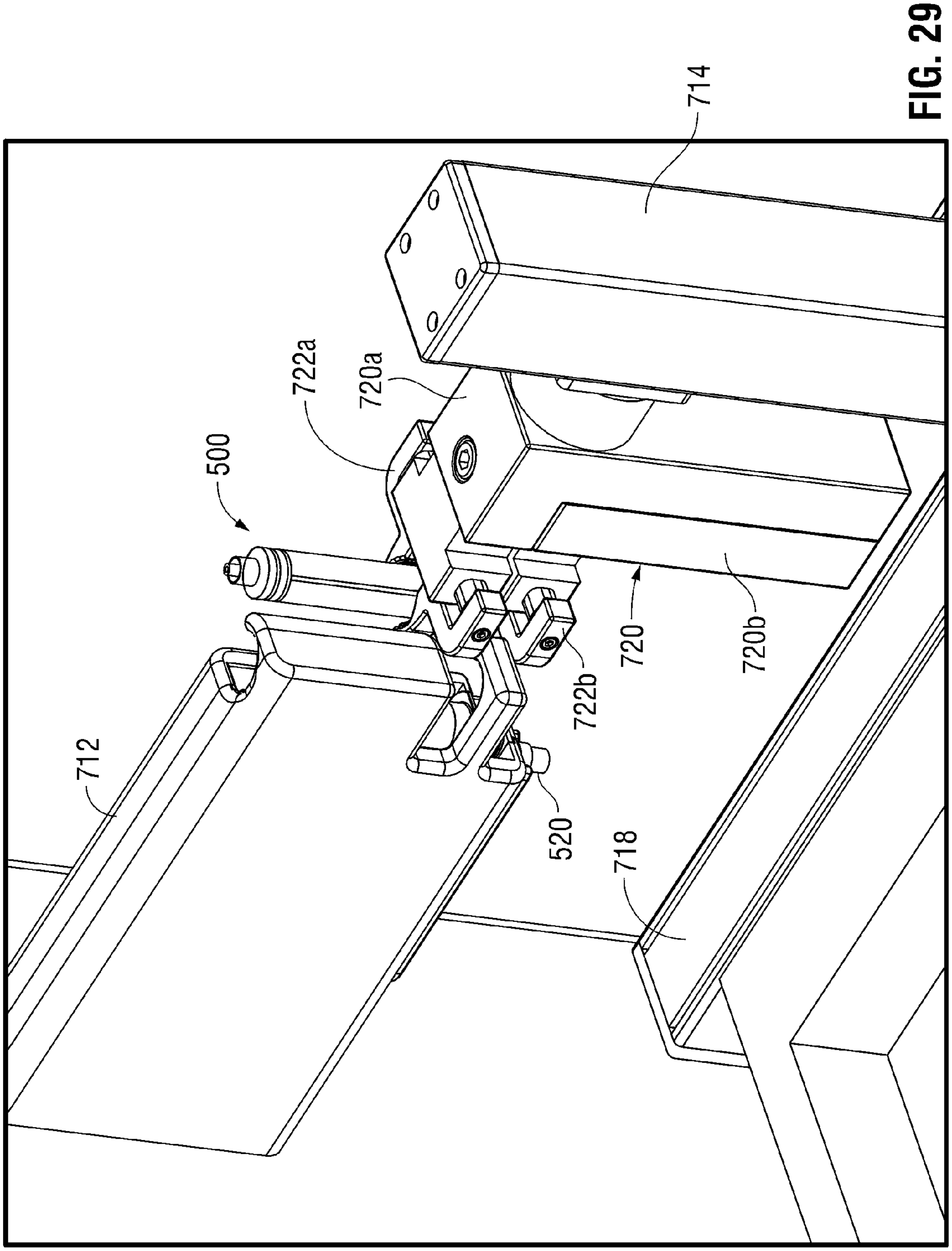
FIG. 29 is an enlarged detail view of the automated system of FIG. 26, shown with the loading arm thereof removing a syringe from the syringe magazine.

Thereafter or if the medicament in the vial does not require reconstitution, at Step 908*a* a vial adapter assembly is attached to the vial, and at Step 908*b* the vials that are capped with the vial adapter assemblies are loaded into baskets or trays (as seen in FIG. 26). The vials may be locked into place by means of a twist lock arrangement or the like. At Step 908*c* the proper loading of the vials is verified.

At Step 910*a* syringes are prepared by loading the syringes into the housing of system 700 (as seen in FIGS. 26-30). Either 10 ml 60 ml syringes (in a compressed state) are loaded. At Step 910*b* a cartridge having a plurality of syringe adapters is loaded into the housing of system 700.

Figure 39B:
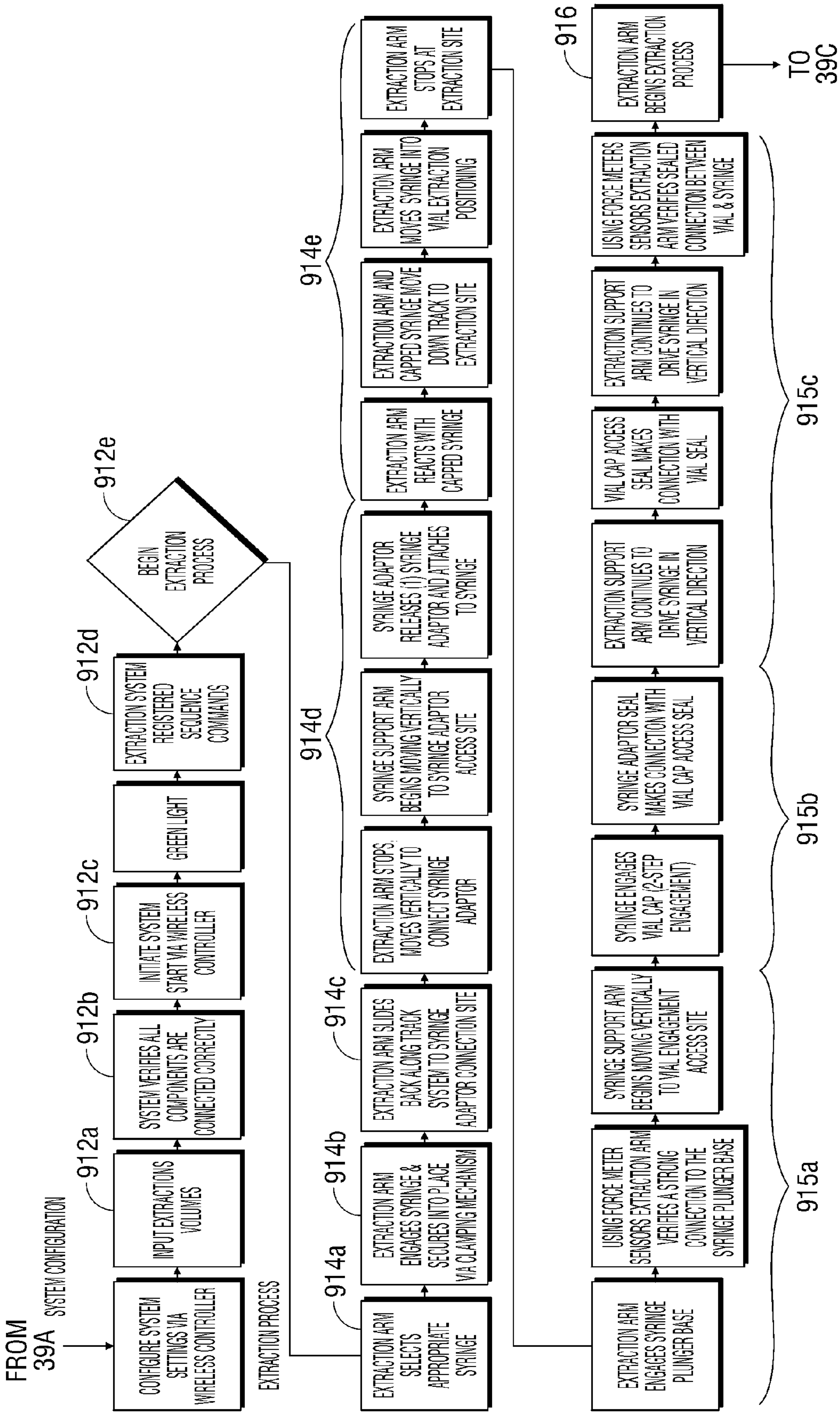

As seen in FIG. 39B, at Step 912 system 700 is configured. At Step 912*a* the extraction volumes are imputed into system 700, at Step 912*b* system 700 verifies that all the components are connected correctly, at Step 912*c* a system start is initiated (optionally via wireless controller), at Step 912*d* system 700 registers sequence commands, and at Step 912*e* an extraction process begins.

Figure 30:
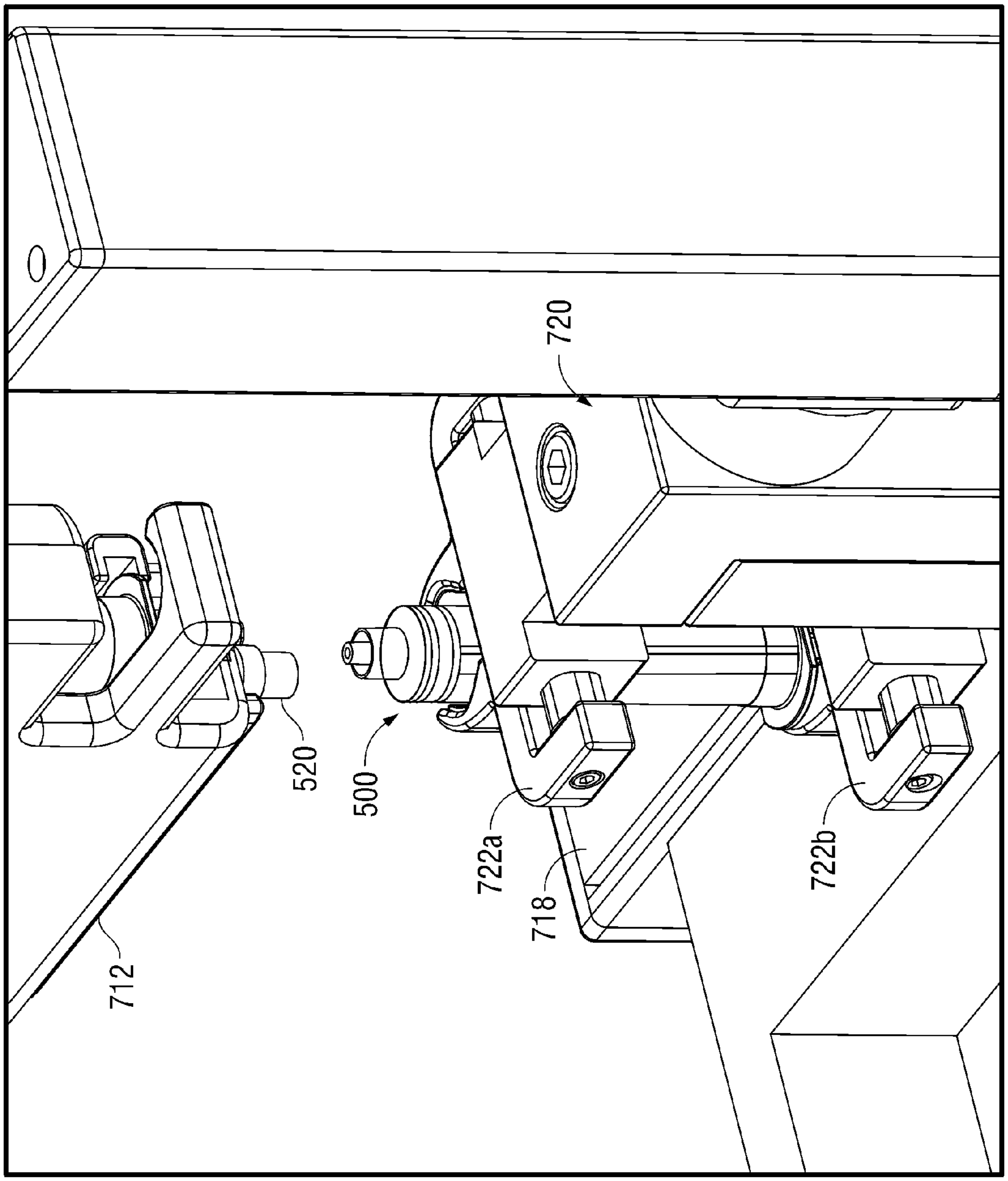
FIG. 30 is an enlarged detail view of the automated system of FIG. 26, shown with the loading arm thereof attaching a medicament transport system of the present disclosure to the syringe.
Figure 31:
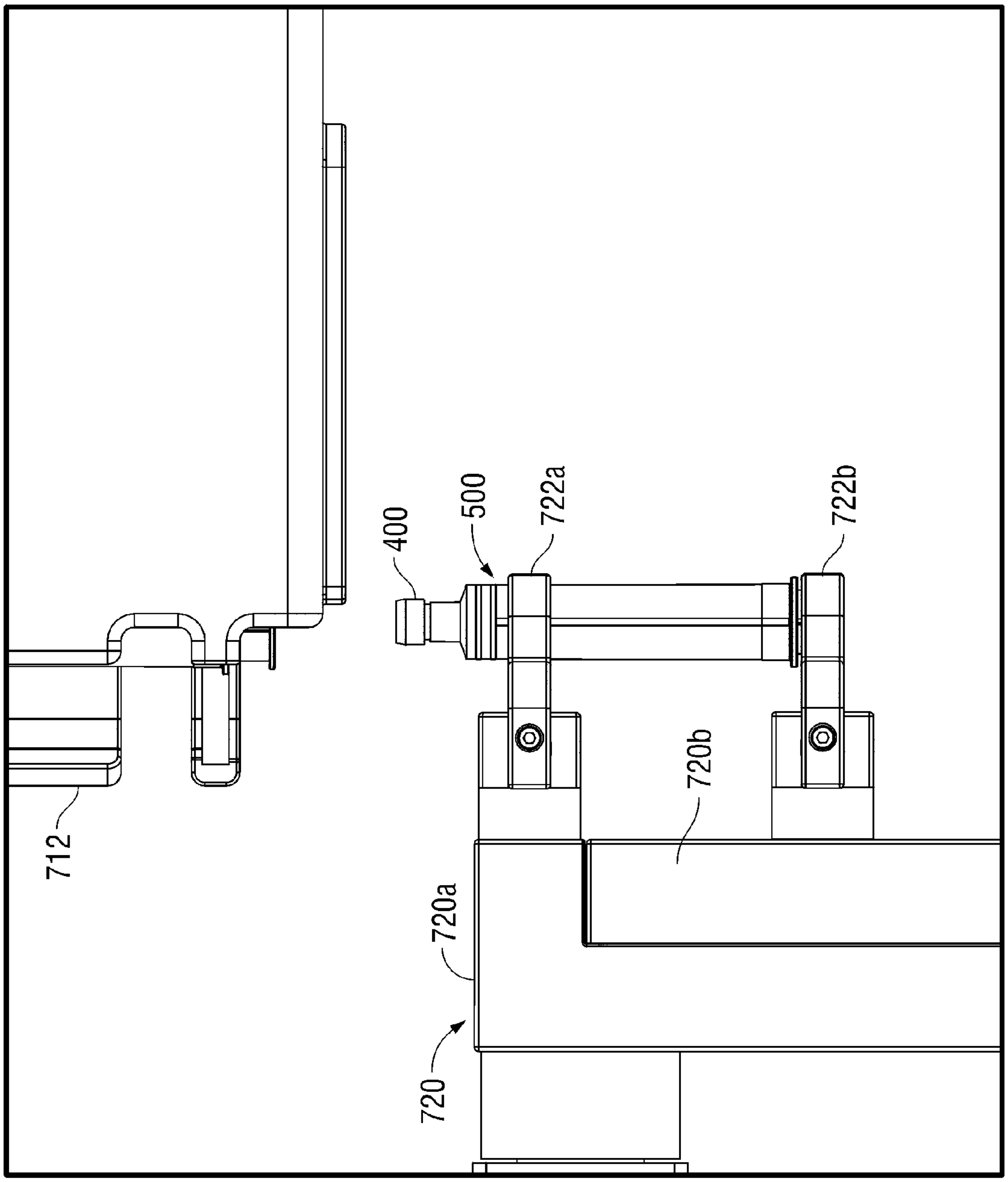
FIG. 31 is enlarged detail view of the automated system of FIG. 26, shown with the a syringe, having the medicament transport system connected thereto, being held by the loading arm.
Figure 32:
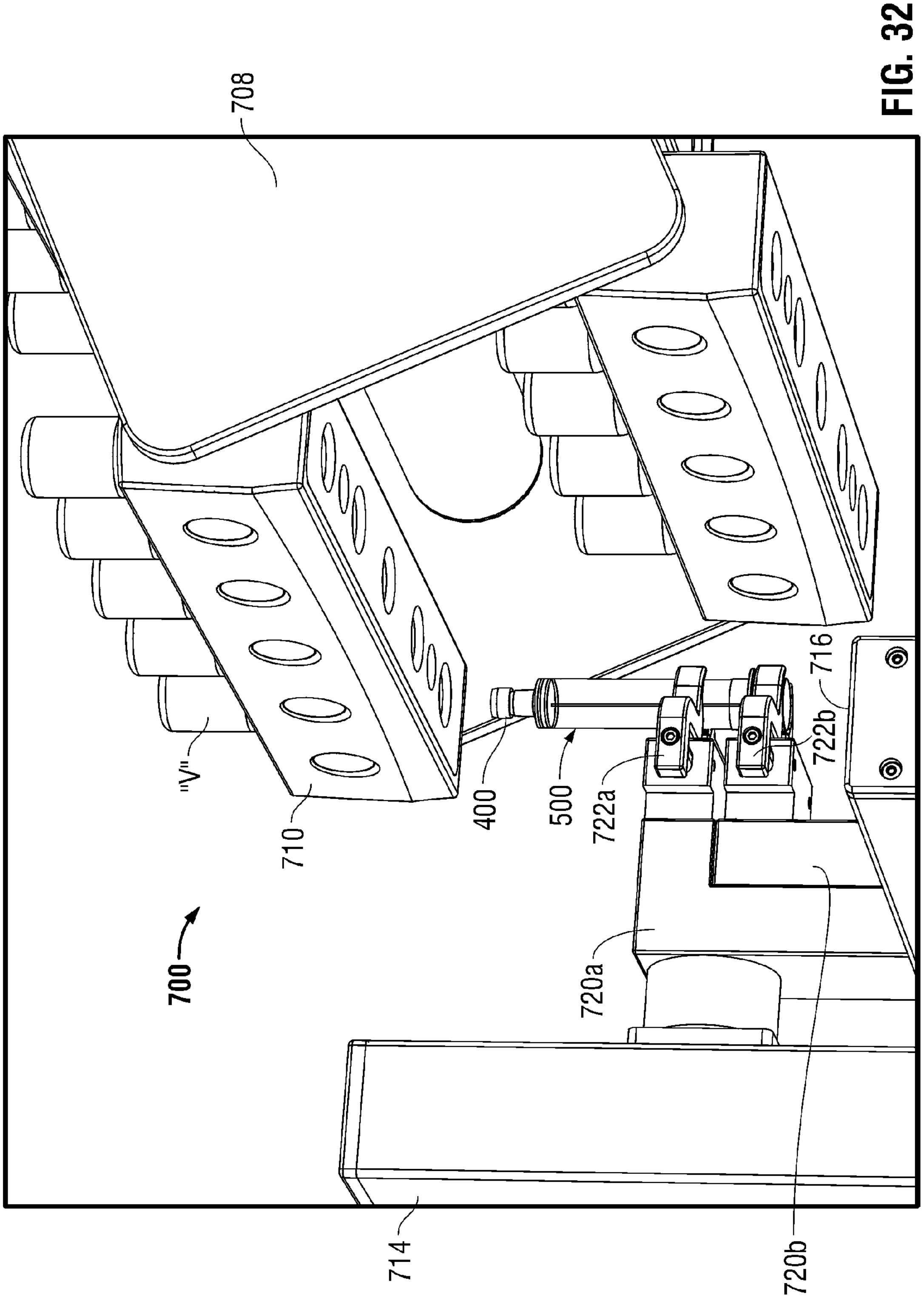
FIG. 32 is enlarged detail view of the automated system of FIG. 26, shown with the loading arm having moved the syringe into registration with a predetermined medicament containing vial loaded in the automated system.

At Step 914 the extraction process is performed. At Step 914*a*, as seen in FIGS. 26-31, extraction or loading arm 714 selects an appropriate syringe. At Step 914*b* loading arm 714 engages the selected syringe and secures the selected syringe into place via clamping mechanism or fingers 722*a*, 722*b*. At Step 914*c* loading arm 714 is slid back along track or rails 716, 718 to a syringe adapter assembly connection site. At Step 914*d*, as seen in FIGS. 30 and 31, a syringe adapter assembly 400 is connected to the syringe 500. At Step 914*e*, as seen in FIG. 32, the syringe 500 having the syringe adapter assembly 400 connected thereto is moved by loading arm 714 to an extraction site corresponding to a loaded vial.

Figure 33:
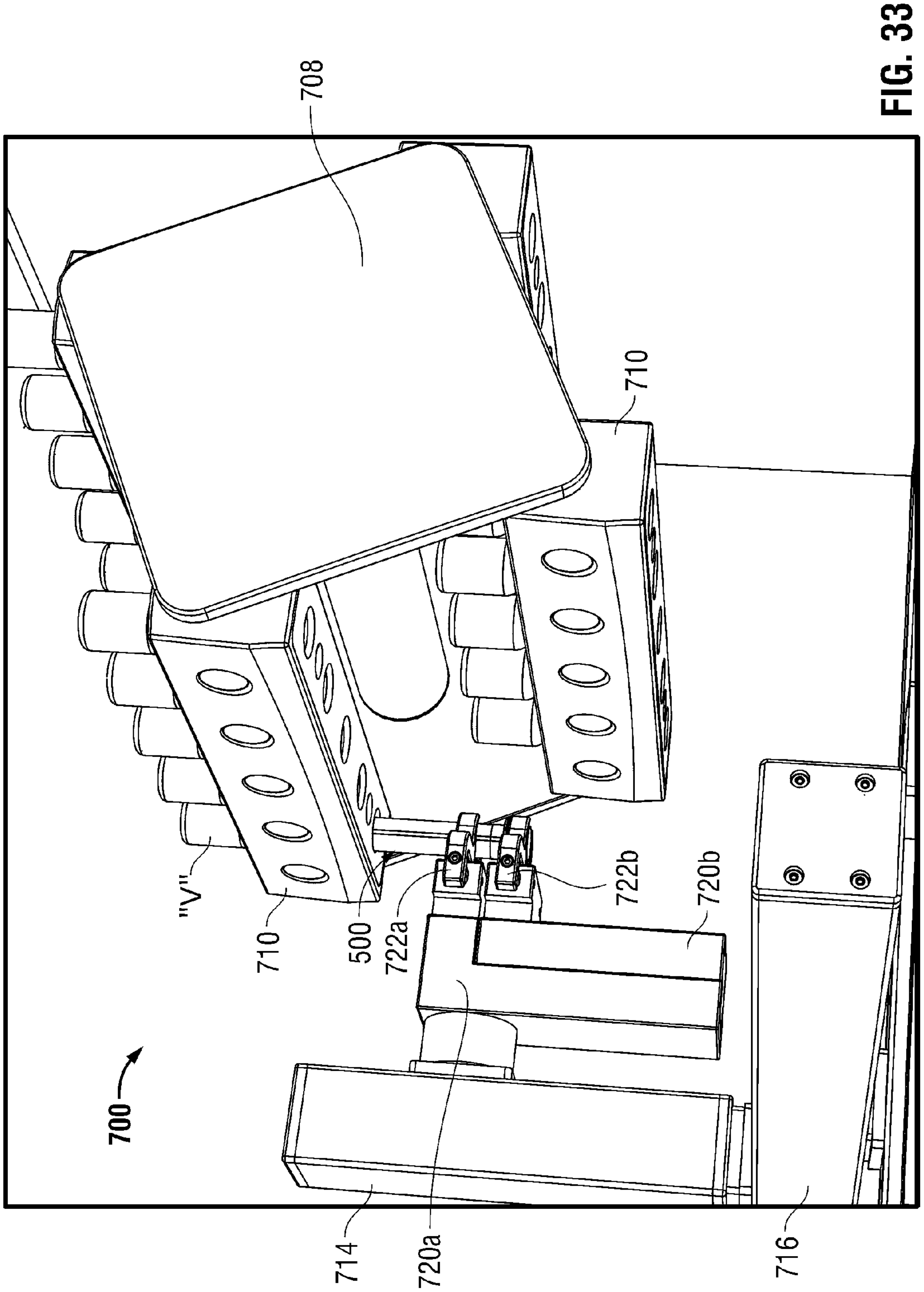
FIG. 33 is enlarged detail view of the automated system of FIG. 26, shown with the loading arm having advanced the syringe into operative engagement with the predetermined medicament containing vial.

With loading arm 714 engaging a plunger of the syringe, at Step 915*a*, loading arm 714 moves the syringe to a vial engagement access site. At Step 915*b*, as seen in FIG. 33, the syringe 500 engages the capped vial “V”, wherein a seal of the syringe adapter assembly makes connection with a seal of the vial adapter assembly. At Step 915*c*, loading arm 714 continues to advance the syringe toward the vial until a seal or stopper of the vial is engaged by a seal of the vial adapter assembly and until a sealed connection is established between the vial and the syringe. At Step 916, loading, arm 714 begins the extraction process.

Figure 34:
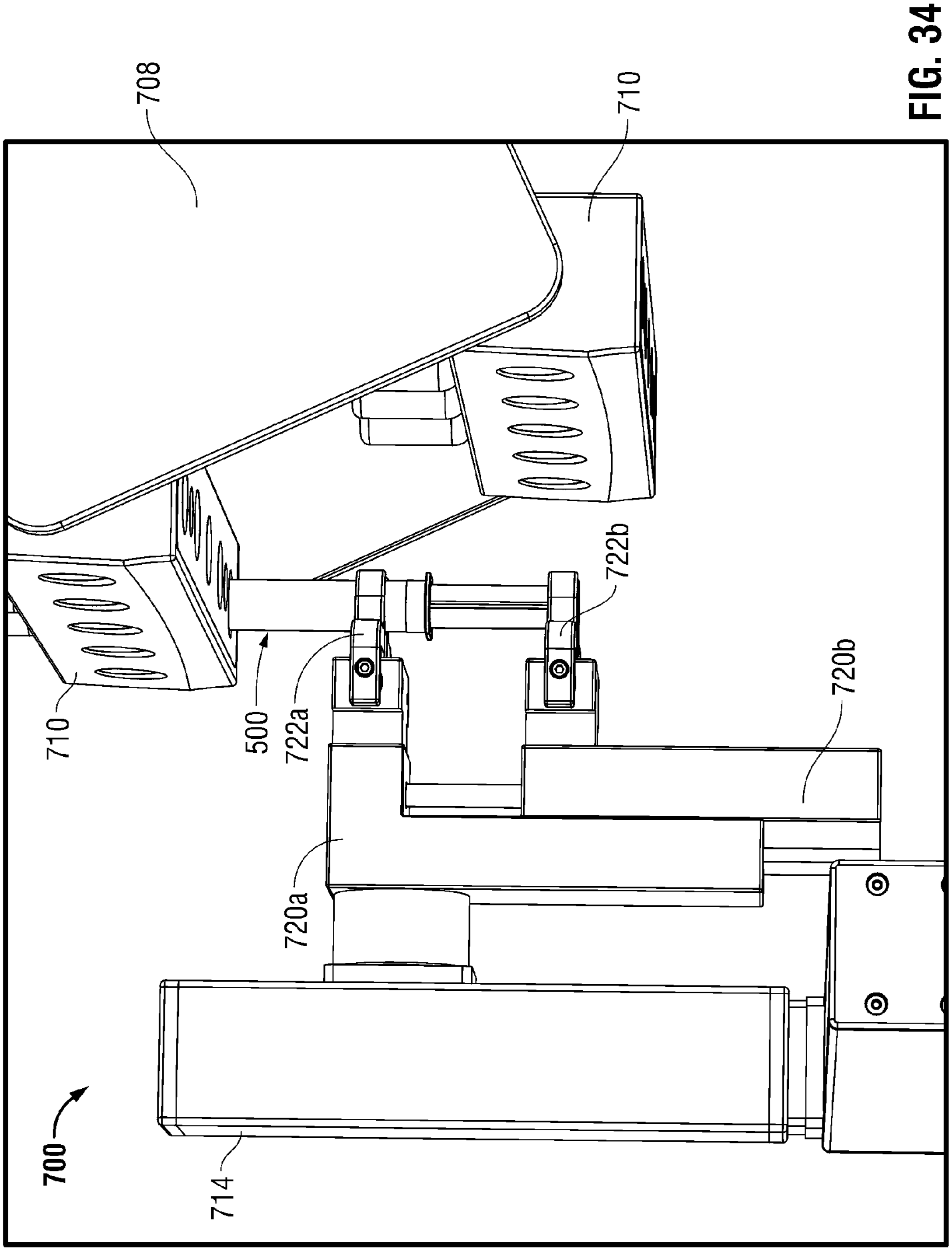
FIG. 34 is enlarged detail view of the automated system of FIG. 26, shown with the loading arm having actuated the syringe to withdraw a quantity of a medicament from the vial.
Figure 35:
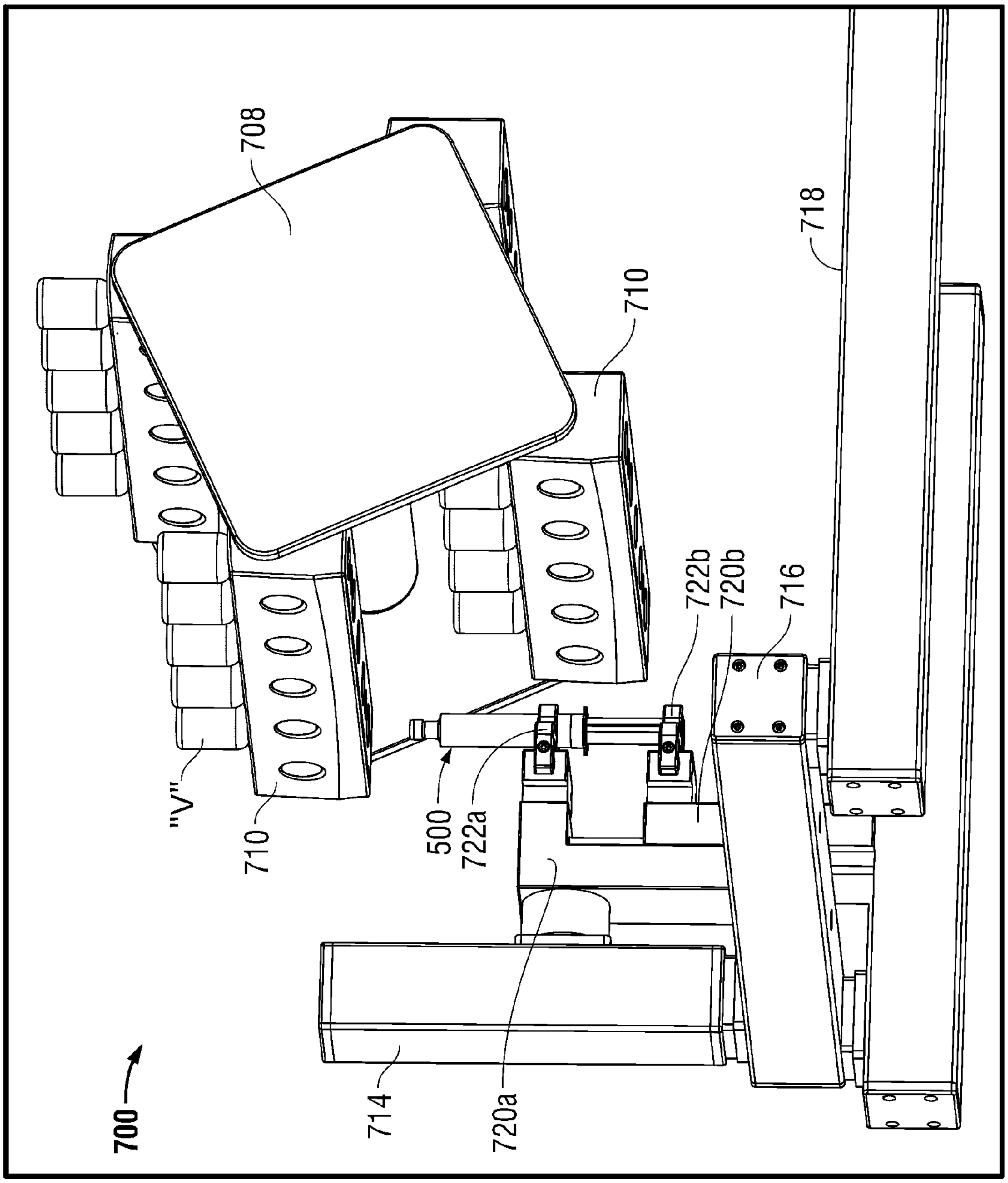
FIG. 35 is enlarged detail view of the automated system of FIG. 26, shown with the loading arm having separated the medicament filled syringe from the vial.
Figure 39C:
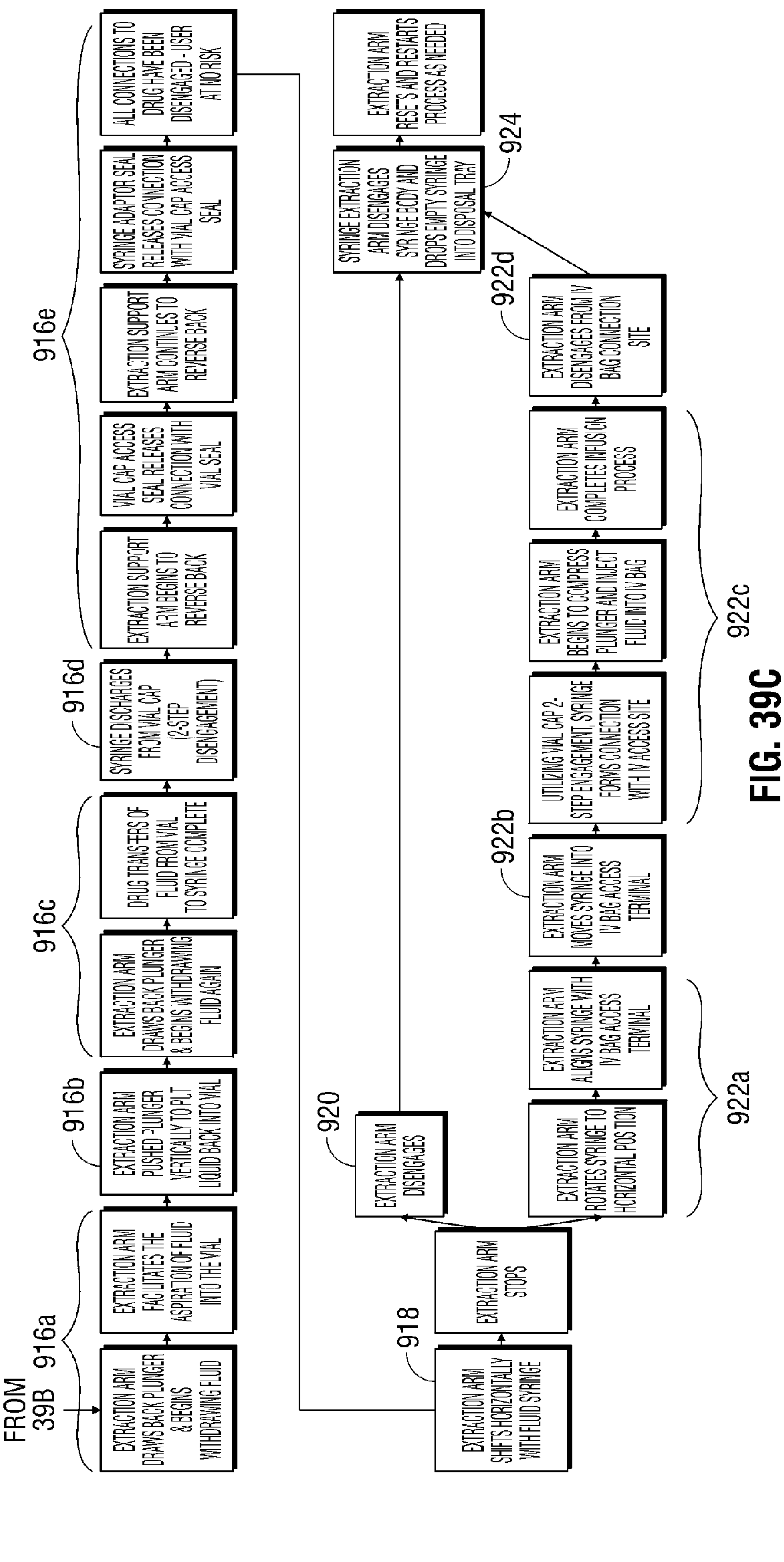

As seen in FIG. 39C, at Step 916*a*, as seen in FIG. 34, loading arm 714 withdraws the plunger relative to the syringe barrel of the syringe 500 to begin withdrawing fluid from the vial “V” and facilitate aspiration of fluid into the vial “V.” At Step 916*b*, loading arm 714 advances the plunger relative to the barrel of the syringe to inject fluid back into the vial. Step 916*c*, loading arm 714 once again withdraws the plunger relative to the barrel of the syringe to again withdraw fluid from the vial to complete the transfer of drug from the vial to the syringe. At Step 916*d*, as seen in FIG. 35, the syringe 500 filed with the medicament is disengaged from the vial adapter assembly. At Step 916*e*, loading arm 714 moves away from the vial such that the seal of the vial adapter assembly is disengaged from the seal of the vial and the seal of the syringe adapter assembly is disengaged from the seal of the vial adapter assembly.

Figure 36:
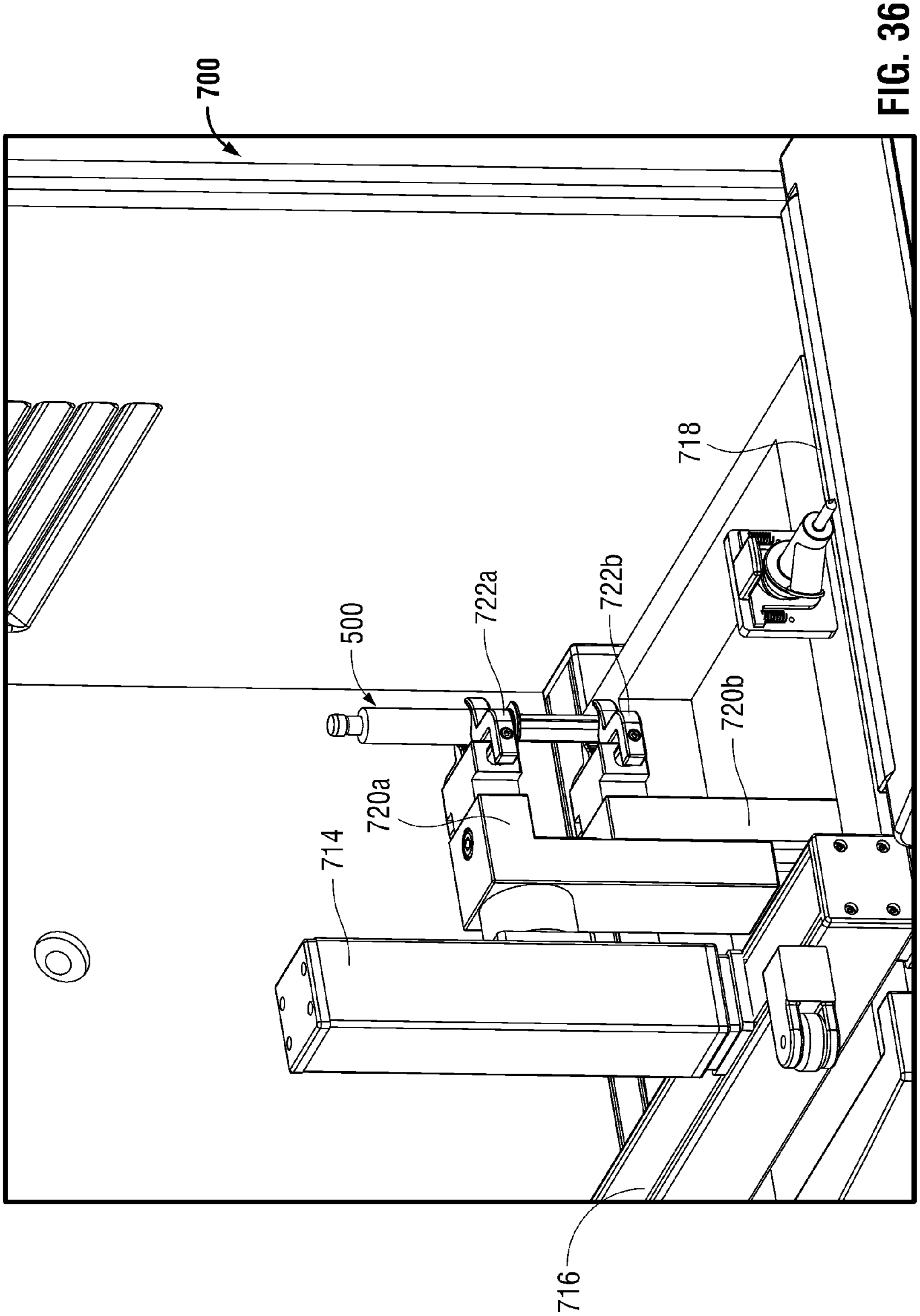
FIG. 36 is enlarged detail view of the automated system of FIG. 26, shown with the loading arm having moved the filled syringe to another location.

At Step 918, as seen in FIG. 36, loading arm 714, holding the filled syringe, is moved horizontally away from the tray of vials. At Step 920, loading arm 714 may disengage and release the filled syringe.

Alternatively, at Step 922*a*, as seen in FIG. 37, loading arm 714 reorients the filled syringe 500 to align a nose of the syringe with an access terminal 602 of an IV bag 600. At Step 922*b*, loading arm 714 moves the nose of the syringe into the access terminal 602 of the IV bag 600. With the nose of the syringe connected to the access terminal 602 of the IV bag 600, at Step 922*c*, loading arm 714 actuates the plunger of the syringe to inject the fluid of the syringe into the IV bag 600. At Step 922*d*, loading arm 714 disengages the syringe from the access terminal 602 of the IV bag 600.

At Step 924, loading arm 714 disengages the used and empty syringe and drops the used and empty syringe to a disposal tray. The entire process may be repeated as many times as necessary.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

What is claimed is:

1. An automation system for forming a medicament solution from a vial containing one of a liquid and a non-liquid material, the system comprising:

a cabinet housing a carousel configured to hold a plurality of vials, at least one magazine of syringes, a loading arm movable within the cabinet for transporting syringes to vials loaded in the carousel, and a plurality of medicament transport systems for fluidly interconnecting the syringes to the vials;

each medicament transport system comprising:

a syringe adapter assembly fluidly connectable to a first container, the syringe adapter assembly including:

a body portion defining a lumen therethrough; and a seal member connected to a distal end of the body portion and extending across the lumen thereof; and a vial adapter assembly connectable to a neck of the vial and configured to receive the body portion of the syringe adapter assembly, the vial adapter assembly including:

a base having at least one retainer configured to engage the neck of the vial, the base defining an opening having a seal member disposed therewithin;

a stem extending from the base, the stem defining a lumen therethrough and being in operative communication with the opening of the base, the stem defining an opening through a wall thereof;

a needle shuttle valve slidably disposed within the lumen of the stem, the needle shuttle valve forming a fluid tight seal with the stem, the needle shuttle valve supporting a transfer needle such that the transfer needle extends from a first and a second end thereof and supporting a vacuum needle such that the vacuum needle extends from the first end of the needle shuttle valve; and a vacuum cup slidably supported on the stem, the vacuum cup being in fluid tight contact with the stem and with the base, wherein a vacuum chamber is defined in the space between the base, the stem and the vacuum cup, the vacuum chamber being in fluid communication with the lumen of the stem through the opening formed in the wall of the stem;

wherein the medicament transport system includes a first condition in which the needle shuttle valve is in a retracted position such that the transfer needle and the vacuum needle do not extend through the seal member of the base of the vial adapter, and the vacuum cup is in an advanced position such that the volume of the vacuum chamber is at a minimum;

wherein the medicament transport system includes a second condition in which the body portion of the syringe adapter assembly is advanced through the lumen of the stem such that the second end of the transfer needle penetrates through the seal member of the body portion and the needle shuttle valve is advanced through the lumen of the stem to penetrate the first end of the transfer needle and a tip of the vacuum needle through the seal member of the vial adapter assembly, and wherein the vacuum needle is brought into fluid communication with the opening formed in the wall of the stem; and wherein the medicament transport system includes a third condition in which the vacuum cup is moved to a proximal position thereby enlarging the vacuum chamber and drawing a vacuum through the vacuum needle.

2. The automation system according to claim 1, wherein the carousel includes at least one tray configured to support at least one vial, wherein the tray is pivotally connected on the carousel.

3. The automation system according to claim 2, wherein each tray extends in a horizontal direction.

4. The automation system according to claim 1, wherein the loading arm is configured to remove a syringe from the magazine, connect a syringe adapter assembly to the syringe, and transport the syringe to a vial having a vial adapter assembly connected thereto.

5. The automation system according to claim 4, wherein the loading arm is configured to connect the syringe adapter assembly that is connected to the syringe to at least one of the vial adapter assembly that is connected to the vial.

* * * * *